(12) United States Patent
Webb et al.

(10) Patent No.: US 9,969,765 B2
(45) Date of Patent: May 15, 2018

(54) NUCLIONS AND RIBOCAPSIDS

(75) Inventors: Nigel L. Webb, Bryn Mawr, PA (US); Howard B. Gamper, Philadelphia, PA (US)

(73) Assignee: Nigel L. Webb, Bryn Mawr, PA (US)

( * ) Notice: Subject to any disclaimer, the term of this patent is extended or adjusted under 35 U.S.C. 154(b) by 463 days.

(21) Appl. No.: 13/883,918

(22) PCT Filed: Nov. 7, 2011

(86) PCT No.: PCT/US2011/059656
§ 371 (c)(1),
(2), (4) Date: Jun. 4, 2013

(87) PCT Pub. No.: WO2012/064675
PCT Pub. Date: May 18, 2012

(65) Prior Publication Data
US 2013/0267695 A1    Oct. 10, 2013

Related U.S. Application Data

(60) Provisional application No. 61/411,974, filed on Nov. 10, 2010.

(51) Int. Cl.
*C07H 21/02* (2006.01)
*C12Q 1/68* (2018.01)
*C12P 19/34* (2006.01)

(52) U.S. Cl.
CPC .......... *C07H 21/02* (2013.01); *C12Q 1/6883* (2013.01); *C12Q 1/6886* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2009/0035836 A1 | 2/2009 | Datta et al. |
| 2009/0155844 A1 | 6/2009 | Yokoyama et al. |
| 2010/0087677 A1 | 4/2010 | Tian |
| 2010/0160618 A1 | 6/2010 | Chin et al. |

FOREIGN PATENT DOCUMENTS

WO    WO 97/33991 A1    9/1997

*Primary Examiner* — Nancy J Leith
(74) *Attorney, Agent, or Firm* — Morgan, Lewis & Bockius LLP

(57) ABSTRACT

The invention relates to an isolated nuclion having (i) a core nucleic acid, and (ii) one or more ribocapsids each including a polymer of two or more ribocapsid subunits, wherein said ribocapsid subunits include nucleic acid. The invention also relates to a method for manufacturing an isolated nuclion.

29 Claims, 39 Drawing Sheets
(26 of 39 Drawing Sheet(s) Filed in Color)

© 2011 Nigel Webb

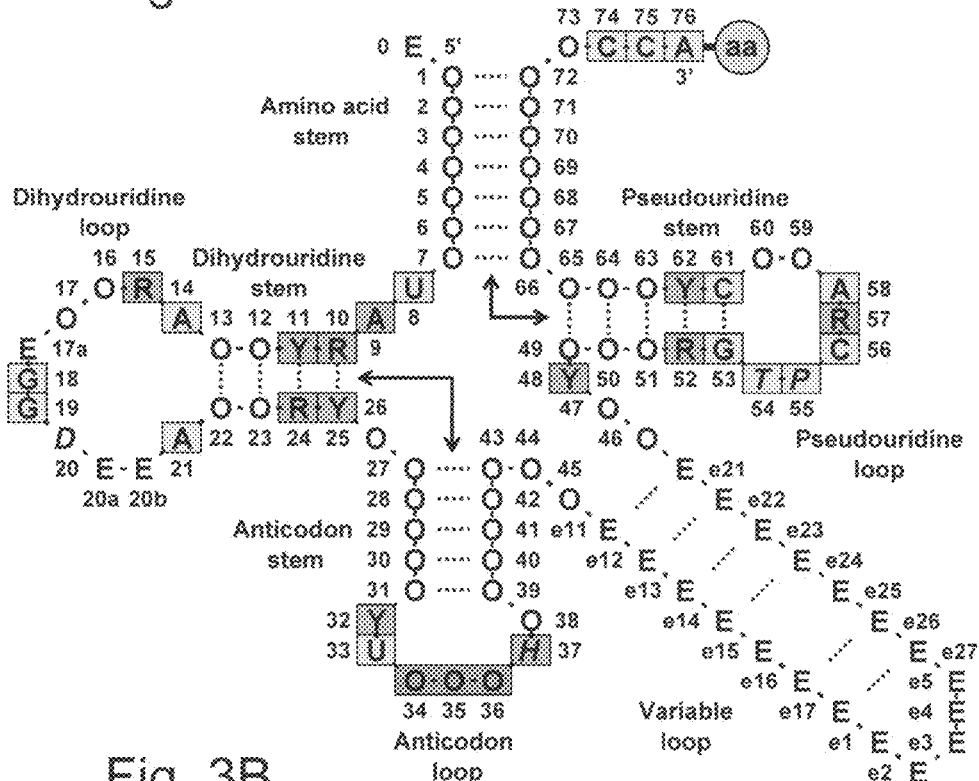

Fig. 4A
Fig. 4B
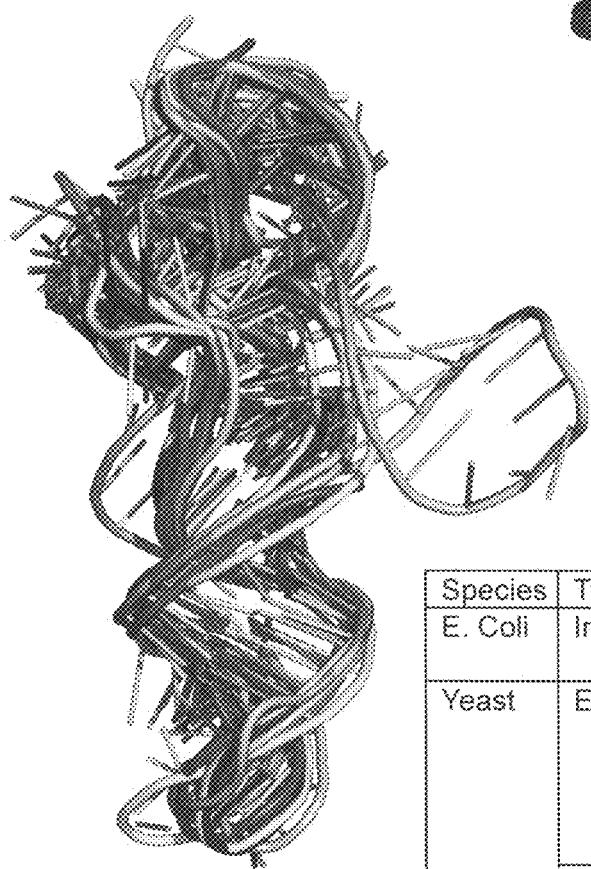
Fig. 4C
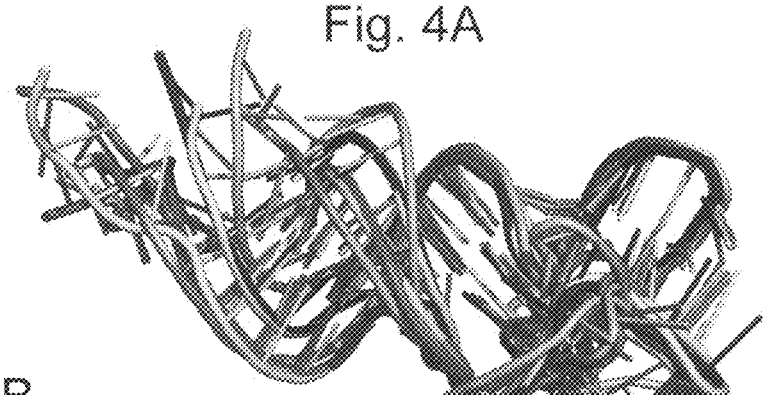
© 2011 Nigel Webb

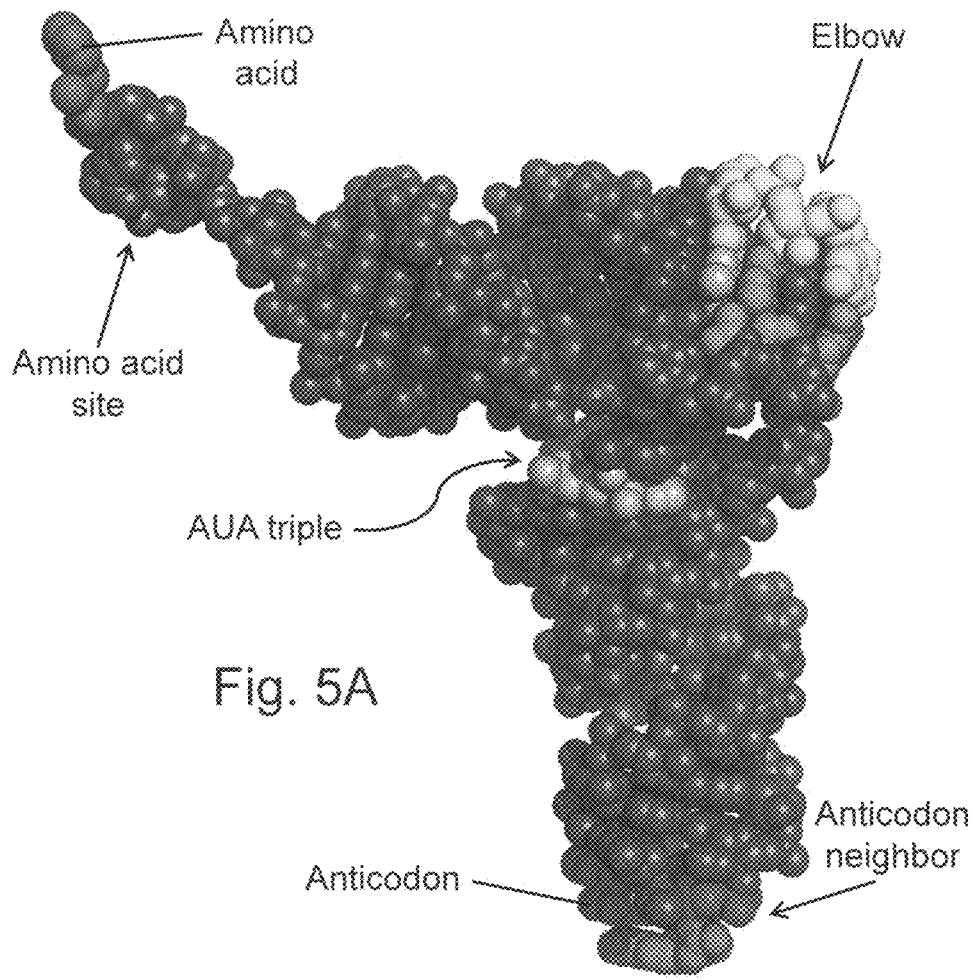

| Layer | GSP90 nucleotides & conserved purine | Type of base pair |
|---|---|---|
| L1 | G56 = G19 | Watson-Crick |
| L2 | R57 (purine) | None |
| L3 | P55 = G18 | Other |
| L4 | T54 = A58 | Other |
| L5 | G53 = C61 | Watson-Crick |

| Layer | L1 | L2 | L3 | L4 | L5 |
|---|---|---|---|---|---|
| tRNA | C56 |  | P55 | T54 | G53 |
|  | G19 | R57 | G18 | A58 | C61 |
| Nucleotide key | | | | | |

© 2011 Nigel Webb

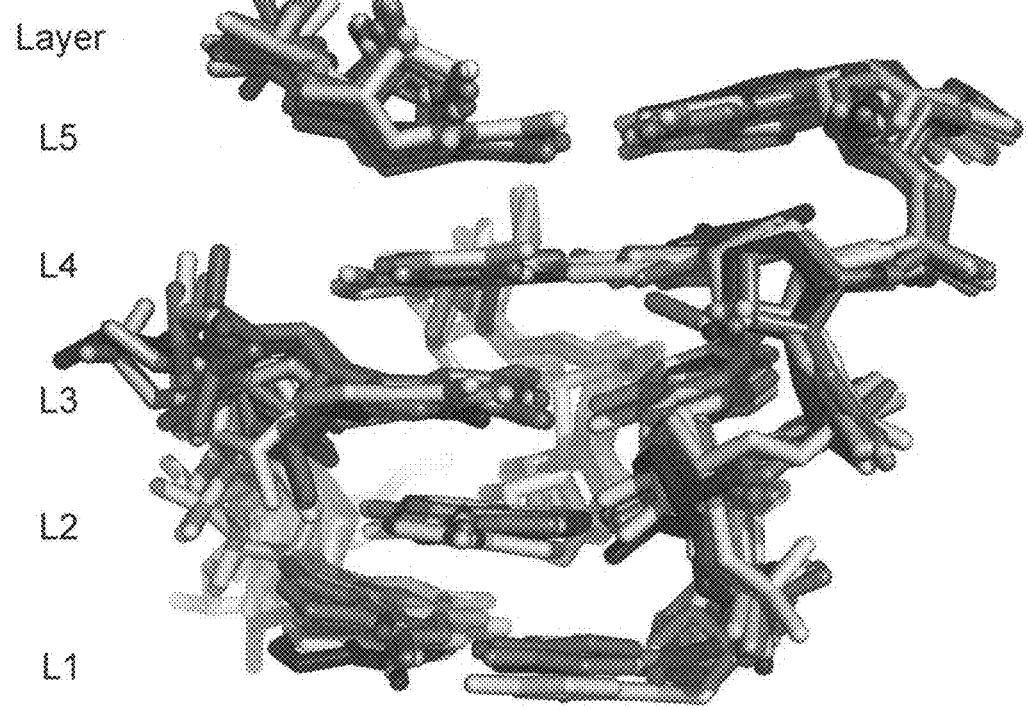

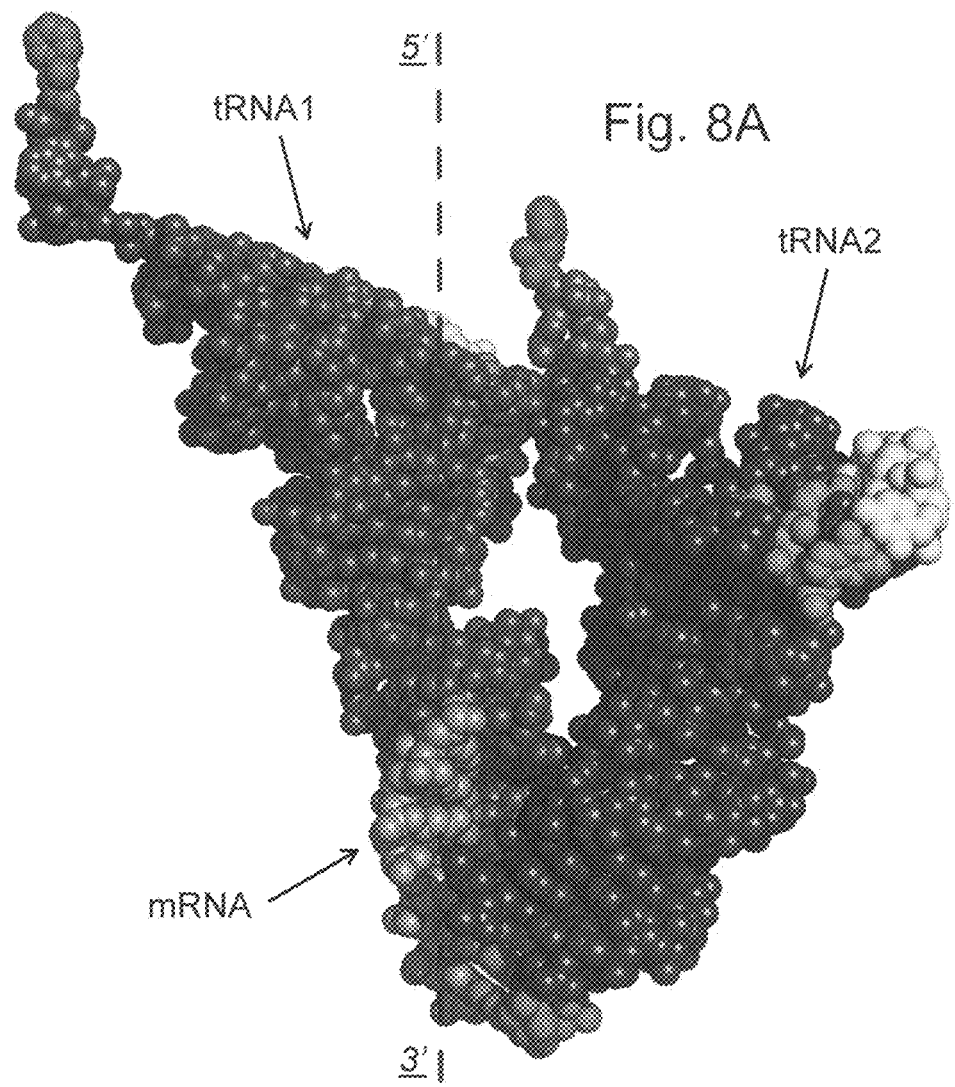
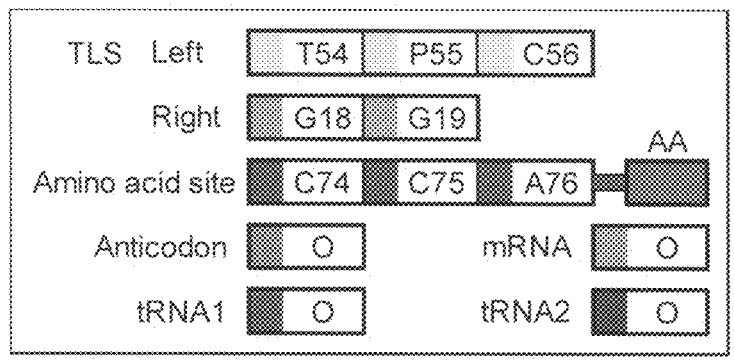
© 2011 Nigel Webb

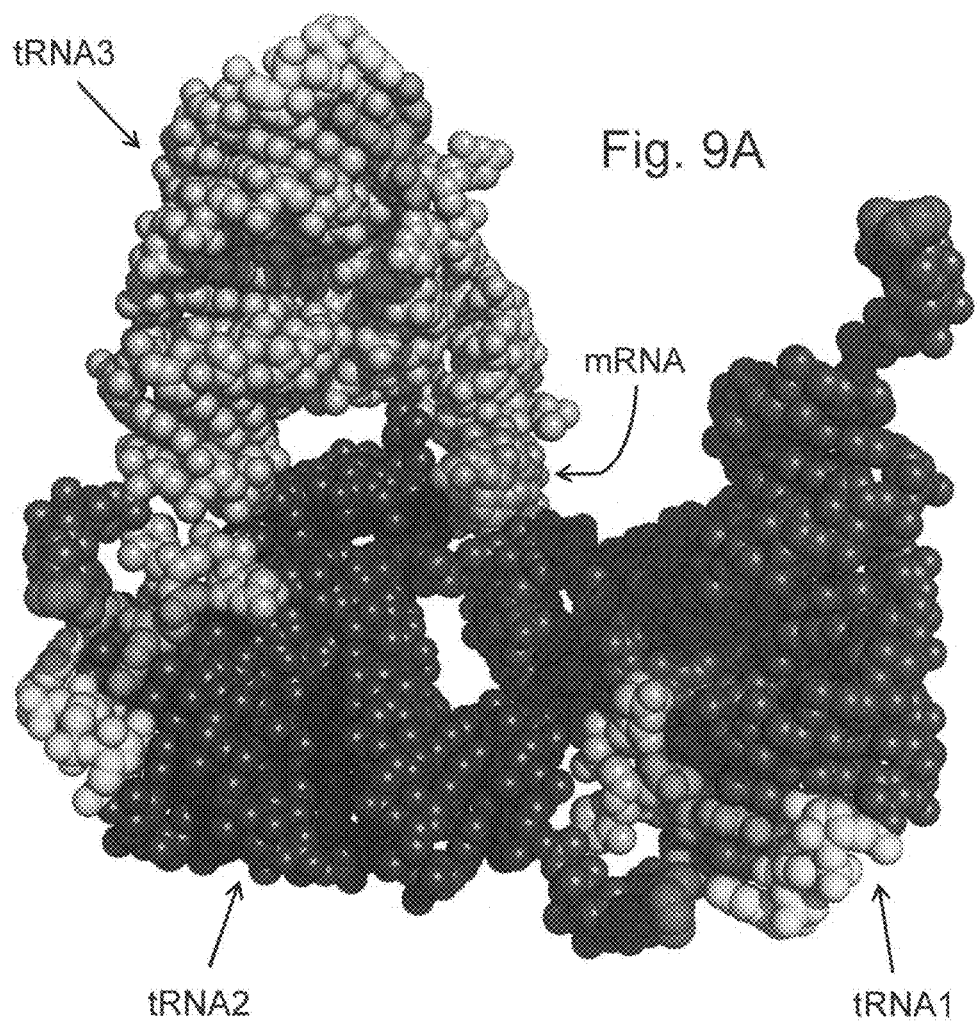
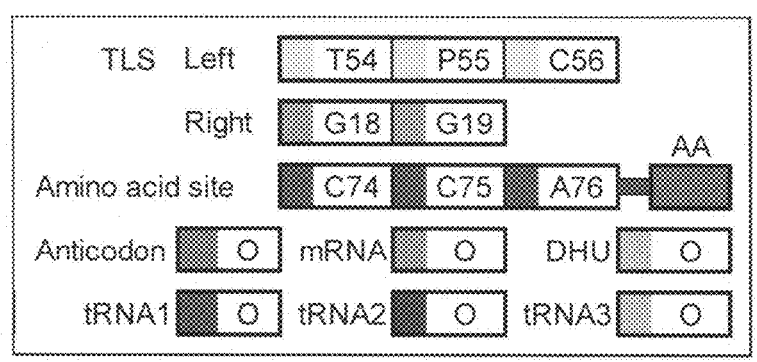

| Conformation | | Helix (per tRNA) | |
|---|---|---|---|
| Nuclion | Anti-codon | Rise (Å) | Turn (degrees) |
| S | K | ~ 8.4 | ~ 98 |

| Conformation | | Helix (per tRNA) | |
|---|---|---|---|
| Nuclion | Anti-codon | Rise (Å) | Turn (degrees) |
| T | L | ~ 15 ± 3 | ~ 98 ± 10 |

Key

■ Codons

All other colors are anticodons

© 2011 Nigel Webb

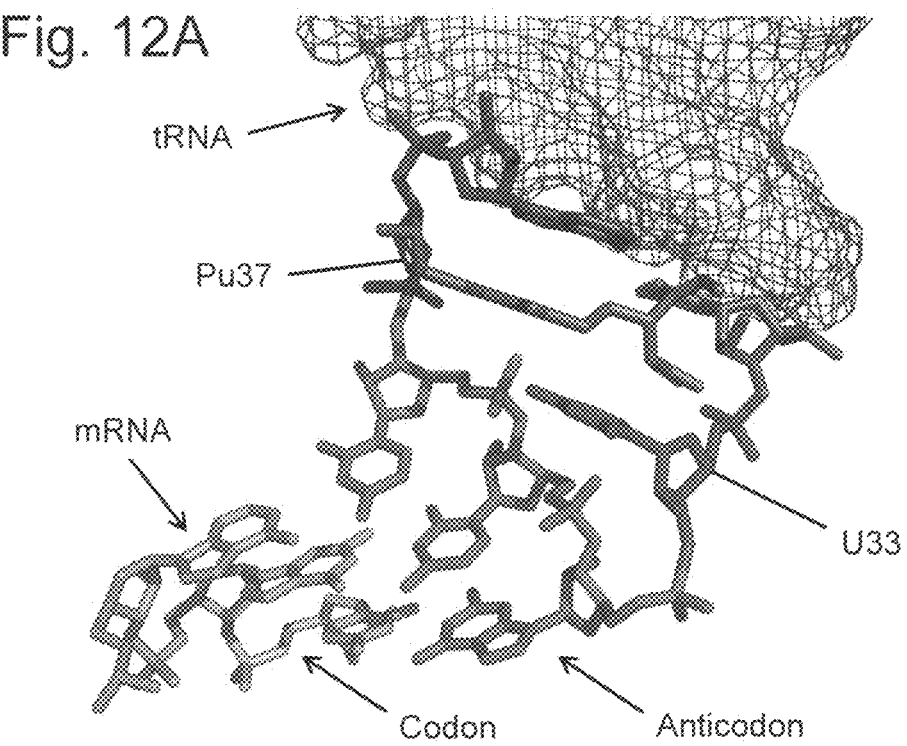
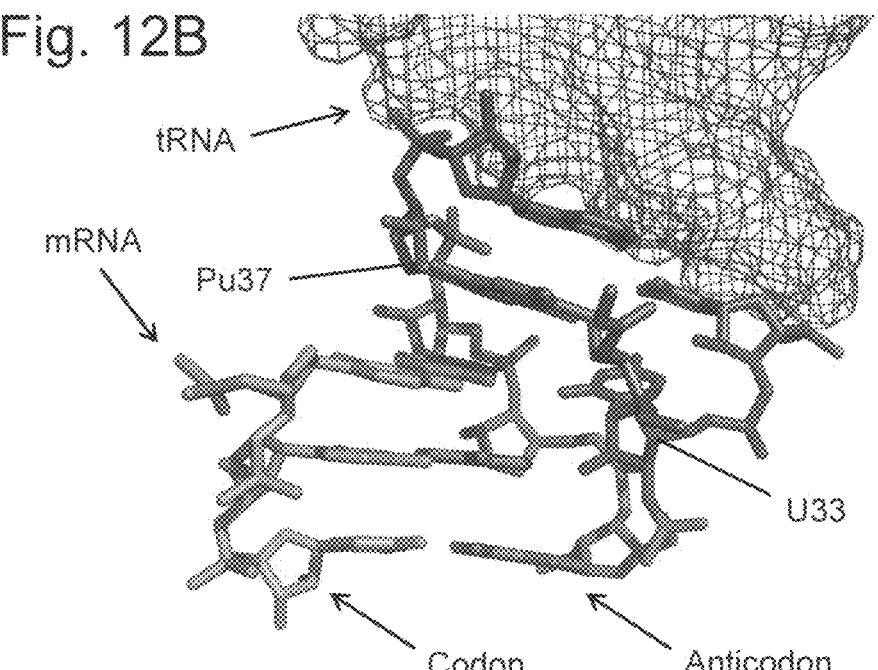

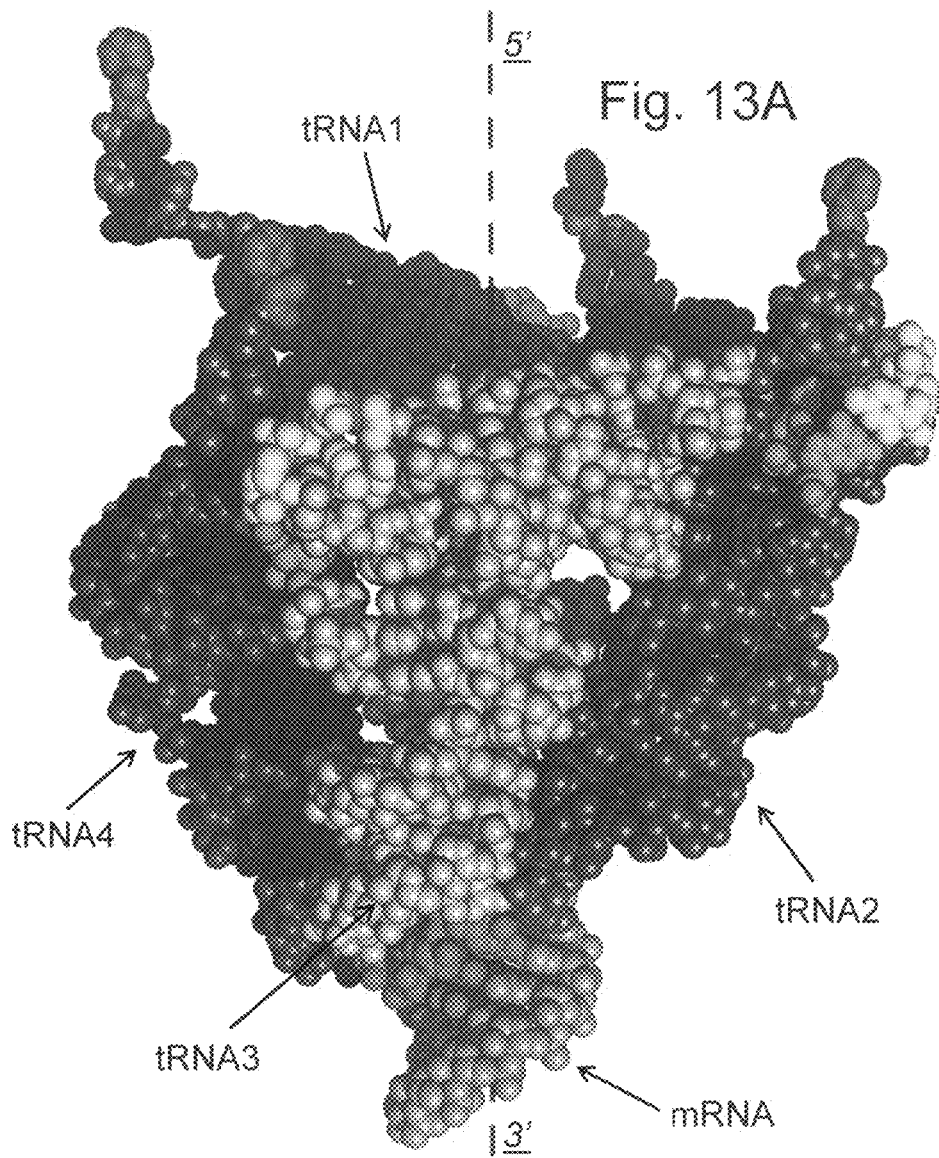
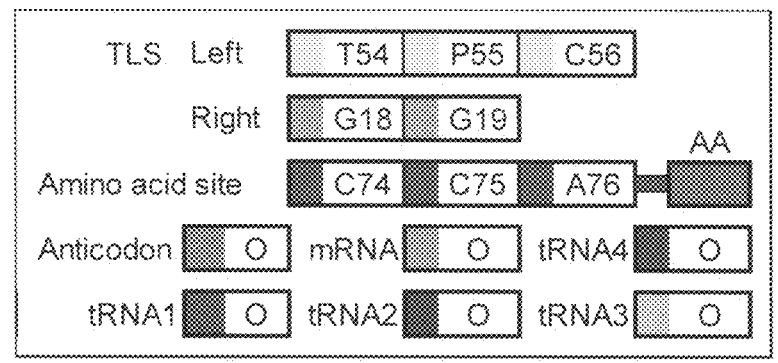
© 2011 Nigel Webb

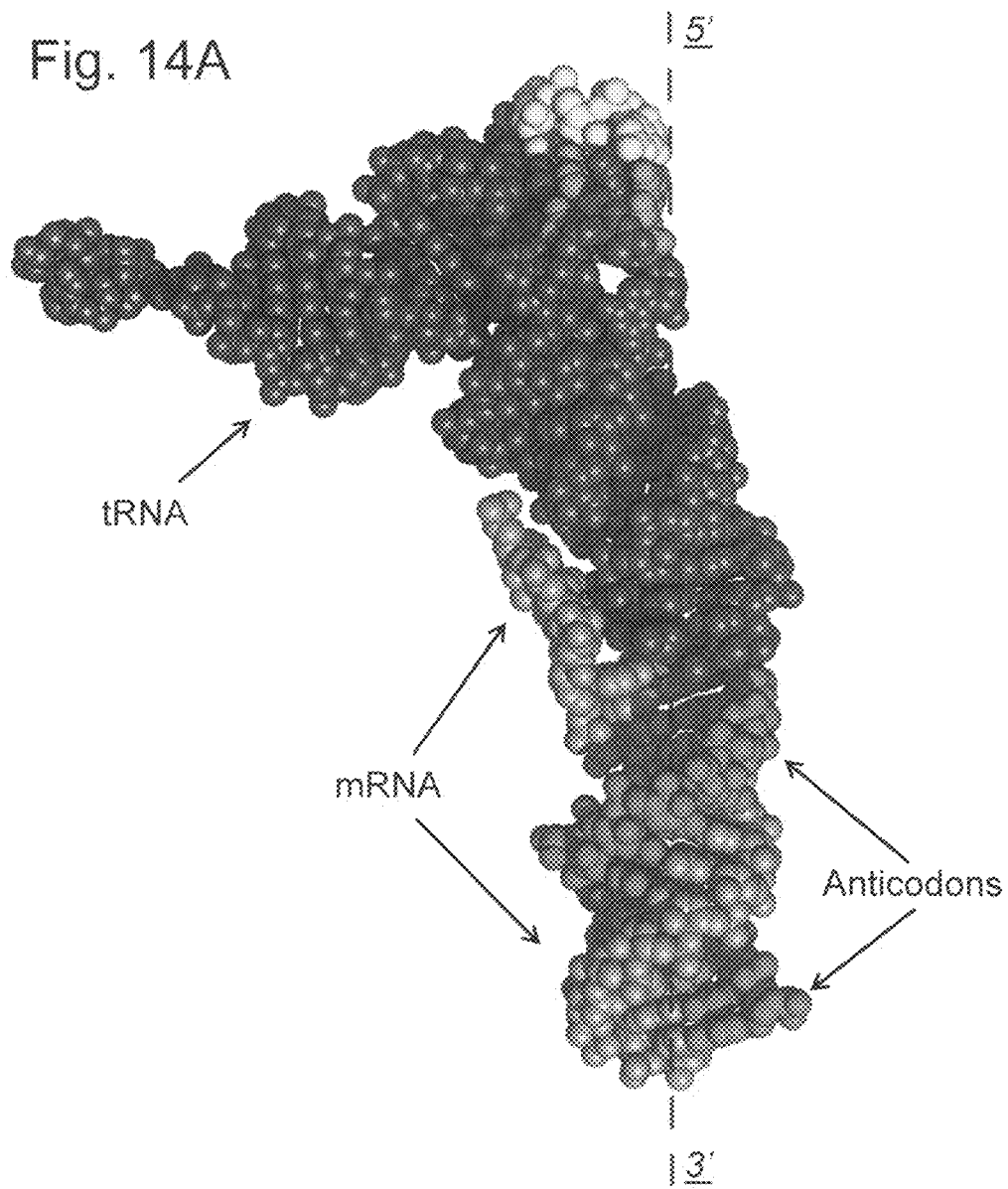

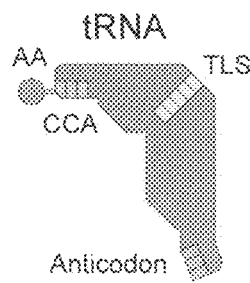

Fig. 17

| Conformation of nuclion | R | S | T |
|---|---|---|---|
| Maximum number of adjacent tRNAs with the designated conformation | 1 | 4 | Unlimited |
| Turn per tRNA (around nuclion axis) | Cap | ~98° | ~98 ± 10° |
| Rise per tRNA (along nuclion axis) | ~8.4 Å | ~8.4 Å | ~15 ± 3 Å |
| Anticodon loop conformation in tRNA | L | K | L |
| Anticodon stacks with anticodon stem | Yes | No | Yes |
| Adjacent anticodons stack | Yes | Yes | No |
| Adjacent codons stack | Yes | Yes | No |
| Stacked nucleotides per tRNA* | ~T + 8 | ~T + 6 | ~T + 5 |
| Cumulative base pairs on nuclion axis** | B | ~B+3xS | ~B+12+3xT |
| Dipole along nuclion axis | Yes | Yes | Minor |

Key:
* (i) Excludes additional nucleotide stacking at elbow.
  (ii) T = number of stacked nucleotides in free tRNA not bound to nuclion.

** B = no. of axial base pairs in R-tRNA cap and associated codon-anticodon

The symbol ~ means substantially in the range of the indicated number.

© 2011 Nigel Webb

© 2011 Nigel Webb

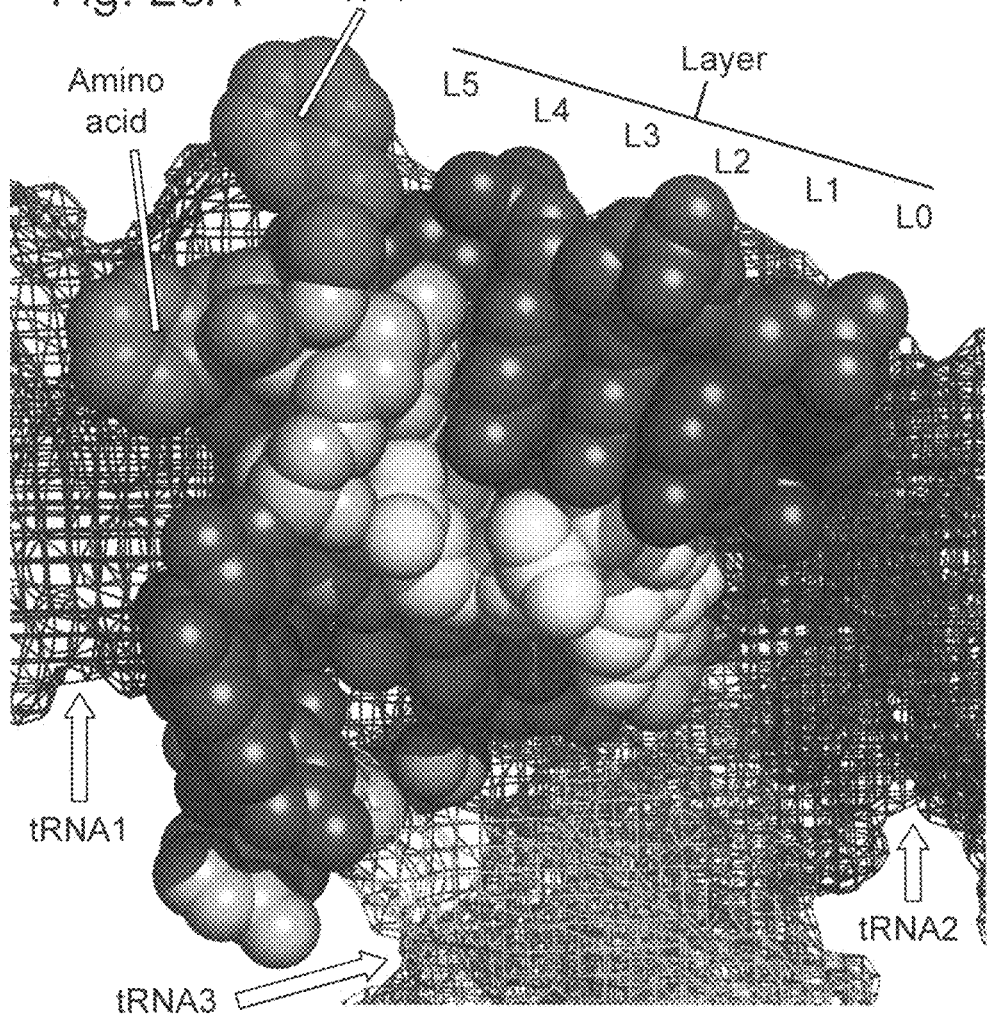
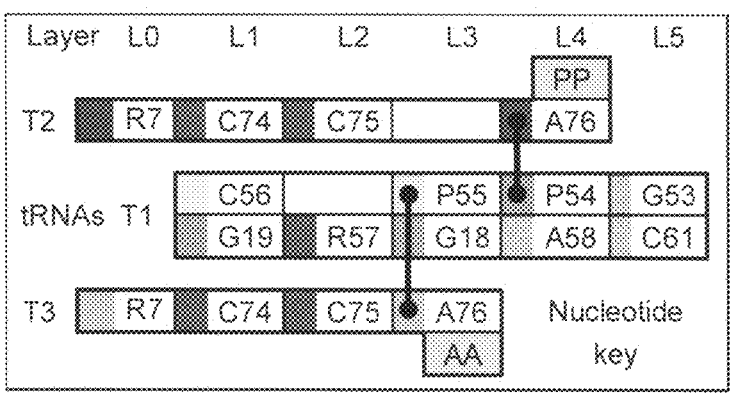
Fig. 23A
Fig. 23B

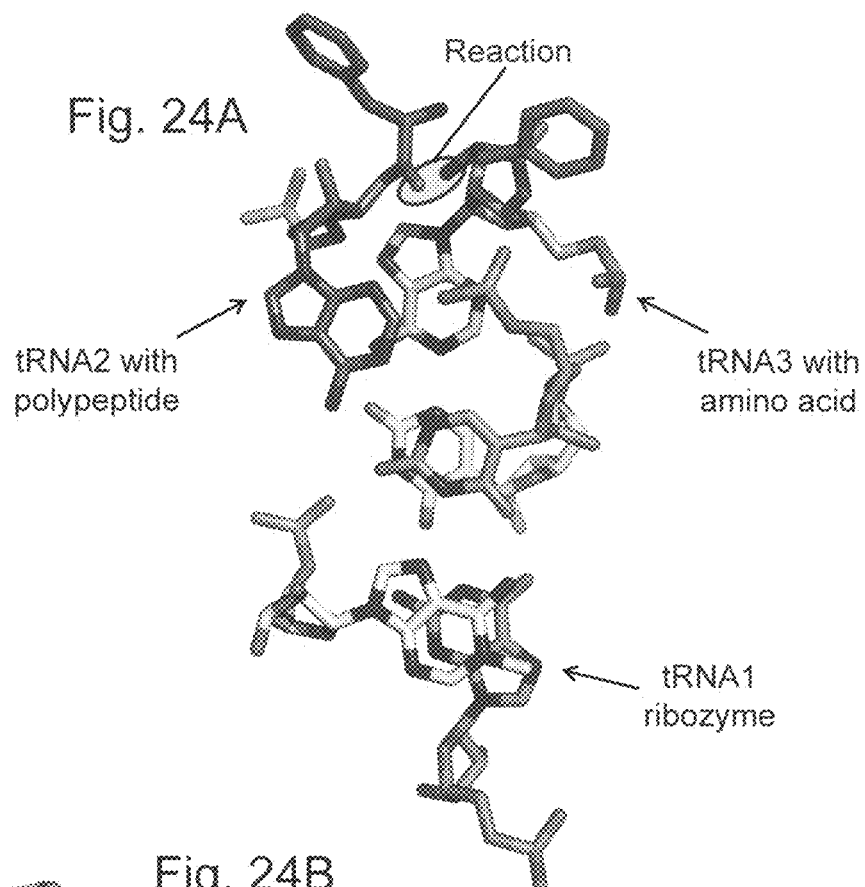
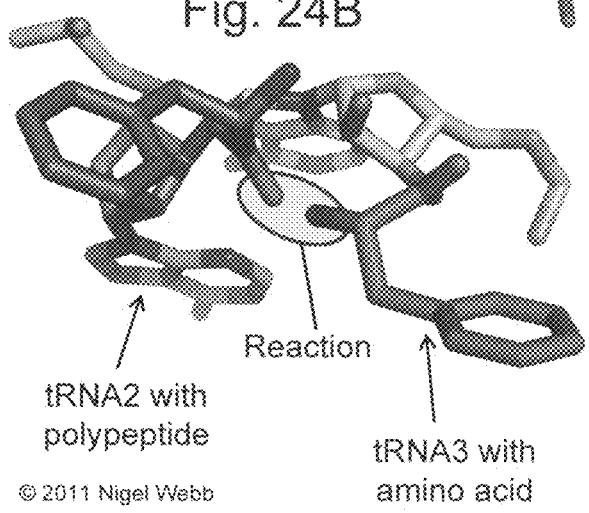

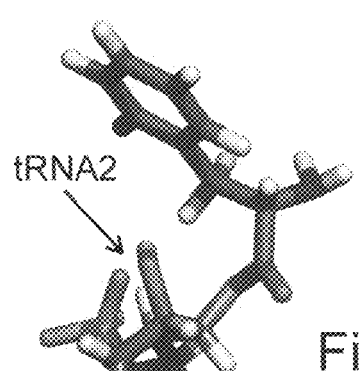
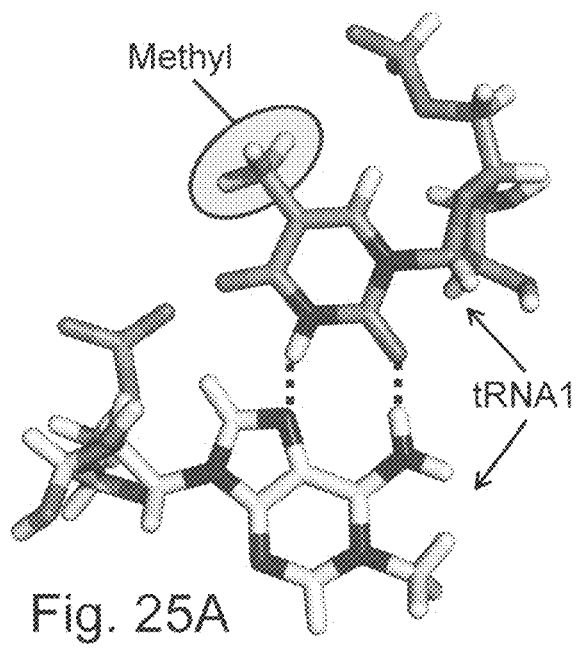
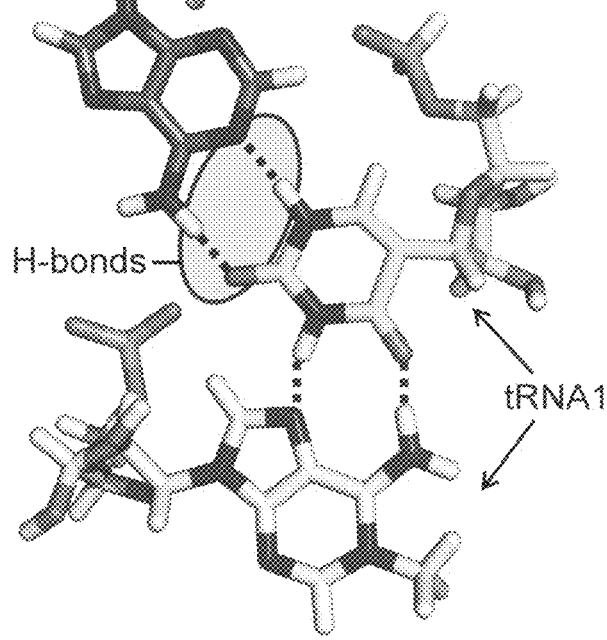

Fig. 26

| Class of tRNA (N) on mRNA codon (N) | Nucleotide in tRNA(N) at position | | Formyl group on amino acid on tRNA (N) | Nuclion form at codon (N) | TLS states in tRNA(N) | | | | Amino acyl CCA binds TLS on tRNA | Result |
|---|---|---|---|---|---|---|---|---|---|---|
| | | | | | TLS left | | TLS right | | | |
| | 54 | 55 | | | State | Binds | State | Binds | | |
| Elongator (all) | U* | P | No | S or T | Off | - | On | N+1 | N-1 | Ribocapsid |
| Initiator (bacteria) | U* | P | Yes | R | Off | - | On | N+1 |  | Initiation flag |
| Initiator (eukaryota) | A | P | No | None | Off | - | Off |  | - | Initiation flag |
| Ribozyme (primordial or abnormal tRNA) | P | P | No | S or T | Off | - | On | N+1 | N-1 | Ribocapsid |
| | | | | R | On | N+1 | On | N+2 | - | Synthesis |

Key

In bacteria (and related organelles in eukaryota):
   F-met on initiator tRNA(N) blocks aminoacyl CCA binding to TLS on tRNA(N-1).
In eukaryota (cytoplasm):
   A54 in TLS on initiator tRNA(N) blocks binding to aminoacyl-CCA on tRNA(N+1).
Nucleotide (NT) codes: P (pseudouridine), U* (uridine or modified U), A (adenosine).
Nuclion forms:    R (cap), S (stacked), T (initial binding).
TLS handedness:   Viewed from amino acid stem in T(N), with anticodon down.

© 2011 Nigel Webb

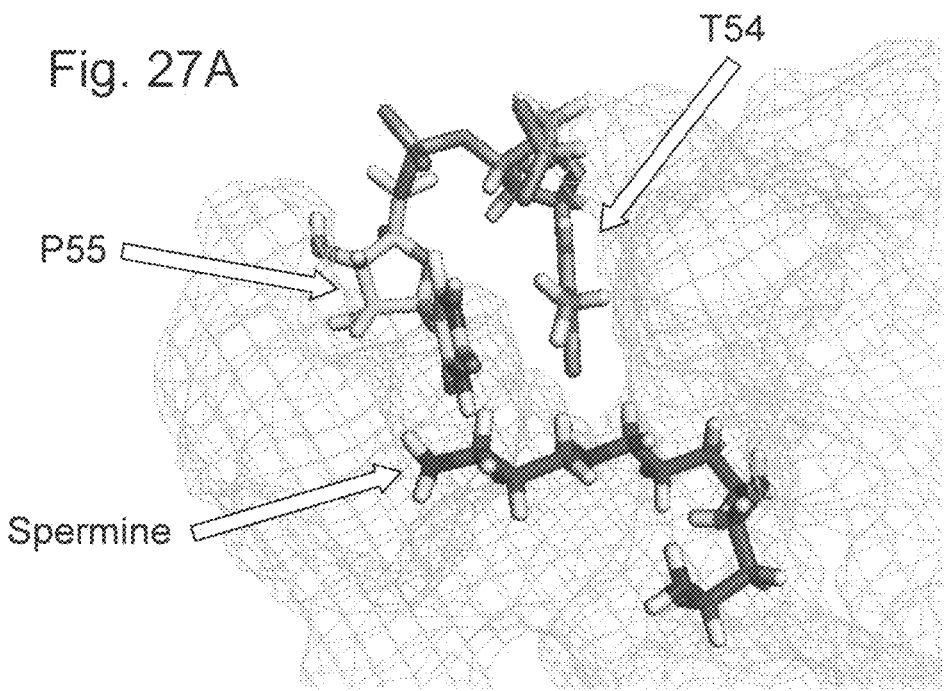
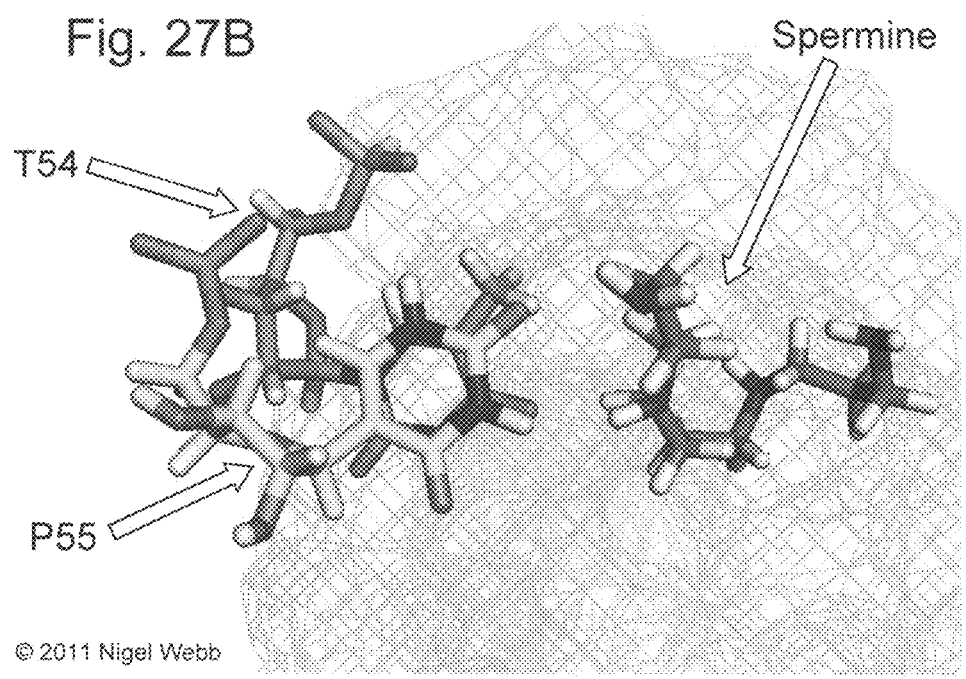

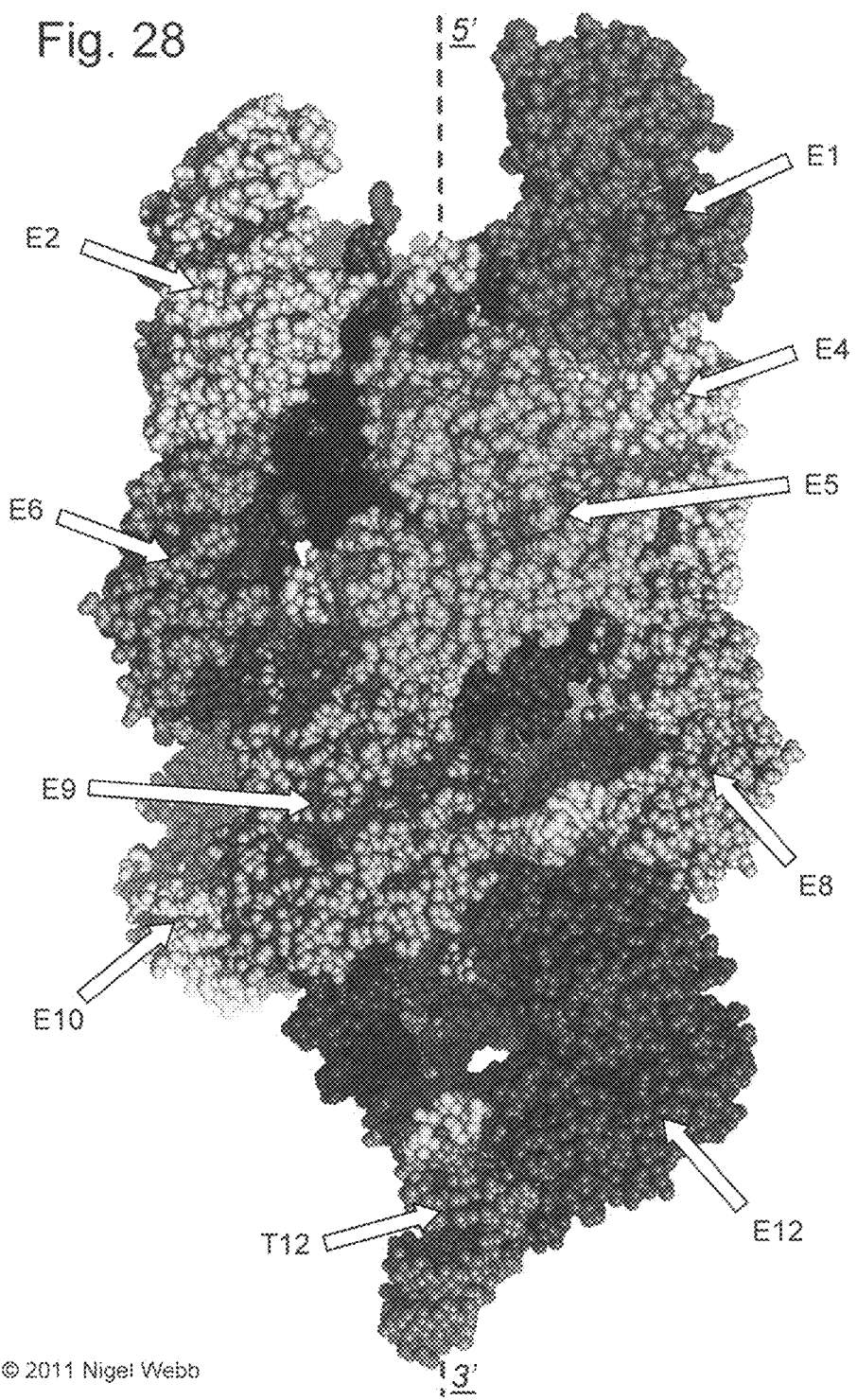

© 2011 Nigel Webb

© 2011 Nigel Webb

© 2011 Nigel Webb

© 2011 Nigel Webb tRNA status
1 = no tRNA
2 = tRNA$^{eMet}$
3 = Met-tRNA$^{eMet}$
4 = Cys-tRNA$^{Cys}$ © 2011 Nigel Webb © 2011 Nigel Webb © 2011 Nigel Webb

SEQUENCE LISTING

```
<160> NUMBER OF SEQ ID NOS: 5

<210> SEQ ID NO 1
<211> LENGTH: 42
<212> TYPE: RNA
<213> ORGANISM: artificial
<220> FEATURE:
<223> OTHER INFORMATION: mRNAMet

<400> SEQUENCE: 1
gggaugauga ugaugaugau gaugaugaug cuuucuaggc ac                        42

<210> SEQ ID NO 2
<211> LENGTH: 42
```

```
<212> TYPE: RNA
<213> ORGANISM: artificial
<220> FEATURE:
<223> OTHER INFORMATION: mRNA

<400> SEQUENCE: 2
gggaaggagg uaaaaauguu uuuuuuugc uuuugcuagg ca                    42

<210> SEQ ID NO 3
<211> LENGTH: 48
<212> TYPE: RNA
<213> ORGANISM: artificial
<220> FEATURE:
<223> OTHER INFORMATION: mRNA

<400> SEQUENCE: 3
gggaugauga ugaugaugau gaugaugaug cuuucuaggc acacgaga             48

<210> SEQ ID NO 4
<211> LENGTH: 18
<212> TYPE: DNA
<213> ORGANISM: artificial
<220> FEATURE:
<223> OTHER INFORMATION: a complementary DNA oligonucleotide linked to
      desthiobiotin

<400> SEQUENCE: 4
tctcgtgtgc ctagaaag                                              18

<210> SEQ ID NO 5
<211> LENGTH: 42
<212> TYPE: RNA
<213> ORGANISM: artificial
<220> FEATURE:
<223> OTHER INFORMATION: RNA containing Shine-Dalgarno sequence

<400> SEQUENCE: 5
gggaaggagg uaaaaauguu uuuuuuugc uuuugcuagg ca                    42
```

NUCLIONS AND RIBOCAPSIDS

CROSS-REFERENCE TO RELATED APPLICATIONS

The present application claims priority under 35 U.S.C. § 119(e) to U.S. provisional patent application U.S. Ser. No. 61/411,974 filed on Nov. 10, 2010. The subject matter in this provisional patent application not disclosed in the present application is hereby expressly abandoned upon the filing of the present application.

FEDERALLY SPONSORED RESEARCH

None

SEQUENCE LISTING

A computer readable text file, entitled 'SequenceListing.txt,' created on or about Oct. 31, 2011 with a file size of about 1.13 kb contains the sequence listing for this application and is hereby incorporated by reference in its entirety.

COPYRIGHT NOTICE

A portion of the disclosure of this patent document contains material which is subject to copyright protection. The owner of the copyright has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

This invention relates to the discovery that certain natural ribonucleic acids form a polymeric shell, called a ribocapsid, around another nucleic acid, forming a biological structure called a nuclion. Transfer RNA ('tRNA') molecules form such nuclions when they bind to each other and messenger RNA ('mRNA') without the participation of a ribosome. These tRNA nuclions qualify and protect the mRNA, flag translation start codons, ensure frame registration, warehouse charged tRNAs, and accelerate protein synthesis. Abnormal nuclions and ribocapsids may cause several human diseases and disorders. For example, mutations in the tRNA sites which bind adjacent tRNAs in a ribocapsid are associated with cellular transformations implicated in certain types of cancer. Retroviruses such as HIV form tRNA primer structures which mimic legal nuclions, presumably to hijack the host cell's protein synthesis machinery.

The pharmaceutical and biotechnology industries are in urgent need of new biological targets for the development of novel diagnostic, therapeutic and prophylactic products for the treatment of human diseases and disorders. Several embodiments of this invention directly address this need by providing isolated nuclions for use in pharmaceutical research and development. Nuclions play a key role in all protein synthesis in humans, and, as such, represent prime candidates for medical intervention. Several embodiments define specific nuclion targets for the development of drugs for the treatment of nuclion-mediated diseases and disorders, including but not limited to certain cancers and viral infections. Other embodiments teach methods for the manufacture of isolated nuclions for use by researchers and others in the pharmaceutical and biotechnology industries.

SUMMARY OF THE INVENTION

The invention relates to an isolated nuclion comprising (i) a core nucleic acid, and (ii) one or more ribocapsids each comprising a polymer of two or more ribocapsid subunits, wherein said ribocapsid subunits comprise nucleic acid. In further embodiments, (a) most of the ribocapsid subunits are bound to at least a part of the core nucleic acid, and (b) most of the ribocapsid subunits are bound to at least a part of one or more adjacent ribocapsid subunits. In further embodiments, the nuclion additionally comprises one or more nuclion envelopes, where at least one of the nuclion envelopes is optionally bound to at least a part of (a) the basic nuclion part of the nuclion, (b) a core nucleic acid, (c) one or more of the ribocapsids, (d) one or more of the ribocapsid subunits, (e) another nuclion envelope of the nuclion, or (f) any combination of the foregoing. In yet further embodiments, one or more of the ribocapsid subunits comprises RNA, for example, transfer RNA. In additional embodiments, one or more of the ribocapsid subunits comprises initiator transfer RNA and one or more of the ribocapsid subunits comprises elongator transfer RNA. In yet additional embodiments, the nuclion is a mimic or counterfeit of a normal nuclion, and said nuclion is a nuclion-like composition associated with a cellular organism, an adventitious agent, a virus, a retrovirus, a retroviral tRNA primer complex, a human immunodeficiency virus tRNA primer complex, any other natural source of a nuclion mimic or any non-natural source of a nuclion mimic.

In one aspect, the core nucleic acid comprises DNA. In another aspect, the core nucleic acid comprises RNA, for example, messenger RNA. In another aspect, one or more ribocapsid subunits are bound to said mRNA at or near a start codon. In another aspect, one or more ribocapsid subunits are additionally bound to a part of a protein synthesis marker sequence in said mRNA, wherein such marker sequence is optionally a Shine-Dalgarno sequence or a Kozak sequence. In another aspect, one or more nuclion components of the nuclion, such as mRNA, is additionally bound to at least a part of a ribosome. In another aspect, the isolated nuclion is an initiation nuclion, wherein (i) the core nucleic acid comprises mRNA and (ii) at least a part of said mRNA comprises a ribocapsid and/or ribocapsid subunit binding sequence operably linked to the start codon in said mRNA.

The invention also relates to a method for manufacturing an isolated nuclion by bringing into association with each other two or more nuclion components. In one aspect, the nuclion is manufactured by bringing into association a combination of nuclion components, wherein such combination is selected from the group consisting of (i) a core nucleic acid and two or more ribocapsid subunits, (ii) a core nucleic acid, two or more ribocapsid subunits, and one or more predefined nuclion envelopes, (iii) a basic nuclion and one or more predefined nuclion envelopes, (iv) a core nucleic acid and two or more tRNA ribocapsid subunits, (v) a core nucleic acid, two or more tRNA ribocapsid subunits, and one or more predefined nuclion envelopes, (vi) a basic tRNA nuclion and one or more predefined nuclion envelopes, (vii) an enveloped nuclion and one or more predefined nuclion envelopes, (viii) a combination of any two or more members of this group, and (ix) a hybrid of two or more members of this group. In another aspect, the method is selected from the group consisting of (1) combining a core nucleic acid preparation with one or more ribocapsid subunit preparations, (2) adding one or more core nucleic acid preparations to a ribocapsid subunit preparation, (3) adding one or more ribocapsid subunit preparations to a core nucleic acid preparation, (4) combining a preparation of core nucleic acid immobilized directly or indirectly on a solid phase with one or more preparations of ribocapsid subunits that are not immobilized, (5) combining one or more preparations of ribocapsid subunits immobilized directly or indirectly on a solid phase with a preparation of core nucleic acid that is not immobilized, (6) combining a preparation of core nucleic acid immobilized directly or indirectly on a solid phase with one or more preparations of ribocapsid subunits immobilized directly or indirectly on a solid phase, (7) combining a core nucleic acid preparation with one or more ribocapsid subunit preparations using a batch process, (8) combining a core nucleic acid preparation with one or more ribocapsid subunit preparations using a continuous process, (9) combining a core nucleic acid preparation with one or more ribocapsid subunit preparations then mixing the combination, (10) combining a core nucleic acid preparation with one or more ribocapsid subunit preparations then separating the resulting nuclions from the core nucleic acid not in nuclions, (11) combining a core nucleic acid preparation with one or more ribocapsid subunit preparations then separating the resulting nuclions from the ribocapsid subunits not in nuclions, (12) combining a core nucleic acid preparation with one or more ribocapsid subunit preparations then separating the resulting nuclions from both the core nucleic acid not in nuclions and the ribocapsid subunits not in nuclions, (13) combining a basic nuclion preparation with one or more nuclion envelope preparations, (14) adding one or more basic nuclion preparations to a nuclion envelope preparation, (15) adding one or more basic nuclion envelope preparations to a nuclion preparation, (16) combining a preparation containing basic nuclions immobilized directly or indirectly on a solid phase with one or more preparations containing nuclion envelopes that are not immobilized, (17) combining one or more preparations containing nuclion envelopes immobilized directly or indirectly on a solid phase with a preparation containing basic nuclions that are not immobilized, (18) combining one or more preparations containing basic nuclions immobilized directly or indirectly on a solid phase with a one or more preparations containing nuclion envelopes immobilized directly or indirectly on a solid phase, (19) combining one or more basic nuclion preparations with one or more nuclion envelope preparations using a batch process, (20) combining one or more basic nuclion preparations with one or more nuclion envelope preparations using a continuous process, (21) combining one or more basic nuclion preparations with one or more nuclion envelope preparations then mixing the combination, (22) combining one or more basic nuclion preparations with one or more nuclion envelope preparations then separating the resulting enveloped nuclions from the nuclions not in enveloped nuclions, (23) combining one or more basic nuclion preparations with one or more nuclion envelope preparations then separating the resulting enveloped nuclions from the nuclion envelopes not in enveloped nuclions, (24) combining one or more basic nuclion preparations with one or more nuclion envelope preparations then separating the resulting enveloped nuclions from both the basic nuclions not in enveloped nuclions and the nuclion envelopes not in enveloped nuclions, (25) combining one or more core nucleic acid preparations with one or more ribocapsid unit preparations and one or more nuclion envelope preparations, (26) combining one or more core nucleic acid preparations with one or more ribocapsid unit preparations and one or more nuclion envelope preparations then mixing the combination, (27) combining one or more core nucleic acid preparations with one or more ribocapsid unit preparations and one or more nuclion envelope preparations then separating the resulting enveloped nuclions from the resulting combination, (28) combining one or more core nucleic acid preparations with one or more ribocapsid unit preparations and one or more nuclion envelope preparations in a batch process, (29) combining one or more core nucleic acid preparations with one or more ribocapsid unit preparations and one or more nuclion envelope preparations in a continuous process, (30) a combination of any two or more members of this group, and (31) a hybrid of any two or more members of this group.

In another aspect, the method further comprises one or more steps selected from the group consisting of (1) employing a molar ratio of ribocapsid subunits to core nucleic acid in excess of approximately 1, 2, 5, 10, 20, 30, 40, 50, 60, 70, 80, 90, 100, 200, 300, 400, 500, 600, 700, 800, 900 or 1000; (2) including magnesium chloride, magnesium ions, or magnesium salts at a solution concentration in excess of approximately 1, 2, 5, 10, 20, 30, 40, 50, 60, 70, 80, 90, 100, 200, 300, 400, 500, 600, 700, 800, 900 or 1000 millimoles per liter; (3) omitting polyamines from all solutions and preparations; (4) ensuring that all solutions and preparations are free of nucleases; (5) ensuring that all solutions, equipment, supports, disposables, supplies and other items which contact the reactants or product are substantially free of ribonucleases; (6) employing one or more ribonuclease inhibitors that do not interfere with nuclion assembly or product integrity; (7) allowing sufficient time for assembly wherein said time exceeds 0.1, 1, 5, 10, 20, 30, 40, 50, 60, 120, 180, 240 or 300 seconds, (8) employing a non-denaturing assembly environment, (9) conducting assembly activities at a temperature below approximately 0, 4, 8, 10, 15, 20, 25, 30, 35, 37, 40, 45, 50, 55 or 60 degrees Celsius (° C.); (10) chemically cross-linking one or more nuclion components; (11) any combination of two or more of the members of this group, and (12) any hybrid of two or more members of this group.

In another aspect, the method further comprises isolating the nuclion by one or more steps selected from the group consisting of separation based on size, separation based on shape, separation based on mass, separation based on chemical affinity, separation based on immunological properties, separation based on electrical properties, separation using a biotin moiety bound to a nuclion component, separation using a nucleic acid probe bound to a nuclion component, separation based on osmotic properties, separation based on magnetic properties, separation based on solubility, separation based on electrophoresis in a non-denaturing gel, fractionation of bands following separation in a non-denaturing gel, filtration, dialysis, gel exclusion chromatography, ion exchange chromatography, and a combination of any two or more members of this group. In another aspect, the method further comprises stabilizing the nuclion, during or following manufacture, by one or more steps selected from the group consisting of chemical modification, physical modification, cross-linking, cross-linking a nuclion component, cross-linking two or more nuclion components, introduction of a covalent linkage between two or more bases on separate strands of nucleic acid, exposure to a bifunctional nitrogen mustard, exposure to cis-diaminodichloroplatinum, exposure to formaldehyde, exposure to a psoralen, exposure to 4,5',8-trimethylpsoralen, exposure to 8-methoxypsoralen, exposure to 4-aminomethyl-4,5',8-trimethylpsoralen, freeze-drying, freezing, drying, cooling, addition of a scavenger, addition of an anti-oxidant, addition of a sequestrant, addition of an emulsifier, addition of an excipient, addition of a surfactant, addition of an ultraviolet stabilizer, addition of a ribonuclease inhibitor, and a combination or any two or more members of this group.

BRIEF DESCRIPTION OF THE DRAWINGS

Color Drawings

The file of this patent contains at least one color drawing. Copies of the patent with color drawings will be provided by the PTO upon payment of the necessary fee.

FIG. 3A is a schematic presentation of the most conserved tRNA nucleosides in the format of a consensus tRNA secondary structure, where the nucleoside location numbering follows the convention adopted by the authors of the tRNAdb database. Dotted lines indicate canonical base-pairing and arrows indicate stacking of (i) the amino acid stem (1-7; 66-72) with the pseudouridine stem (49-53; 61-65), and (ii) the anticodon stem (27-31; 39-43) with the dihydrouridine stem (10-13; 22-25). Other marked tRNA structural elements include the amino acid binding site ('aa' within a circle next to 76), the pseudouridine loop (54-60), the anticodon loop (32-38) containing the anticodon (34-36 within the green box), the dihydrouridine loop (14-21) and the variable loop (44-47). The seventy six locations labeled 1-76 are usually occupied by a nucleotide and marked O (for occupied), unless otherwise marked for prevalence (see below). In contrast, twenty-three locations (0, 17a, 20a, 20b, e1-5, e11-17 and e21-27) are not usually occupied and marked E (for extra). Yellow boxes indicate locations where one nucleoside group (G, A, C or U, together with any modifications thereof) has a sequence prevalence (SP) of 90% or more within these 623 sequences. The letters in regular or italic type within such yellow boxes indicate, respectively, (i) the nucleoside group with an SP of more than 90% at that location (G, A, C or U) or (ii) the modified nucleoside with an SP of more than 50% at that location (P or T). Blue boxes indicate locations where the nucleoside class (purine or pyrimidine) has an SP of 90% of more. The letters in regular or italic type within such nucleoside class boxes indicate, respectively, (i) the nucleoside class with an SP of more than 90% at that location (R for purine, Y for pyrimidine) or (ii) the modified nucleoside with an SP of more than 50% at that location (H for modified adenosine). The D at location 20 indicates dihydrouridine with an SP of more than 50% at that location.

FIG. 3B is a table of the sequence prevalence symbols and nucleoside abbreviations used in FIG. 3A. Certain nucleosides are marked with an asterisk to indicate that the related data refers to both the basic and the modified forms of such nucleosides.

FIG. 4A is a computer modeling overlay of ten reported tRNA structures (determined by X-ray diffraction studies of tRNA crystals) viewed from the right side of the molecules and prepared using PyMOL software to illustrate the locations of the phosphodiester backbones and their attached nucleosides.

FIG. 4B is a view from the side of the tRNAs distal to the amino acid site of the same structures as those presented in FIG. 4A.

FIG. 4C provides the color key and other information for the structures presented in FIG. 4A and FIG. 4B. The column marked AA indicates the amino acid specificity of each tRNA. The column marked PDB gives the reference to the structure entry in the Protein Data Bank, from which the data was derived and in which the study investigators are cited.

FIG. 5A is a nucleoside prevalence topogram for transfer RNA which reports the results of data mining in 623 reported tRNA sequences for nucleosides with a sequence prevalence of 90% or more, presented on a PyMOL-generated computer model of the tertiary structure of yeast tRNA$^{Phe}$. Space-filling representations of all component atoms (except hydrogen) are employed. Four conservation zones are identified.

FIG. 5B provides the color key to the nucleotides in FIG. 5A using the abbreviations defined in FIG. 3B.

FIG. 7A is a computer modeling overlay of nine TLS nucleosides from the ten reported tRNA structures shown in FIG. 4A and FIG. 4B, but using a stick representation of the nucleosides. The TLS is viewed from the top of the tRNA molecule, with the anticodon stem in the z direction (away from the viewer) and the amino acid stem in the y direction (towards the top of the page).

FIG. 7B provides the color key and other information for the structures presented in FIG. 7A. The column marked AA indicates the amino acid specificity of each tRNA. The column marked PDB gives the reference to the structure entry in the Protein Data Bank, from which the data was derived and in which the study investigators are cited.

FIG. 8A is a computer model of two aminoacylated L-conformation yeast tRNA$^{Phe}$ molecules (marked tRNA1 and tRNA2) bound to adjacent codons on mRNA within a T-form nuclion. The dashed line is the nuclion axis, marked 5' and 3' to indicate the mRNA direction.

FIG. 8B provides the color key to the nucleotides in FIG. 8A using the abbreviations defined in FIG. 3B.

FIG. 9A is a computer model of three aminoacylated L-conformation yeast tRNA$^{Phe}$ molecules (marked tRNA1, tRNA2 and tRNA3) bound to consecutive codons on mRNA within a T-form nuclion, when viewed on the nuclion axis from the 5' direction.

FIG. 9B provides the color key to the nucleotides in FIG. 9A using the abbreviations defined in FIG. 3B.

FIG. 10A is a computer model of ten aminoacylated L-conformation yeast tRNA$^{Phe}$ molecules bound to consecutive codons on mRNA in a T-form nuclion. The dashed line shows the nuclion axis, marked 5' and 3' to indicate the mRNA direction.

FIG. 10B provides the color key to the nucleotides in FIG. 10A using the abbreviations defined in FIG. 3B.

FIG. 12A is a computer model of the K-conformation of the anticodon loop in a tRNA, together with a codon to which it is bound, where the anticodon loop and codon are represented by sticks. The anticodon stem in tRNA is represented as mesh. U33 is the conserved GSP90 uridine at position 33. Pu37 is the conserved PSP90 purine at position 37.

FIG. 12B is a computer model of the L-conformation of the anticodon loop in a tRNA, together with a codon to which it is bound, where the anticodon loop and codon are represented by sticks. The anticodon stem in tRNA is represented as mesh. U33 is the conserved GSP90 uridine at position 33. Pu37 is the conserved PSP90 purine at position 37

FIG. 13A is a computer model of four aminoacylated K-conformation yeast tRNA$^{Phe}$ molecules (marked tRNA1, tRNA2, tRNA3 and tRNA4) bound to adjacent codons on mRNA within a S-form nuclion. The dashed line is the nuclion axis, marked 5' and 3' to indicate the mRNA direction.

FIG. 13B provides the color key to the nucleotides in FIG. 13A using the abbreviations defined in FIG. 3B.

FIG. 14A is a computer model of an L-conformation yeast tRNA$^{Phe}$ molecule bound as an R-conformation nuclion cap to a codon on mRNA. The anticodons of several downstream tRNAs are shown (together with their matching codons), but not the balance of these molecules. The dashed line is the nuclion axis, marked 5' and 3' to indicate the mRNA direction.

FIG. 14B provides the color key to the nucleotides in FIG. 14A using the abbreviations defined in FIG. 3B.

FIG. 15 is a schematic diagram of a compound tRNA nuclion containing eleven aminoacylated tRNA molecules within three nuclion conformations, as identified by the associated information table. The schematic conventions for tRNA are defined in the image displayed in the lower left corner.

FIG. 17 is a table of the properties of the three conformations of tRNA nuclions. The symbol ~ means substantially within range of the indicated numbers.

FIG. 23A is a computer model of a primordial (or abnormal contemporary) tRNA cap (tRNA1) catalyzing peptidyl transfer between the CCA tails of the next two tRNAs bound to mRNA:tRNA2, which holds the growing polypeptide chain (in which only the first amino acid is shown and marked 'Polypeptide'), and tRNA3, which holds the next amino acid (marked 'Amino acid'). The participating nucleotides are stacked in six layers, marked L0 through L5.

FIG. 23B provides the color key to the nucleotides in FIG. 23A using the abbreviations defined in FIG. 3B. The black links with round ends between certain nucleosides indicate some of the inter-molecular interactions which contribute to peptidyl transfer. The columns in the table indicate which nucleosides from the three tRNAs align in the six active site layers marked L0 through L5.

FIG. 24A is a computer model of six nucleosides in levels 3 and 4 of the quaternary complex formed by the participating three tRNAs in the peptidyl transfer center (PTC) of a primordial (or abnormal contemporary) nuclion, when viewed from the direction of the pseudouridine stem in the ribozyme tRNA1. The ellipse marked 'Reaction' highlights the active site where the amino group in aminoacyl tRNA3 attacks the carboxyl group in peptidyl tRNA2. Only the first amino acid in the polypeptide chain is shown.

FIG. 24B shows the peptidyl transfer reaction between the two A76 adenosine nucleotides on tRNA2 and tRNA3, when viewed from above the PTC of a primordial (or abnormal contemporary) nuclion, which transfers the growing polypeptide chain from tRNA2 to tRNA3. The ellipse marked 'Reaction' highlights the active site where the amino group in aminoacyl tRNA3 attacks the carboxyl group in peptidyl tRNA2. Only the first amino acid in the polypeptide chain is shown.

FIG. 24C provides the color key to the nucleotides in FIG. 24A and FIG. 24B using the abbreviations defined in FIG. 3B. The black links with round ends between certain nucleosides indicate inter-molecular interactions in layers L3 and L4 which contribute to peptidyl transfer.

FIG. 25A shows a computer model of the ribosylthymine at position 54 (T54) in the TLS on normal contemporary tRNA (tRNA1). The highlighted methyl group blocks binding of the adenosine at position 76 in the CCA on tRNA2 (not shown).

FIG. 25B provides the color key to the nucleotides in FIG. 25A using the abbreviations defined in FIG. 3B.

FIG. 25C shows a computer model of pseudouridine at position 54 (P54) in the PLS on primordial or abnormal contemporary tRNA (tRNA1) together with the enabled binding of the adenosine at position 76 in the CCA on the adjacent downstream tRNA (tRNA2).

FIG. 25D provides the color key to the nucleotides in FIG. 25C using the abbreviations defined in FIG. 3B. The black link with round ends indicates the inter-molecular base pairing.

FIG. 26 is a table of the control logic for nuclion operations and summarizes the states of the left and right TLS sites, driven in part by the nucleosides at positions 54 and 55 in a first tRNA T(N). The associated and resulting nuclion conditions are presented. T(N−1) refers to the adjacent tRNA immediately upstream of the first tRNA, and T(N+1) refers to the adjacent tRNA immediately downstream of the first tRNA. tRNA(N+2) is the tRNA immediately downstream of tRNA(N+1).

FIG. 27A is a computer model of the spermine binding site from a high-resolution structure reported for yeast tRNA$^{Phe}$, when viewed from the left side of the TLS. The spermine is bound in large part by the ribosylthymine at position 54 (T54) and the pseudouridine at position 55 (P55).

FIG. 27B is the computer model presented in FIG. 27, when viewed from the end of the TLS distal to the amino acid tail.

FIG. 28 is a computer model of 12 EF-Tu molecules (marked E1 through E12) when bound to 12 tRNAs in a T-form nuclion, generating a protein capsid around the nucleic acid nuclion. T12 marks tRNA12 to which E12 is bound. The dashed line is the nuclion axis, marked 5' and 3' to indicate the mRNA direction.

Figure 29:
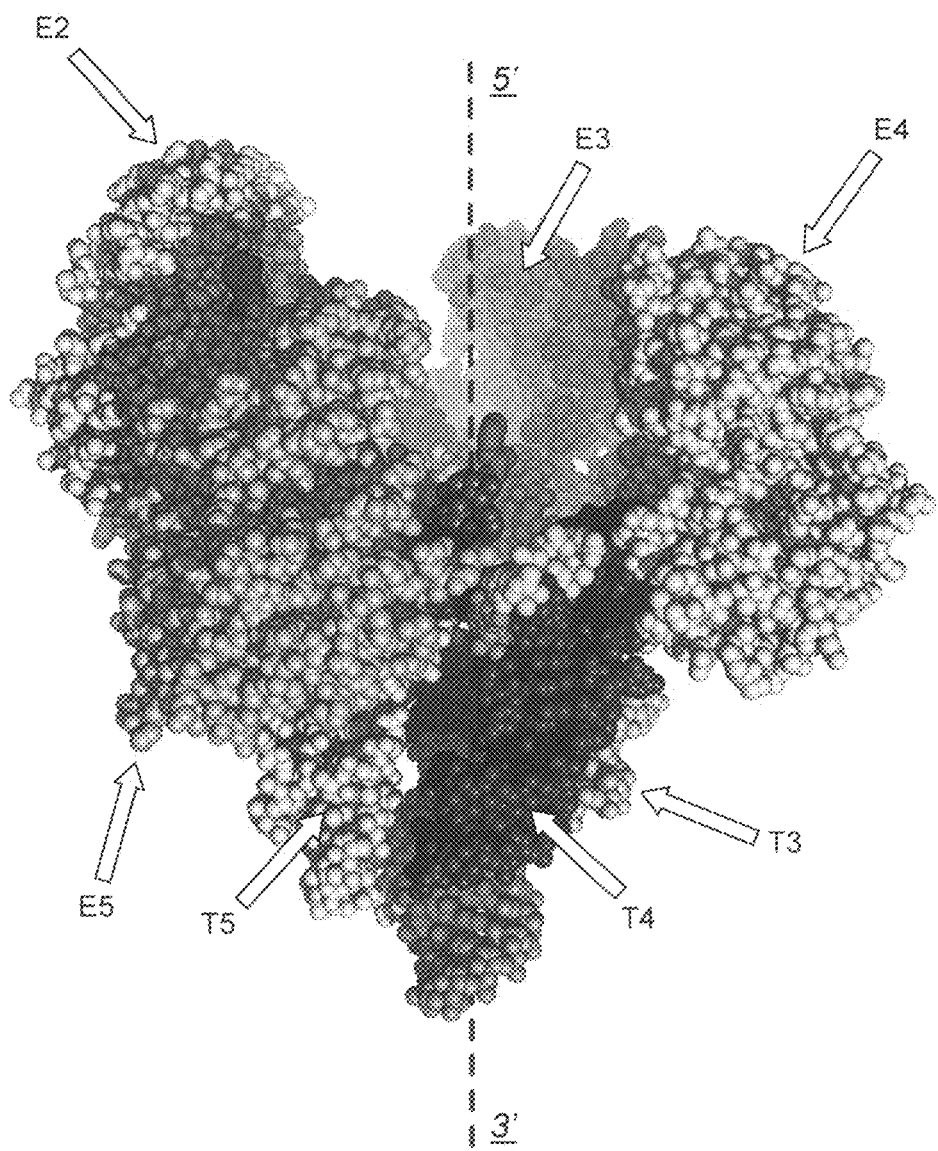

FIG. 29 is a computer model of 4 EF-Tu molecules (marked E1 through E4) bound to four tRNAs in an S-form nuclion. Transfer RNAs 3, 4 and 5 are marked by T3, T4 and T5, respectively. The dashed line is the nuclion axis, marked 5' and 3' to indicate the mRNA direction.

Figure 30A:
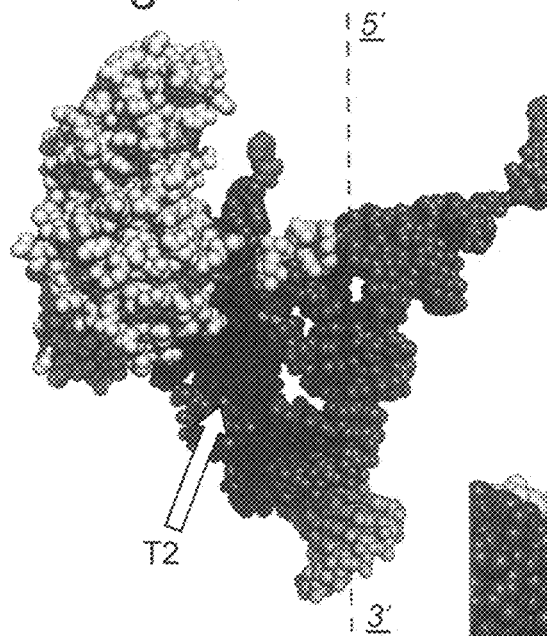

FIG. 30A is a computer model of a pre-binding conformation of EF-Tu aligned with tRNA2 (marked T2) which is bound to the immediate upstream tRNA1. The color key for the tRNA nucleotides is the same as that in FIG. 8B. The dashed line is the nuclion axis, marked 5' and 3' to indicate the mRNA direction.

Figure 30B:
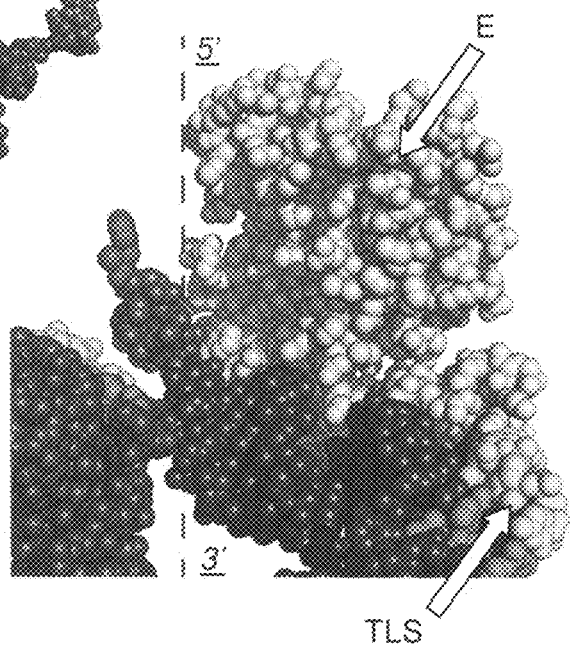

FIG. 30B is a closer view of the computer model shown in FIG. 30A from a different angle. EF-Tu is marked E.

Figure 30C:
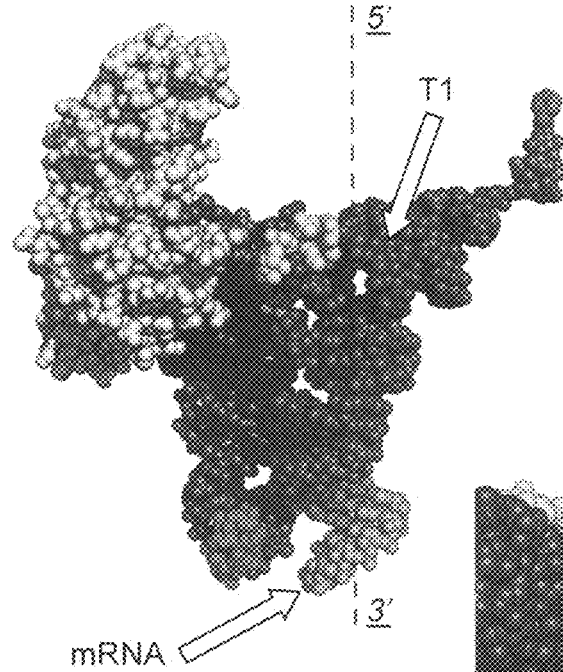

FIG. 30C is a computer model of a post-binding conformation of EF-Tu aligned with tRNA2 which is removed from the immediate upstream tRNA1.

Figure 30D:
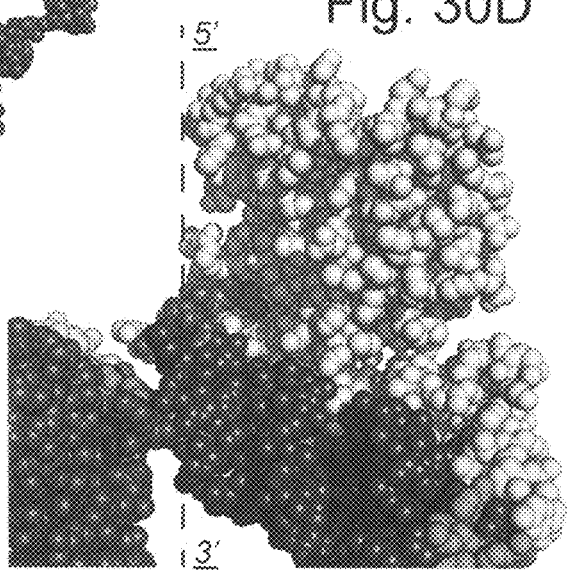

FIG. 30D is a closer view of the computer model shown in FIG. 30C from the same angle as FIG. 30B. tRNA1 is marked T1.

Figure 31A:
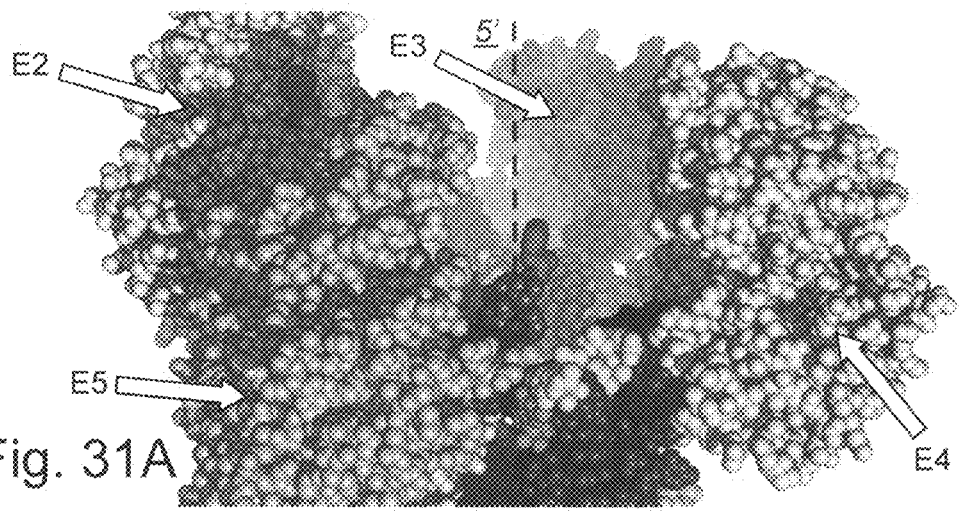

FIG. 31A is a computer model of four EF-Tu molecules (E2 through E5) bound to their four cognate tRNAs in an S-form nuclion. The dashed line is the nuclion axis, marked 5' and 3' to indicate the general mRNA direction.

Figure 31B:
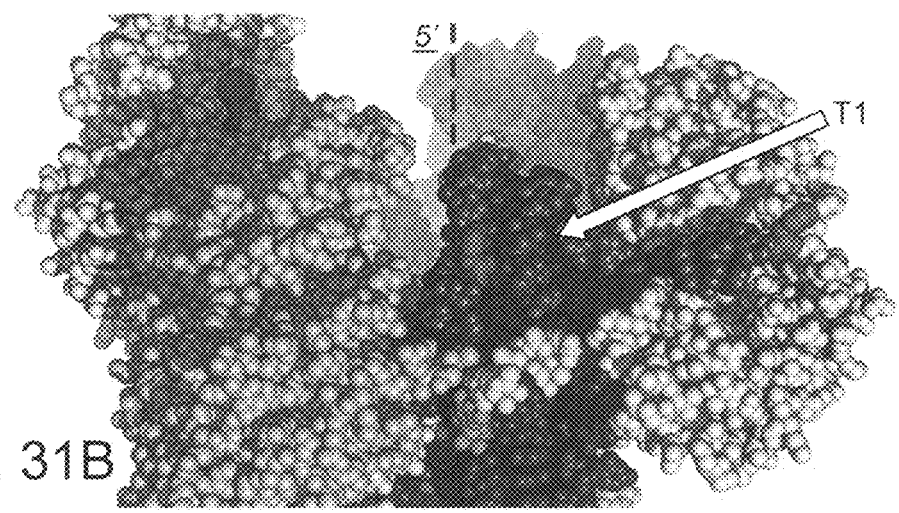

FIG. 31B is a computer model of the molecular structure shown in FIG. 31A when a tRNA cap (T1) is added to the enveloped nuclion. The CCA-amino acid tail from this tRNA cap sits in a cleft on the EF-Tu 4 (E4) attached to tRNA4.

Figure 31C:
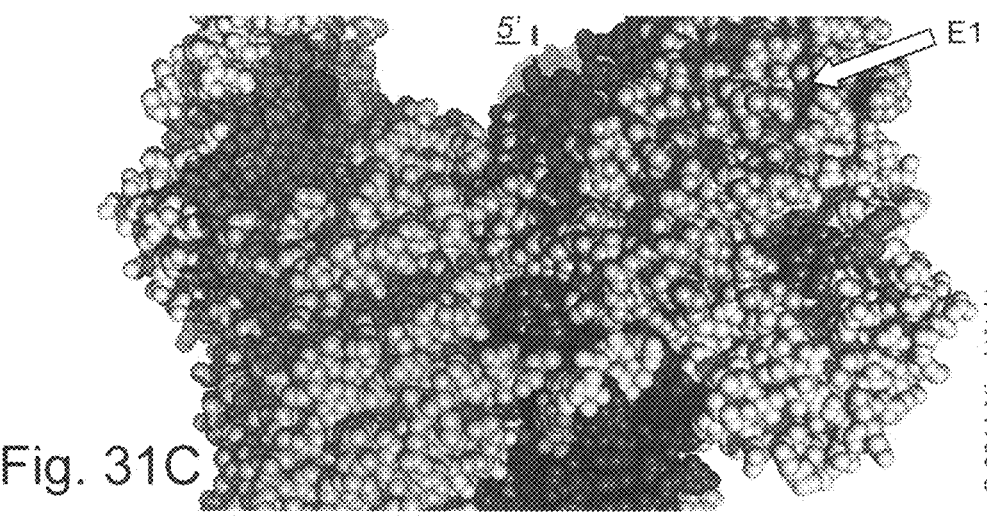

FIG. 31C is a computer model of the molecular structure shown in FIG. 31B when EF-Tu 1 (E1) binds to the tRNA cap T1, which is then sandwiched between EFTu-1 and EFTu-4.

Figure 32A:
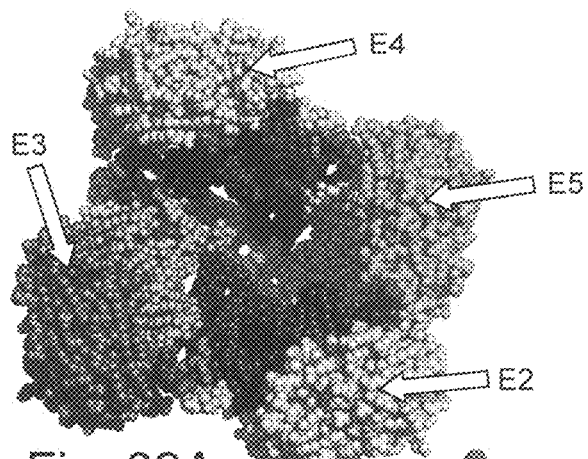

FIG. 32A shows the computer model of FIG. 31A, when viewed from the 5' direction on the nuclion axis. The marking conventions are the same.

Figure 32B:
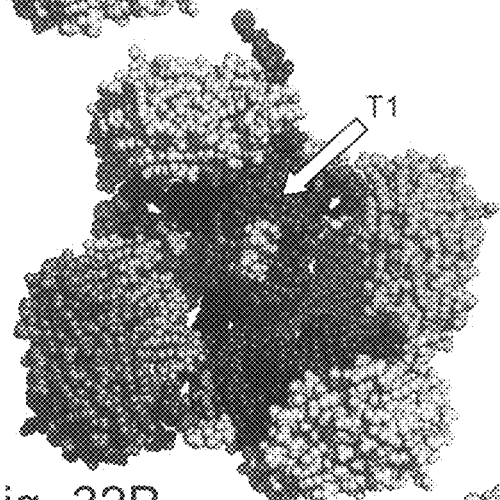

FIG. 32B shows the computer model of FIG. 31B, when viewed from the 5' direction on the nuclion axis. The marking conventions are the same.

Figure 32C:
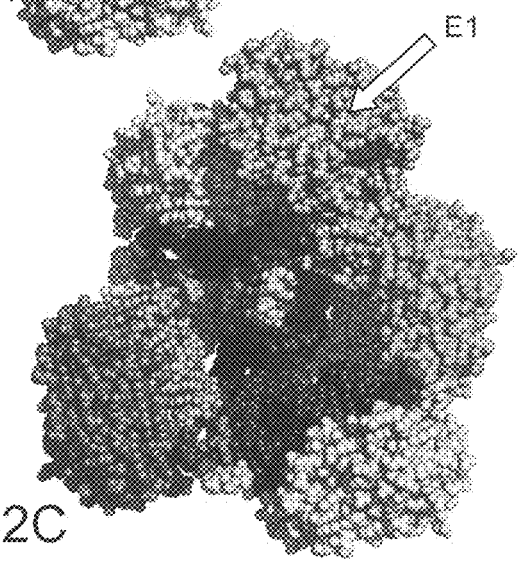

FIG. 32C shows the computer model of FIG. 31C, when viewed from the 5' direction on the nuclion axis. The marking conventions are the same.

Figure 33A:
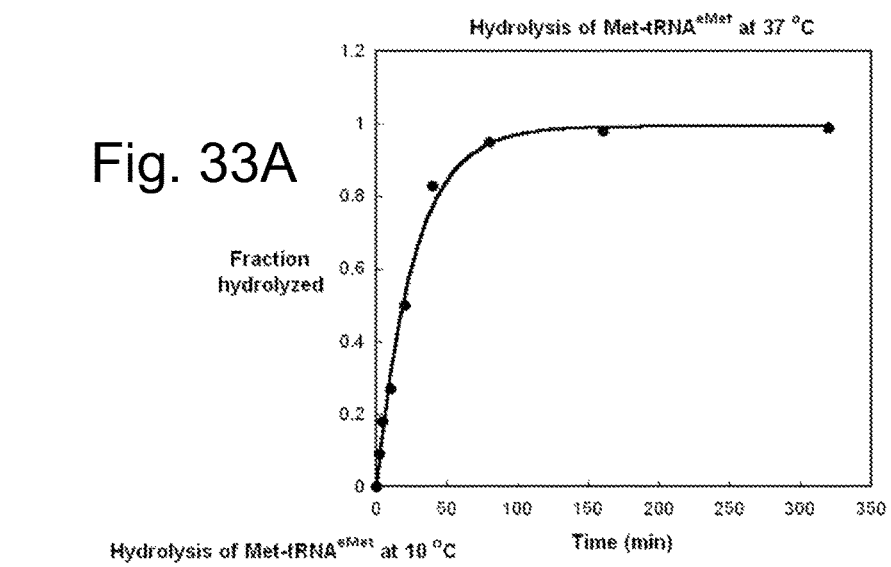

FIG. 33A is a graph showing the fraction (y-axis) of Met-tRNAeMet hydrolyzed with respect to the time in minutes (x-axis) at a temperature of 37° C.

Figure 33B:
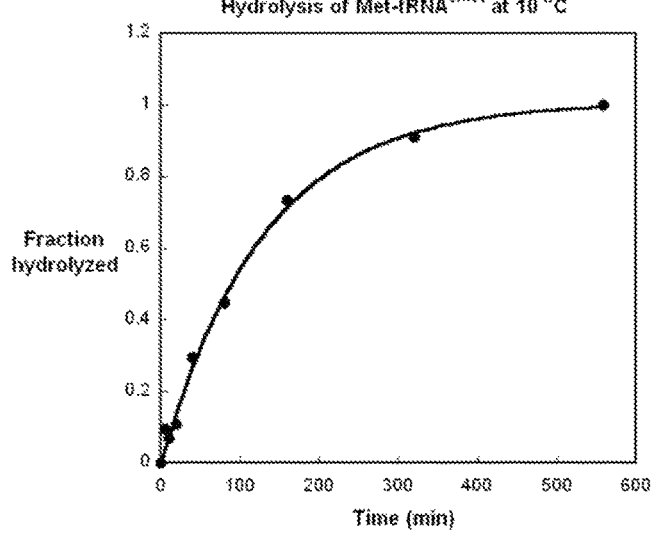

FIG. 33B is a graph showing the fraction (y-axis) of Met-tRNAeMet hydrolyzed with respect to the time in minutes (x-axis) at a temperature of 10° C.

Figure 33C:
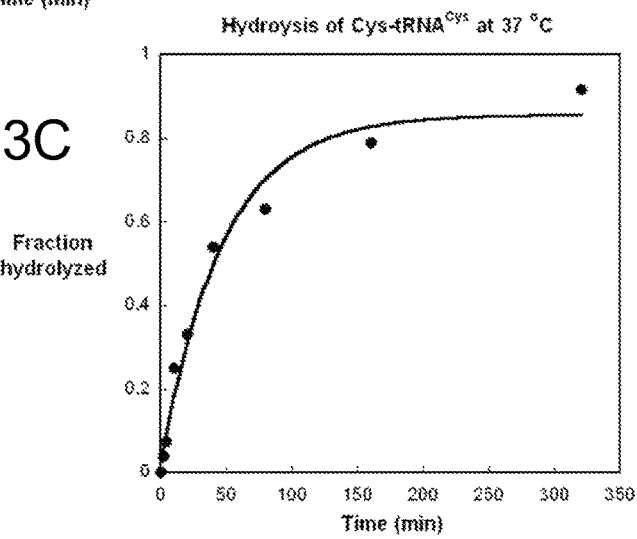

FIG. 33C is a graph showing the fraction (y-axis) of Cys-tRNACys hydrolyzed with respect to the time in minutes (x-axis) at a temperature of 37° C.

Figures 34A, 34B:
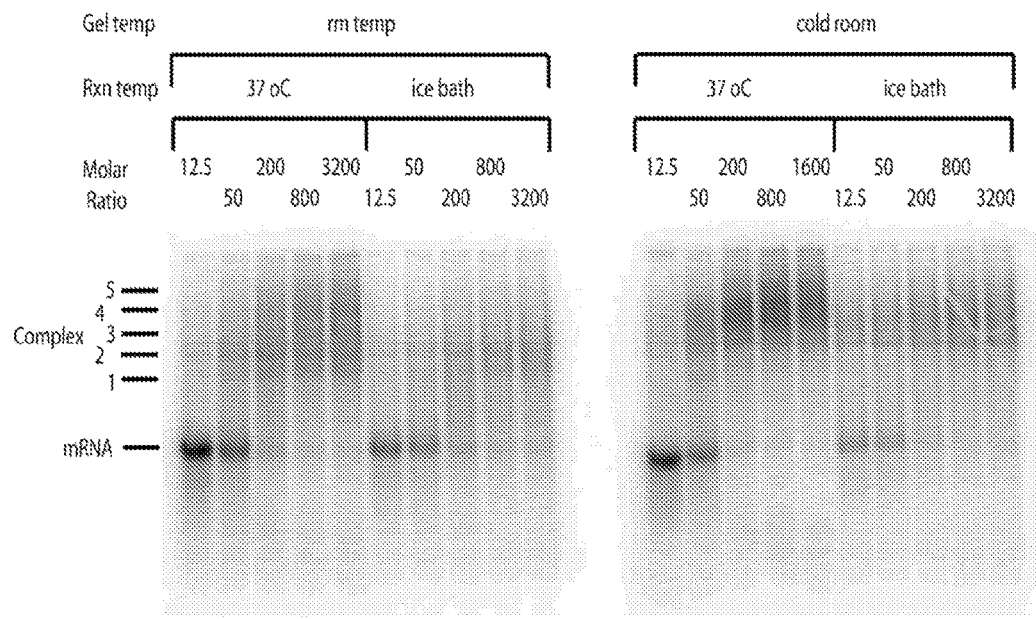

FIG. 34A is a phosphorimage of a non-denaturing gel run at room temperature ('rm temp') to compare the effect of tRNA to mRNA ratio ('Molar Ratio') on nuclion assembly at a reaction temperature ('Rxn temp') of 37 C and in an ice bath. The gel bands associated with mRNA, and nuclion complexes 1 through 5, are marked accordingly.

FIG. 34B is a phosphorimage of a non-denaturing gel run in the cold room to compare the effect of tRNA to mRNA ratio ('Molar Ratio') on nuclion assembly at a reaction temperature ('Rxn temp') of 37 C and in an ice bath.

Figures 34C, 34D:
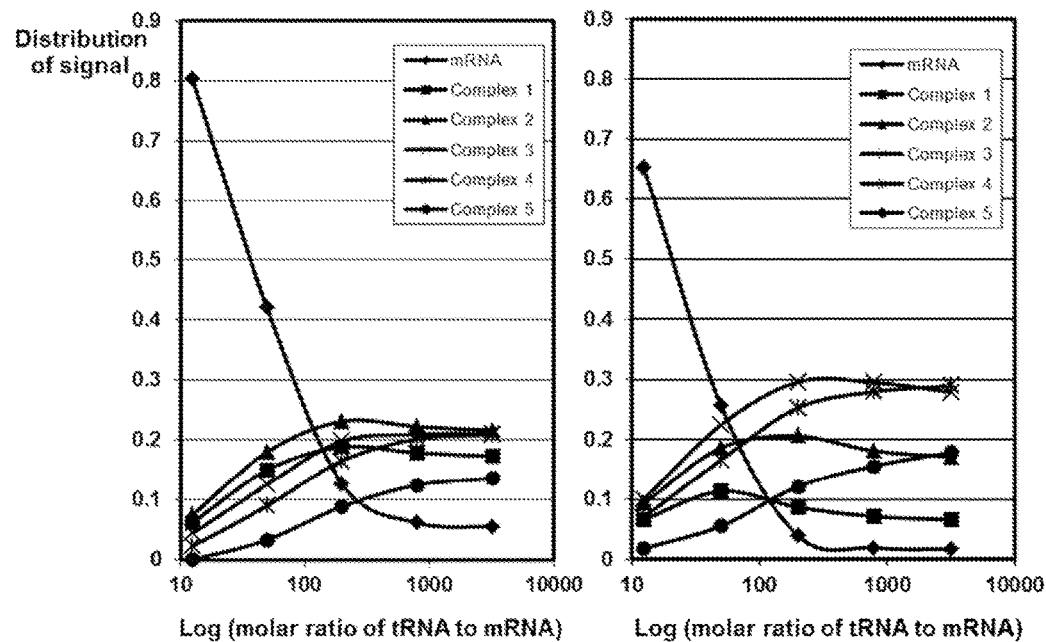

FIG. 34C is a graph derived by quantifying the $^{32}$P-labelled bands corresponding to mRNA and complexes 1-5 in FIG. 34A using Image Quant.

FIG. 34D is a graph derived by quantifying the $^{32}$P-labelled bands corresponding to mRNA and complexes 1-5 in FIG. 34B using ImageQuant.

Figure 35A:
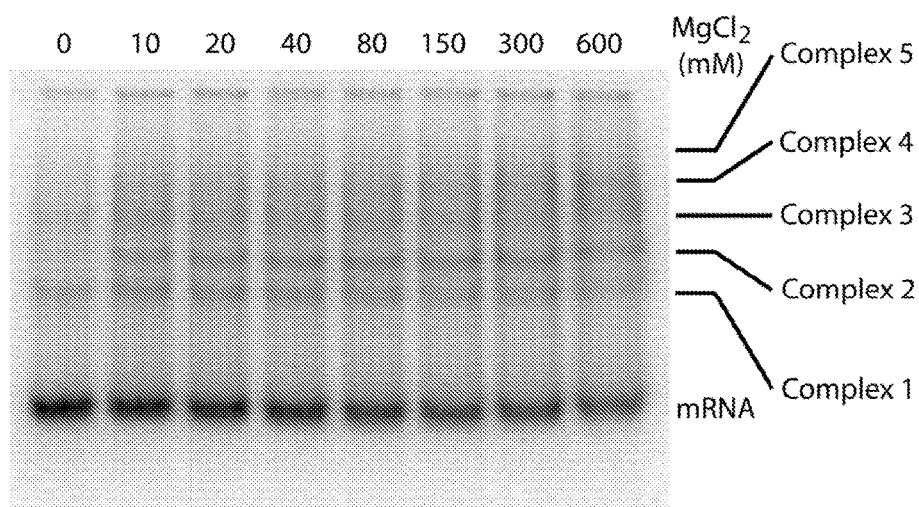

FIG. 35A is a phosphorimage of a non-denaturing gel in a study to determine the effect of magnesium chloride concentration ('MgCl2') on nuclion assembly. The gel bands associated with mRNA, and nuclion complexes 1 through 5, are marked accordingly.

Figures 35B, 35C:
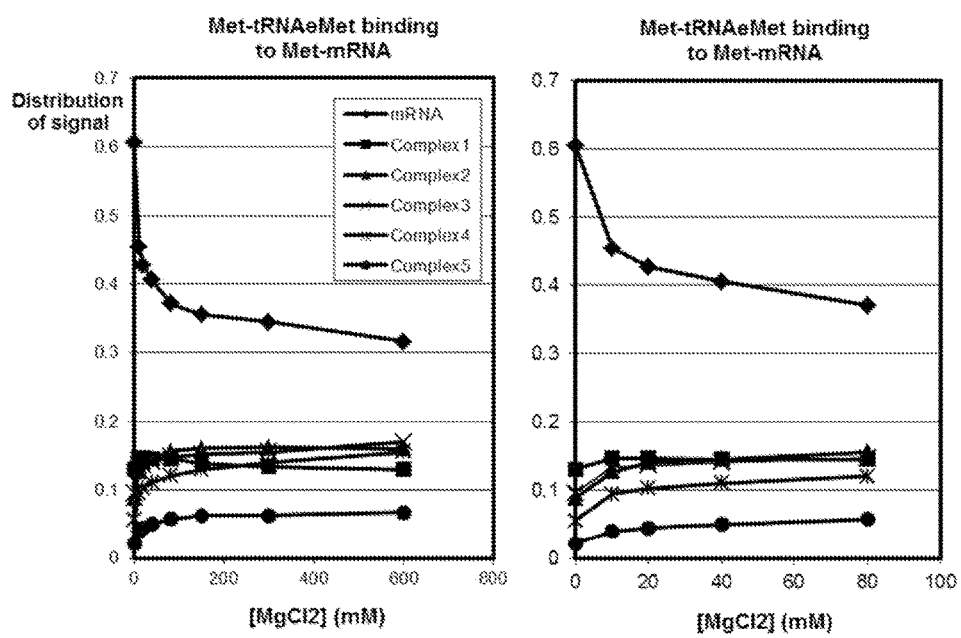

FIG. 35B is a graph derived by quantifying the $^{32}$P-labelled bands corresponding to mRNA and complexes 1-5 in FIG. 35A using ImageQuant.

FIG. 35C is a graph displaying the data from FIG. 35B below a concentration of 100 mM magnesium chloride.

Figure 36:
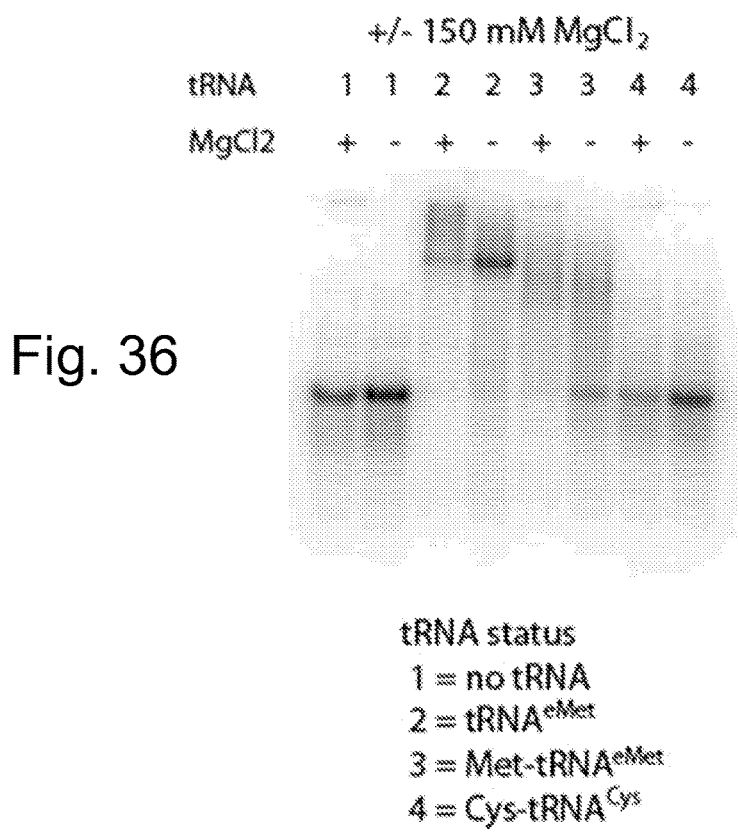

FIG. 36 is a phosphorimage of a non-denaturing gel in a study to determine the effects of aminoacylation status and codon recognition on nuclon assembly in the presence or absence of 150 mM magnesium chloride.

Figure 37:
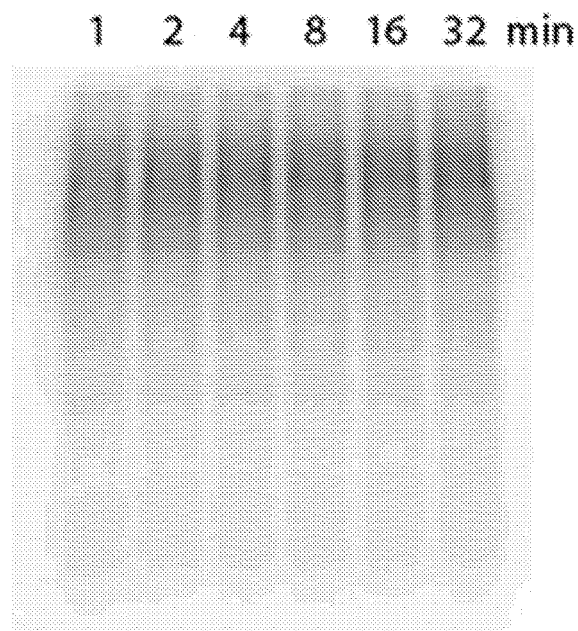

FIG. 37 is a phosphorimage of a non-denaturing gel in a study to determine the time course of nuclon assembly at a tRNA:mRNA molar ratio of 3200 ('min' indicates minutes).

Figure 38A:
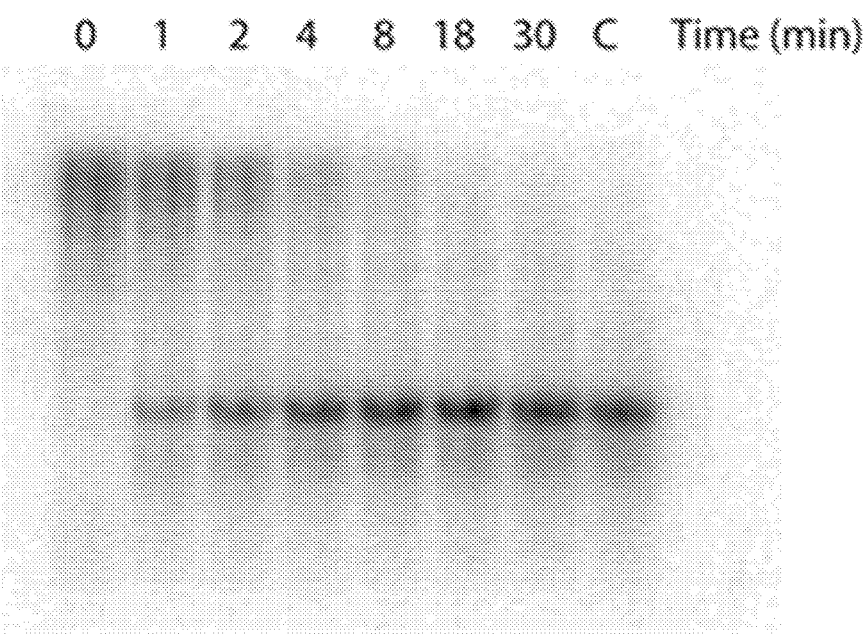

FIG. 38A is a phosphorimage of a non-denaturing gel in a study to determine the time course of nuclon dissociation caused by the addition of competitive mRNA ('min' indicates minutes).

Figure 38B:
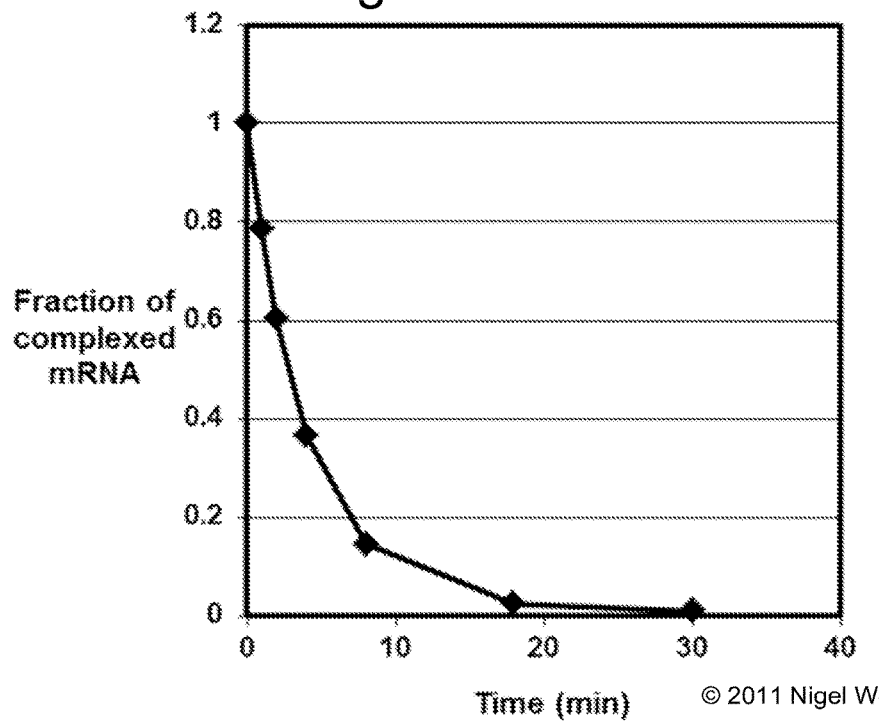

FIG. 38B is a graph derived by quantifying the $^{32}$P-labelled bands corresponding to mRNA and complexes thereof in FIG. 38A using ImageQuant, and calculating the fraction of mRNA complexed in nuclons.

Figure 39A:
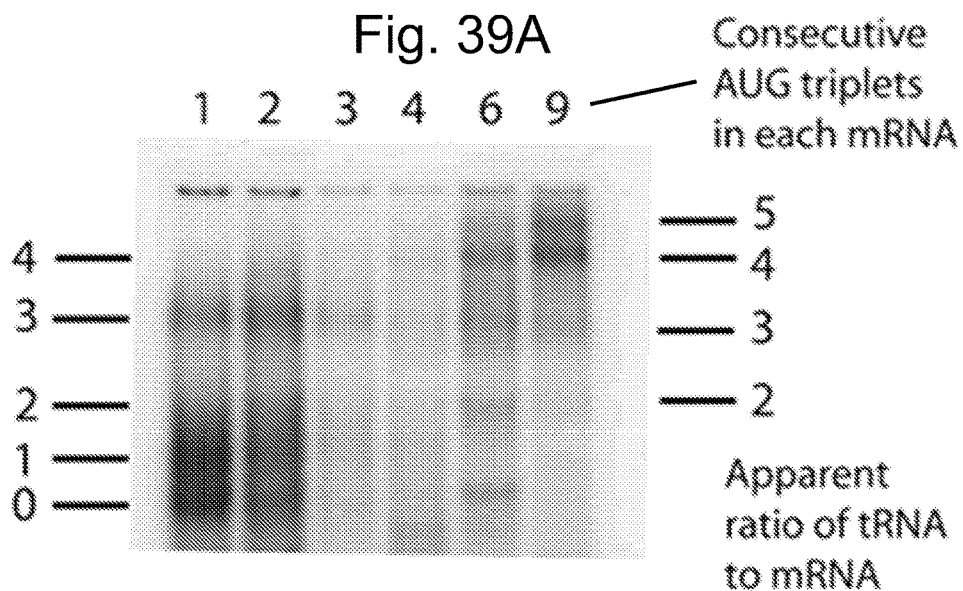

FIG. 39A is a phosphorimage of a non-denaturing gel in a study to determine the molar ratios of tRNA to mRNAs in nuclons, where the mRNA has 1, 2, 3, 4, 6 or 9 AUG codons.

Figure 39B:
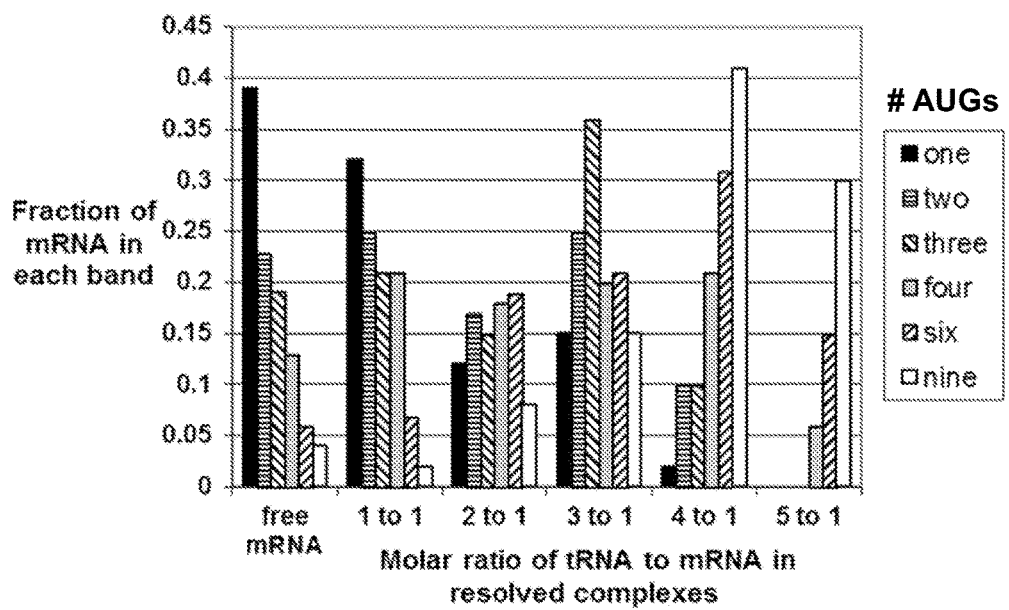

FIG. 39B is a histogram derived by quantifying the $^{32}$P-labelled bands corresponding to mRNA and complexes thereof in FIG. 39A using ImageQuant, and presenting the fraction of mRNA complexed in the respective bands.

Figure 40:
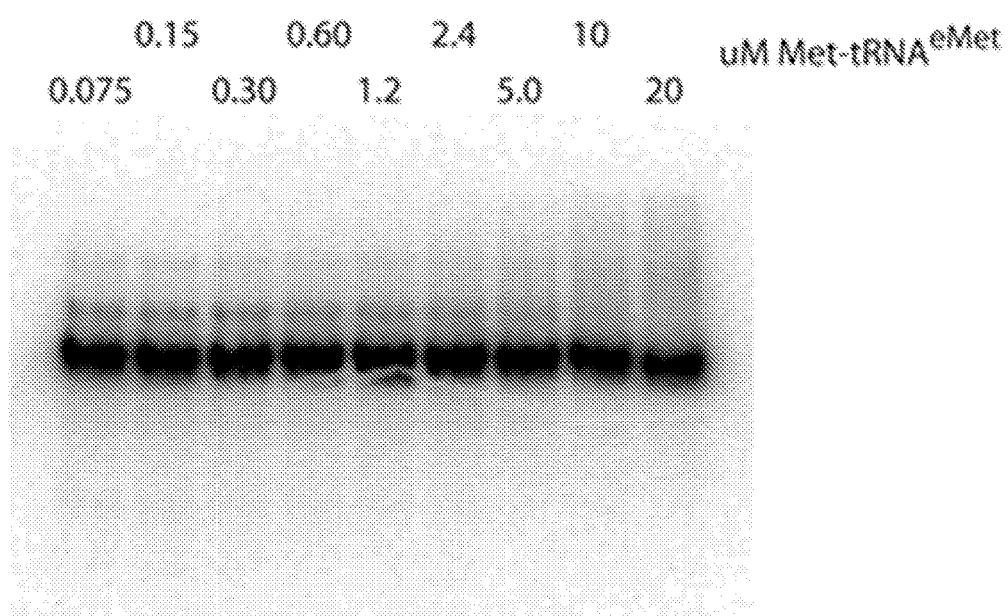

FIG. 40 is a phosphorimage of a non-denaturing gel in a study to determine whether polymeric complexes form with aminoacylated tRNA alone, at concentrations ranging from 0.075 to 20 micromolar ('uM').

Figure 41:
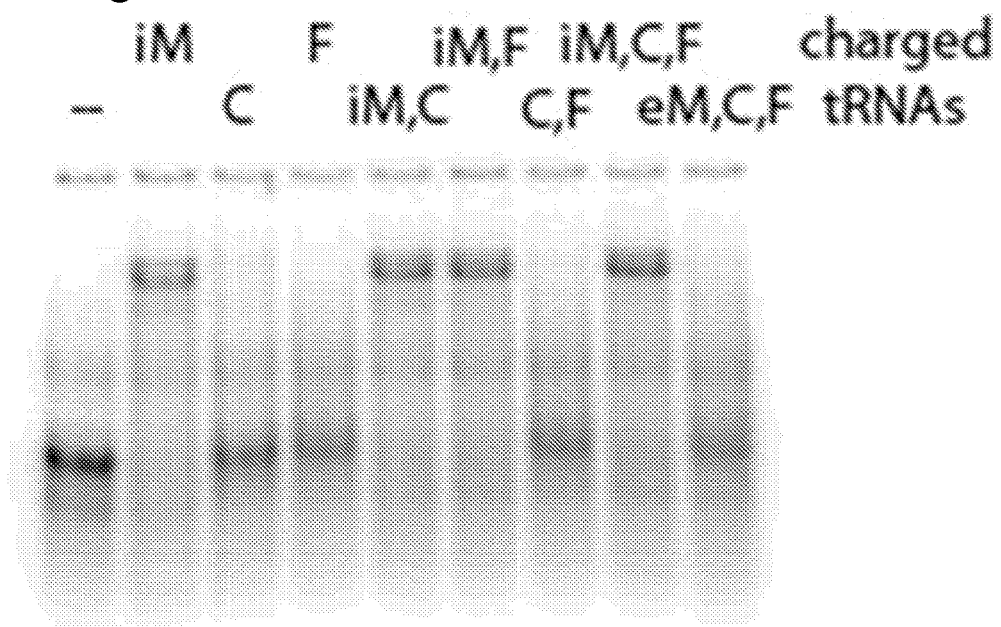

FIG. 41 is a phosphorimage of a non-denaturing gel in a study to determine the binding of various combinations of four aminoacylated tRNAs with an mRNA containing a Shine-Dalgarno sequence upstream of a sequence coding for fMF$_3$CFC. The first lane reflects the results with mRNA alone; the second and subsequent lanes reflect the results with mRNA and one or more aminoacylated tRNAs with specificity marked as follows: C=cysteine, F=phenylalanine, iM=methionine (initiator tRNA), and eM=methionine (elongator tRNA).

Figure 42A:
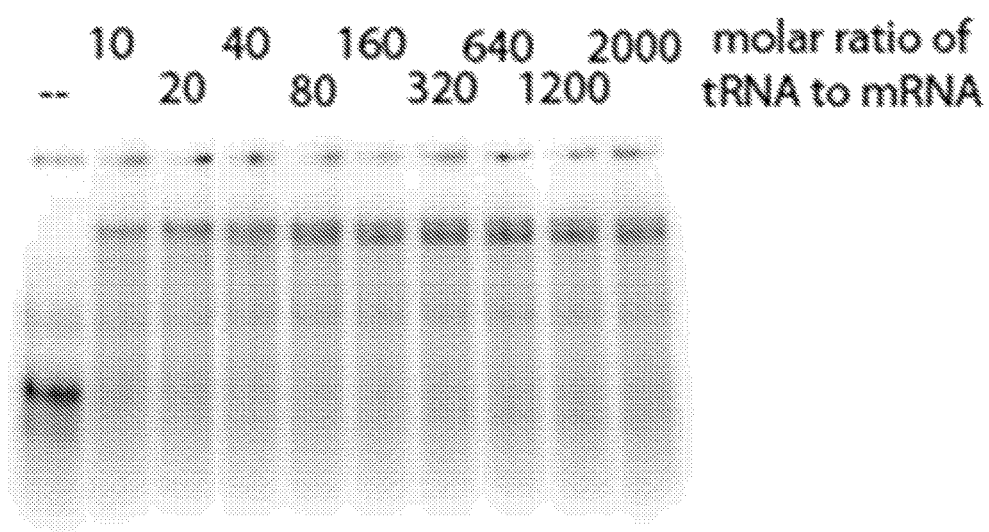

FIG. 42A is a phosphorimage of a non-denaturing gel in a study to measure the effect of the molar ratio of tRNA to mRNA on the extent of nuclon formation, using an mRNA containing a Shine-Dalgarno sequence upstream of a sequence coding for fMF$_3$CFC.

Figure 42B:
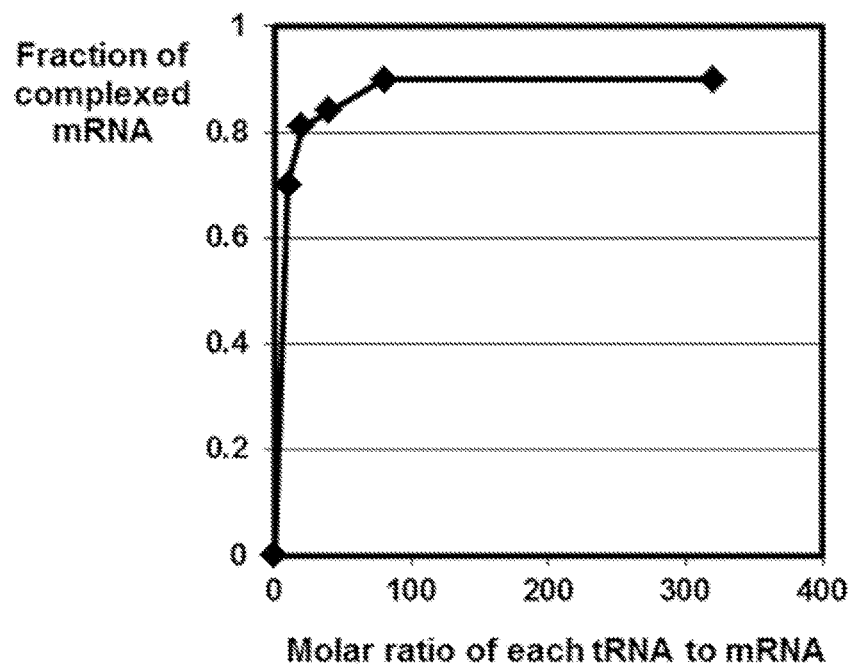

FIG. 42B is a graph derived by quantifying the $^{32}$P-labelled bands corresponding to mRNA and complexes thereof in FIG. 42A using ImageQuant, and calculating the fraction of mRNA complexed in nuclons.

DETAILED DESCRIPTION OF THE INVENTION

Figure 1:
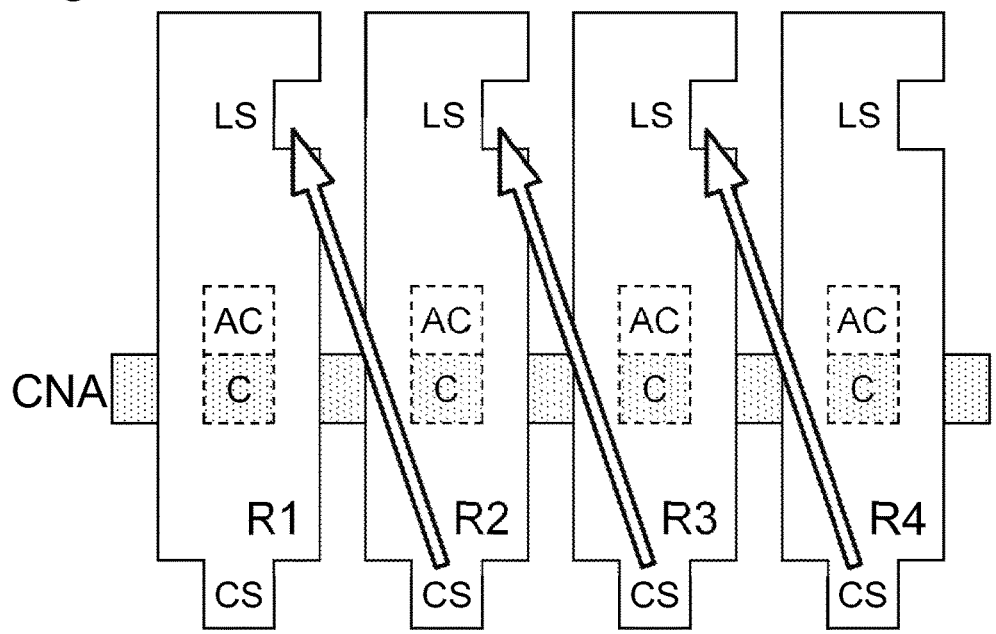
FIG. 1 is a schematic diagram of an example of a nuclion containing four ribocapsid subunits (marked R1 to R4) bound to one core nucleic acid (CNA) molecule. C represents a codon on the CNA. AC represents an anticodon on the ribocapsid nucleic acid. An arrow indicates the binding of a connector site (CS) on one ribocapsid subunit to a link site (LS) on another ribocapsid subunit.

This invention relates to the discovery by the inventors of a biological structure called a nuclon. The schematic diagram in FIG. 1 illustrates some features of a nuclon as taught by several embodiments of this invention. We adopted the word 'nuclon' to parallel the word 'virion', a term used by scientists and physicians to describe an intact virus particle, although most nuclons have attributes which are substantially different from those of most viruses.

The embodiments of this invention introduce a new platform technology based on nuclons and ribocapsids, and teach specific applications of this technology for the pharmaceutical, biotechnology and nanotechnology industries. Several embodiments address (i) compositions of nuclons, ribocapsids, their components and related structures, and (ii) methods for the manufacture, isolation, purification, testing and customization of these compositions, and (iii) industrial applications of nuclon and ribocapsid technology inter alia to identify new molecular targets of medical significance. For example, the nuclons, ribocapsids, their components and related structures described herein have industrial applications to the development of in vitro and in vivo methods for the promotion or inhibition of the translation of a protein from RNA, by modulating the structure or activity of the related natural nuclons. Moreover, the nuclons and related structures defined and synthesized as described herein have industrial applications as an experimental model for an in vitro bioassay to screen for natural nuclon components and other compositions to disrupt the formation of a natural nuclon in vivo and thereby produce a therapeutic, diagnostic or prophylactic result that is medically useful.

In several embodiments of this invention, each nuclon contains a core nucleic acid (CNA), the whole or part of which is bound to one or more oligomeric or polymeric shells of subunits that are mostly nucleic acid. We call the shell of a nuclon a 'ribocapsid' to distinguish this nucleic acid coat from the protein 'capsid' found in viruses. In several embodiments, the ribocapsid subunits (identified as R1 through R4 in FIG. 1) differ in their chemical composition but have sufficient structural homology in order to maintain ribocapsid integrity. In several embodiments, each ribocapsid subunit may contain at least three intermolecular binding sites. Two of these sites, termed the 'connector site' ('CS') and the 'link site' ('LS'), serve to bind adjacent subunits to each other. The third intermolecular site on each ribocapsid subunit is termed an 'anticodon' ('AC'), a nucleotide sequence which binds to a substantially complementary 'codon' ('C') on the core nucleic acid. Codon-anticodon interactions were previously known to those skilled in the art, but the interactions between the connector and link sites on adjacent ribocapsid subunits have not previously been reported.

In several embodiments, the nuclon is stabilized in part by the binding between CS and LS sites on adjacent ribocapsid subunits, at the same time as the anticodons on these molecules bind to their respective codons on the CNA. In several embodiments, the structure and location of these CS and LS sites are sufficiently conserved across different subunits in order to standardize overall ribocapsid geometry, concomitant with certain permitted structural variations within defined regions of the individual subunit molecules. In several embodiments, the CS and LS sites are oriented toward the 3' and 5' directions of the core nucleic acid, respectively. In other embodiments, the CS and LS sites are oriented toward the 5' and 3' directions of the core nucleic acid, respectively. In several embodiments, the nucleotides in the codon and anticodon sites vary routinely (while remaining substantially complementary), to enable the CNA to specifically bind different subunits and perform other biological functions.

Figure 2:
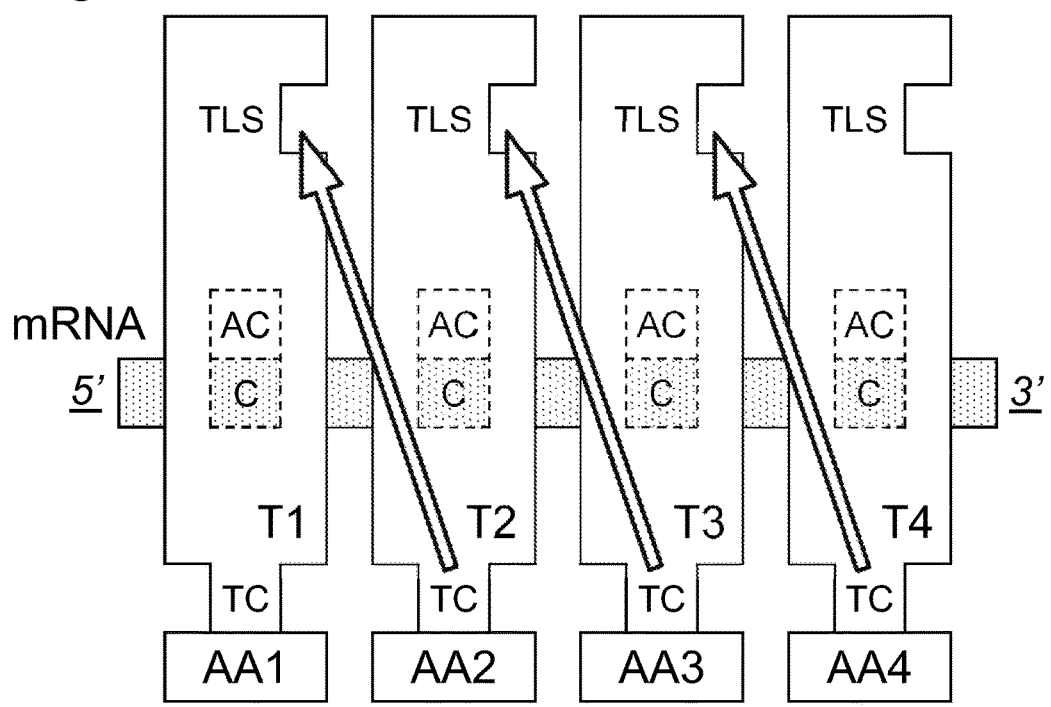
FIG. 2 is a schematic diagram of an example of a tRNA nuclion containing four aminoacylated transfer RNA molecules (marked T1 through T4) bound to one messenger RNA (mRNA) molecule. 5' and 3' mark the direction of the ends of the mRNA. AA1 through AA4 represent the amino acids acylated to the tRNA molecules. C represents a codon on the mRNA. AC represents an anticodon on a tRNA. An arrow indicates the binding of a tRNA connector (TC) on one tRNA to a tRNA link site (TLS) on another tRNA.

In several embodiments, one form of a nuclon is a transfer RNA ('tRNA') nuclon, in which multiple tRNA molecules serve as oligomeric or polymeric subunits to form a tRNA ribocapsid around a messenger RNA molecule, as depicted in the schematic diagram of FIG. 2. The anticodon ('AC') on each ribocapsid tRNA (T1 through T4) may be a sequence of three nucleotides which binds to a codon ('C') of complementary nucleotides on the mRNA in the core of the nuclon. Consecutive tRNA molecules bind to consecutive matching codons on the mRNA. The ribocapsid CS site on each tRNA (termed the 'tRNA connector' or 'TC') is its 'CCA tail' (the sequence of three nucleotides on the 3' end of the tRNA molecule), which may or may not be attached (usually by acylation) to an amino acid ('aminoacylated'). The ribocapsid LS site in tRNA (termed the 'tRNA link site' or 'TLS') is located on the tRNA elbow formed by intramolecular interaction between the pseudouridine and dihydrouridine loops. The TC on one tRNA may connect with the TLS on the adjacent tRNA bound to mRNA in the upstream (5' mRNA) direction.

In contemporary cells, natural tRNA nuclions serve to qualify and protect messenger RNA, mark start codons, provide frame registration, warehouse aminoacylated tRNAs and increase translation efficiency. Primordial nuclions, which contained an ancestral version of the TLS, pioneered protein synthesis before the advent of ribosomes. In order to maintain proper cellular control in contemporary cells, such protein synthesis by nuclions outside the ribosome should not be allowed. Nevertheless, in some embodiments, data mining studies indicate that TLS reversions to primordial configurations do occur in nature, and, in another embodiment, may cause certain cancers in higher organisms by triggering uncontrolled peptidyl transfer and/or cellular proliferation. In other embodiments, certain viruses may counterfeit nuclion structures when they invade cells in order to corrupt or hijack the cell's translation machinery. In several embodiments of the present invention, these surprising insights into the existence, structure, function and properties of nuclions and ribocapsids, together with an unprecedented understanding of their biological limitations and dysfunction, provide a new technology platform for biotechnology and nanotechnology, and present specific new targets inter alia for the development, manufacture and use of a new class of pharmaceutical products, including but not limited to novel drugs, biologics, diagnostics, therapeutics and prophylactics.

The discovery of nuclions and the embodiments of the present invention are surprising for a number of reasons. Hitherto, no biological structure has been reported or claimed in which one nucleic acid molecule is encapsulated by a polymeric shell of other nucleic acid molecules. Although there is a body of science describing how certain proteins form polymeric capsids around nucleic acids (particularly in viruses), there have been no published reports that nucleic acids form such shells.

A second surprising finding is that transfer RNA molecules play a much larger role in evolution and modern biology than was previously understood. In the more than fifty years since their existence was first postulated by Francis Crick (Crick, 1957, *A Note for the RNA Tie Club*, unpublished; Crick, 1958, *Symp. Soc. Exp. Biol.*, 12:138) and they were discovered in Paul Zamecnik's laboratory (Hoagland et al., 1958, *J. Biol. Chem.*, 231:241), transfer RNA molecules have usually been described as molecular adaptors to translate the information on messenger RNA (mRNA) into proteins. In protein synthesis, each tRNA is charged with a specific amino acid and enters the ribosome, whereupon the charged tRNA binds to a matching codon on the mRNA and the growing polypeptide chain on the previous tRNA is transferred to the amino acid on the incoming tRNA molecule.

The discovery of nuclions and several embodiments of the present invention have revealed the following additional biological properties and functions of transfer RNA, which have not previously been reported:

1. Transfer RNA molecules bind to messenger RNA in the absence of ribosomes, forming one or more polymeric ribocapsids around the mRNA; the resulting quaternary structure is a tRNA nuclion.
2. In each ribocapsid, adjacent tRNAs bind directly together via inter-molecular binding sites that are substantially conserved in most tRNAs in all biological domains.
3. The primary role of the conserved tRNA sequence G53-T54-P55-C56 is to serve as a transfer RNA link site ('TLS'), not as a ribosomal binding site as had previously been believed (Phillips, 1969, *Nature*, 223:347); the TLS usually binds to the CCA tail of the adjacent tRNA (the tRNA connector or 'TC').
4. Certain initiator tRNAs have modified TLS or TC sites, which block TLS-TC links and trigger nuclion capping to mark translation start codons while ensuring correct frame registration; the resulting nuclion is termed an 'initiation nuclion'.
5. Initiator tRNAs interact with defined mRNA marker structures, such as the Shine-Dalgarno sequence, to register and stabilize initiation nuclions.
6. Nuclions warehouse charged tRNAs ready for protein synthesis; this cache preloading improves translation logistics by accelerating both the sourcing and the delivery of charged tRNAs.
7. Nuclions stabilize the high energy but labile chemical bonds between the tRNAs and their amino acids, conserving energy which would otherwise be wasted; in effect, the tRNA nuclion is a battery.
8. Certain tRNA nuclions bind protein elongation factors such as EF-Tu and eEF1A, which truck the charged tRNAs from the nuclion warehouse to the ribosome factory for protein synthesis.
9. At least one of the TLS nucleosides in modern tRNAs (ribosylthymine at position 54) has evolved inter alia to minimize non-ribosomal protein synthesis, but certain mutations generate tRNAs with the primordial arrangement of pseudouridine at position 54; these revertants are associated with cellular transformations implicated in certain cancers.
10. Certain viruses, including some or all retroviruses, counterfeit nuclion and ribocapsid structures, presumably to bypass normal biological control systems and hijack the cell's protein synthesis machinery.
11. Thermodynamic forces alone can drive certain nuclions into staged conformations with progressively lower energy states, providing the mechanics and power for a helical engine; in the primordial RNA world, helical RNA engines pioneered protein synthesis before the advent of ribosomes.
12. The first ribosomes resulted from the fusion of two ribocapsid subunits; the peptidyl transfer center in modern ribosomes evolved from two tRNA pseudouridine loops which align the CCA tails of the aminoacyl and peptidyl tRNAs in the A and P sites of the ribosome.

The recognition that the early ancestors of tRNA were ribocapsid subunits solves one of the biggest mysteries in molecular biology, the origin of protein synthesis ('translation'). As Wolf and Koonin stated (Wolf et al., 2007, *Biology Direct*, 2:14): 'The origin of the translation system is, arguably, the central and hardest problem in the study of the origin of life, and one of the hardest in all evolutionary biology. The problem has a clear catch-22 aspect: high translation fidelity hardly can be achieved without a complex, highly evolved set of RNAs and proteins, but an elaborate protein machinery could not evolve without an accurate translation system.'

Put simply, a pivotal molecular biology question for the past 50 years has been: which came first, the genes or the proteins? The surprising answer to this apparent paradox is neither. Primordial ribocapsid RNAs, the ancestors of modern tRNAs, came first. The nuclion structural model teaches us that Darwinian selection in an RNA world led to the evolution of RNA genes to bind particular ribocapsid RNAs (not amino acids), the ribocapsid RNAs then evolved as molecular adaptors to bind amino acids (the modified ribocapsid surface conferred a selective advantage on the nuclion), and subsequently an RNA helical engine gave birth to protein synthesis. Ribosomes evolved later from the fusion of two ribocapsid RNAs. This unexpected insight explains several medically-important differences between the biological kingdoms (for example, substantial differences in translation initiation) and supports several embodiments of the present invention as a new platform technology for the design, development, manufacture and deployment of improved medical and industrial products, processes and services which leverage these differences (for example, the design, development, manufacture and use of new antibiotic and antiviral drugs).

In several embodiments of this invention, the nuclion structures and manufacturing methods are surprising to those skilled in the art. For example, in some embodiments, the yield of nuclions manufactured at 37° C. is substantially higher than the nuclion yield observed with the same manufacturing procedure at 8° C. This higher yield is now attributable inter alia to the synergistic thermodynamics associated with the quaternary structure of nuclions. But, before the advent of nuclion technology taught by this invention, this technical phenomenon could not be predicted, and was not predicted, by molecular biologists generally accustomed to observing tertiary nucleic acid structures that unfold and destabilize with increasing temperature.

Definitions

Wherever the following words and phrases are employed herein, they shall have the meanings defined in this section, regardless of whether or not the initial characters are capitalized, the word or phrase is used in the singular or plural, or a different tense is employed. In the event of a conflict between a definition in this section and any other definition, understanding or implication herein, then the definition in this section shall govern. Wherever a claim uses a word or phrase defined in this section, then such word or phrase shall be interpreted in accordance with the definition in this section together with any and all non-conflicting additional information herein which relates to such word or phrase.

Amino acid: As used herein in several embodiments, the term 'amino acid', refers to any compound and/or substance that can be incorporated into a polypeptide chain. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. 'Standard amino acid' or 'natural amino acid' refers to any of the twenty standard L-amino acids commonly found in naturally occurring peptides. 'Nonstandard amino acid' refers to any amino acid, other than the standard amino acids, regardless of whether it is prepared synthetically or obtained from a natural source. As used herein, 'non-natural amino acid' encompasses chemically produced or modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting their activity Amino acids may participate in a disulfide bond and other intra-molecular and inter-molecular links. The term 'amino acid' is used interchangeably with 'amino acid residue' and may refer to a free amino acid, an amino acid residue of a peptide or an amino acid conjugated, linked or bound to a nucleic acid, ribocapsid, nuclion or a component thereof. It will be apparent from the context in which the term is used whether it refers to a free amino acid, a residue of a peptide or an amino acid bound to a nucleic acid, ribocapsid, nuclion or a component thereof.

Association: As used herein, the terms 'association' and 'associated with' refers to the state of two or more entities, which are linked by any direct or indirect covalent or non-covalent interaction. In some embodiments, an association is covalent. In some embodiments, a covalent association is mediated by a linker moiety. In some embodiments, an association is non-covalent (e.g. charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, etc.).

Basic nuclion: As used herein, the term 'basic nuclion' refers to a nuclion that does not have a nuclion envelope. The term 'basic nuclion part' refers to a part of the nuclion inside the nuclion envelope(s) of the nuclion. In particular, basic nuclion part does not include any nuclion envelope(s).

Bound (or bind or bond): As used herein, the terms 'bound, 'bind', 'binds' and 'bond' refer to the association or connection of two or more atoms, chemicals, molecules, macromolecules, complexes, aggregates, chelates, substances, materials or surfaces by any physical, chemical, covalent, non-covalent, ionic, electrostatic, entropic, hydrogen-bonding, stacking, dipole-dipole, solvent, Van der Waals, charge, affinity, metal coordination, physical adsorption, host-guest, hydrophobic, base stacking, thermal, magnetic or other interaction, by any combination thereof, or by any hybrid thereof.

Core nucleic acid: As used herein, the term 'core nucleic acid' refers to a composition that is mostly nucleic acid, and includes a means of binding said composition to at least one ribocapsid. In some embodiments, 'core nucleic acid' refers to such a composition that can bind only one ribocapsid. In some embodiments, 'core nucleic acid' refers to such a composition that can bind two or more ribocapsids Core nucleic acid preparation: As used herein, a 'core nucleic acid preparation' is a composition (not a method or process) that refers to a preparation of a member selected from the group comprising a natural core nucleic acid, a non-natural core nucleic acid, natural core nucleic acids, non-natural core nucleic acids, homogeneous core nucleic acids, heterogeneous core nucleic acids, a solution of any member of this group, a solid form of any member of this group, a liquid form of any member of this group, an aerosol form of any member of this group, a formulation of any member of this group, a mixture containing any member of this group, any mixture of two or more members of this group, any combination of two or more members of this group, and any hybrid of two or more members of this group.

Enveloped nuclion: As used herein, the term 'enveloped nuclion' refers to a nuclion that is enclosed, coated, surrounded, jacketed, protected, cased, covered, treated, encapsulated or associated in whole, part or parts by or with one or more nuclion envelopes.

Enveloped nuclion preparation: As used herein, an 'enveloped nuclion preparation' is a composition (not a method or process) that refers to a nuclion preparation containing one or more enveloped nuclions.

Enveloped tRNA nuclion preparation: As used herein, an 'enveloped nuclion preparation' is a composition (not a method or process) that refers to a nuclion preparation containing one or more enveloped tRNA nuclions.

Enveloped ribocapsid: As used herein, the term 'enveloped ribocapsid' refers to a ribocapsid that is enclosed, coated, covered, treated, encapsulated or associated in whole, part or parts by or with an envelope, including but not limited to a nuclion envelope.

Enveloped tRNA nuclion: As used herein, the term 'enveloped tRNA nuclion' refers to a tRNA nuclion that is enclosed, coated, surrounded, jacketed, protected, cased, covered, treated, encapsulated or associated in whole, part or parts by or with one or more nuclion envelopes.

Homogeneous: As used herein, the term 'homogeneous' refers to the degree of uniformity in one or more predefined characteristics (including but not limited to composition, structure, arrangement, sequence, conformation, or another parameter) of a preparation, solution, intermediate, product, extract, isolate, fraction, mixture, or a population of molecules, complexes or structures (e.g. a population of ribocapsids or ribocapsid subunits in nuclions). In some embodiments, a population of compositions is considered to be 'homogeneous' if the compositions are at least 25%, 30%, 35%, 40%, 45%, 50%, 55%, 60%, 65%, 70%, 75%, 80%, 85%, 90%, 95%, or 99% identical with respect to one such characteristic. In some embodiments, a population of compositions is considered to be 'homogeneous' if, with respect to one characteristic, the compositions are at least 25%, 30%, 35%, 40%, 45%, 50%, 55%, 60%, 65%, 70%, 75%, 80%, 85%, 90%, 95%, or 99% dissimilar from compositions in the same class of compositions. For example, in some embodiments, a preparation of tRNA nuclions is considered to be 'homogeneous' if at least 25%, 30%, 35%, 40%, 45%, 50%, 55%, 60%, 65%, 70%, 75%, 80%, 85%, 90%, 95%, or 99% of the nuclions in the preparation have substantially the same predefined ratio of tRNA ribocapsid subunit molecules to core nucleic acid molecules.

Heterogeneous: As used herein, the term 'heterogeneous' refers to a lack of homogeneity with respect to one or more predefined characteristics (including but not limited to composition, structure, arrangement, sequence, conformation, or another parameter) of a preparation, solution, intermediate, product, extract, isolate, fraction, mixture, or a population of molecules, complexes or structures.

Homology: As used herein, the terms 'homology' and 'homologous' refer to the overall relatedness between biological macromolecules, e.g. between nucleic acid molecules (e.g. DNA molecules and/or RNA molecules) and/or between polypeptide molecules. As used herein, the term 'homologue' is a composition that is homologous to another composition. In some embodiments, macromolecules are considered to be 'homologous' if the tertiary structure of the macromolecules are substantially related. For example, all transfer RNA molecules are considered to be structurally homologous because of their overall L-shaped structure, regardless of structural differences between individual tRNAs. In some embodiments, macromolecules are considered to be 'homologous' if the tertiary structure of the backbone of the macromolecules (for example, the phosphodiester backbone of some nucleic acids) are substantially related. In some embodiments, macromolecules are considered to be 'homologous' to one another if their sequences are at least 25%, 30%, 35%, 40%, 45%, 50%, 55%, 60%, 65%, 70%, 75%, 80%, 85%, 90%, 95%, or 99% identical. In some embodiments, macromolecules are considered to be 'homologous' to one another if their sequences are at least 25%, 30%, 35%, 40%, 45%, 50%, 55%, 60%, 65%, 70%, 75%, 80%, 85%, 90%, 95%, or 99% similar. In some embodiments, the substitution of one pyrimidine with another pyrimidine, or one purine with another purine, maintains the same degree of homology. In some embodiments, the substitution of an unmodified base with a modified base, a modified base with an unmodified base, or a modified base with a different modified base, all wherein the parent base remains the same, is considered to maintain the same degree of homology.

Identity: As used herein, the term 'identity' refers to the overall relatedness between polymeric molecules, e.g. between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95% or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Initiation nuclion: As used herein, the terms 'initiation nuclion' and 'initiator nuclion' refer to a nuclion comprising (i) at least a part of a messenger RNA as a core nucleic acid, and (ii) one or more ribocapsids and/or two or more ribocapsid subunits bound to said mRNA at or near a start codon in said mRNA. In some embodiments, said ribocapsids and/or ribocapsid subunits of the initiation nuclion further comprises a means to bind to an initiation marker structure on said mRNA, including but not limited to a Shine-Dalgarno or Kozak sequence. In some embodiments, said ribocapsids and/or ribocapsid subunits of the initiation nuclion further comprises a means to bind to a ribosome. In additional embodiments, the core nucleic acid of the initiation nuclion comprises a ribocapsid binding sequence and/or ribocapsid subunit binding sequence operably linked to the start codon in the mRNA. The term 'operably linked to' refers to the functional relationship of one biological structure, composition, component or activity with another biological structure, composition, component or activity. In some embodiments, 'operably linked to' refers to the functional relationship of a nuclion, ribocapsid, ribocapsid subunit, or core nucleic acid with another nucleic acid sequence, another nucleic acid structure, or a biological activity.

Isolation: As used herein, 'isolation', 'isolate', 'isolated' and 'distinct' refer to the process, act or state, respectively, in which a starting mixture containing a substance, composition, structure, information, or entity is converted into two or more fractions or mixtures, in at least one of which the substance, composition, structure, information or entity is enriched. As used herein, 'in isolated form' means that the substance, composition, structure, information or entity is isolated relative to its previous state or context. In some embodiments, when applied to a sub-structure, the term 'in isolated form' refers to a portion of a structure that is informationally or physically isolated or distinct from the surrounding structure. Further, as used herein, an 'isolated nuclion' is intended to mean a nuclion that has been completely or partially removed from its native environment. For example, nuclions that have been removed or purified from cells are considered isolated. Moreover, a nuclion that is found in a cell, tissue or matrix in which it is not normally formed or found is also considered as 'isolated' for the purposes of the present invention. Similarly, nuclions that have been synthesized are considered to be isolated nuclions. Synthetically produced nuclions contained in host cells are considered isolated for the purposes of the present invention. 'Purified,' on the other hand is well understood in the art and generally means that the nuclions are substantially free of cellular material, cellular components, chemical precursors or other chemicals beyond, perhaps, buffer or solvent. 'Substantially free' is not intended to mean that other components beyond the novel nuclions are undetectable. The nuclions of the present invention may be isolated or purified.

Most (or mostly): As used herein, the terms 'most' and 'mostly' mean greater than 50%, including but not limited to greater than 50%, 60%, 70%, 80%, 90%, 95%, 98%, 99% and 99.9%, and including 100%.

Native tRNA: As used herein, the term 'native tRNA' refers to transfer RNA which has structure and/or components substantially similar or homologous to those found in natural tRNA, provided that native tRNA may be natural tRNA or non-natural tRNA as separately defined.

Nucleic Acid: As used herein, the term 'nucleic acid' refers to a polymer or oligomer of nucleotides. The terms 'nucleic acid' and 'polynucleotide' can be used interchangeably. In some embodiments, 'nucleic acid' encompasses RNA and DNA. The terms 'nucleic acid' and 'polynucleotide' include single and/or double-stranded RNA, DNA and hybrids thereof. Furthermore, the terms 'nucleic acid,' 'DNA,' 'RNA,' and/or similar terms include nucleic acid analogs, e.g., analogs having other than a phosphodiester backbone. For example, the so-called 'peptide nucleic acids,' which are known in the art and have peptide bonds instead of phosphodiester bonds in the backbone, are considered within the scope of the present invention. The term 'nucleotide sequence encoding an amino acid sequence' includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleotide analogs such as analogs having chemically modified bases or sugars, backbone modifications, etc. The term 'nucleic acid sequence' as used herein can refer to the nucleic acid material itself and is not restricted to the sequence information (e.g. the succession of letters chosen, for example, among the five base letters A, G, C, T, or U) that biochemically characterizes a specific nucleic acid, e.g., a DNA or RNA molecule. A nucleic acid sequence is presented in the 5' to 3' direction unless otherwise indicated. In some embodiments, a 'nucleic acid' or 'polynucleotide' comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propyny 1-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases, pseudouridine); intercalated bases; locked nucleic acid monomers; modified sugars (e.g., 2'-fluororibose, ribose, 2'-deoxyribose, arabinose, hexose, and a ribose moiety modified with a bridge connecting the 2' oxygen and 4' carbon); and/or modified phosphate groups (e.g., phosphorothioates and 5'-N-phosphoramidite linkages). As used herein, the terms 'nucleic acid' and 'polynucleotide' also include any natural or non-natural chain of nucleotides including but not limited to any and all modifications, derivatives, conjugates, variants, deletions, conformations, structures, symmetries, helices, branches, isomers, chirals, isotopes, analogs, equivalents, replacements, combinations, substitutes, functional equivalents, functional replacements, peptide nucleic acids, locked nucleic acids, precursors, ancestors, successors, decompositions, synthetic versions, artificial assemblies and other compositions of such a chain or its nucleotides, any combination of two or more thereof, and any hybrid of two or more thereof.

Nucleoside: In several embodiments, the term 'nucleoside' refers to a natural glycosylamine comprising a nucleobase (often referred to simply as a 'base') bound to a sugar (typically a ribose or 2'-deoxyribose) via a covalent linkage (typically a beta-glycosidic bond). In several embodiments, the term 'nucleoside' refers to a non-natural version, modification, substitute or equivalent of a natural nucleoside. The term 'nucleoside' generally excludes the linker moiety (for example, a phosphodiester linkage) that connects adjacent nucleotides in a nucleic acid.

Nucleotide: In several embodiments, the term 'nucleotide' herein refers to a natural composition comprising a nucleobase (often referred to simply as a 'base') bound to a sugar (typically a ribose or 2'-deoxyribose) via a covalent linkage (typically a beta-glycosidic bond), wherein the sugar is covalently attached (typically via its 5-carbon site, although sometime via its 2-carbon or 3-carbon) to a phosphate group. The term 'ribonucleotide' refers to a nucleotide where the sugar is ribose, and the term 'deoxyribonucleotide' refers to a nucleotide where the sugar is deoxyribose. Natural nucleotides can contain either a purine or a pyrimidine base. In several embodiments, the term 'nucleotide' refers to a non-natural version, modification, substitute or equivalent of a natural nucleotide. The term 'nucleotide' generally includes the linker moiety (for example, a phosphodiester linkage) that connects adjacent nucleotides in a nucleic acid. The linker moiety between adjacent nucleotides in a nucleic acid can comprise any chemical mechanism for linking the nucleotides and does not have to be a phosphodiester linkage.

Nuclion: As used herein, the term 'nuclion' refers to a composition that comprises (i) a core nucleic acid, and (ii) one or more ribocapsids each comprising a polymer of two or more ribocapsid subunits, wherein said ribocapsid subunits comprise nucleic acid. In some embodiments, (a) most of the ribocapsid subunits are bound to at least a part of the core nucleic acid, and (b) most of the ribocapsid subunits are bound to at least a part of one or more adjacent ribocapsid subunits. In some embodiments, the term 'nuclion' refers to such a composition that may or may not additionally comprise one or more nuclion envelopes. In some embodiments, the term 'nuclion' refers to such a composition without a nuclion envelope (a 'basic nuclion'). In some embodiments, the term 'nuclion' refers to such a composition with one or more nuclion envelopes (an 'enveloped nuclion'). In some embodiments, the term 'nuclion' refers to a tRNA nuclion. In some embodiments, the term 'nuclion' refers to a type of nuclion other than a tRNA nuclion. In some embodiments, the term 'nuclion' refers to all types of nuclion, with or without one or more nuclion envelopes. In some embodiments, the term 'nuclion' refers to a nuclion preparation. In some embodiments, the term 'nuclion' refers to an enveloped nuclion preparation.

Nuclion component: As used herein, the term 'nuclion component' refers to a member selected from the group consisting of a ribocapsid subunit, a ribocapsid, a core nucleic acid, a nuclion envelope, a combination of any two or more members of this group, and a hybrid of any two or more members of this group.

Nuclion device: As used herein, the term 'nuclion device' refers to a composition comprising a nuclion and a means for such nuclion to function as a device. In several embodiments, such device is a mechanical device or a machine. In several embodiments, such device is a chemical device. In several embodiments, such device is a means for information handling, processing or storage.

Nuclion envelope: As used herein, the term 'nuclion envelope' refers to a composition comprising (i) an envelope, shell, enclosure, layer, film, surface, surrounding, coating, jacket, protection, casing, covering, treatment, encapsulation, a combination of any two or more of the foregoing, or a hybrid of any two or more of the foregoing, and (ii) a means of binding said composition to the whole, a part or parts of a nuclion without a nuclion envelope, or to the whole, a part or parts of one or more nuclion components. In several embodiments, such composition may further comprise an item selected from the group consisting of an atom, metal, molecule, macromolecule, natural molecule, non-natural molecule, biological molecule, biological macromolecule, protein, enzyme, elongation factor, initiation factor, synthetase, antibody, hapten, nucleic acid, aptamer, ribozyme, lipid, phospholipid, carbohydrate, chemical, conjugate, signaling molecule, hormone, cell component, body component, tissue component, antigen, immune substance, complex, aggregate, material, natural substance, non-natural substance, imaging agent, pharmaceutical agent, therapeutic agent, diagnostic agent, prophylactic agent, ternary structure, radiopharmaceutical, radioactive substance, chelate, mixture, surface, particle, vesicle, capsule, pill, glue, excipient, adjuvant, colloid, film, a combination of any two or more members of this group, and a hybrid of any two or more members of this group.

Nuclion envelope preparation: As used herein, a 'nuclion envelope preparation' is a composition (not a method or process) that refers to a preparation of a member selected from the group comprising a natural nuclion envelope, a non-natural nuclion envelope, natural nuclion envelopes, non-natural nuclion envelopes, homogeneous nuclion envelopes, heterogeneous nuclion envelopes, a solution of any member of this group, a solid form of any member of this group, a liquid form of any member of this group, an aerosol form of any member of this group, a formulation of any member of this group, a mixture containing any member of this group, any mixture of two or more members of this group, any combination of two or more members of this group, and any hybrid of two or more members of this group.

Nuclion preparation: As used herein, a 'nuclion preparation' is a composition (not a method or process) that refers to a preparation of a member selected from the group comprising a natural nuclion, a non-natural nuclion, a natural enveloped nuclion, a non-natural enveloped nuclion, natural nuclions, non-natural nuclions, natural enveloped nuclions, non-natural enveloped nuclions, homogeneous nuclions, heterogeneous nuclions, homogeneous enveloped nuclions, heterogeneous enveloped nuclions, a natural tRNA nuclion, a non-natural tRNA nuclion, a natural enveloped tRNA nuclion, a non-natural enveloped tRNA nuclion, natural tRNA nuclions, non-natural tRNA nuclions, natural enveloped tRNA nuclions, non-natural enveloped tRNA nuclions, homogeneous tRNA nuclions, heterogeneous tRNA nuclions, homogeneous enveloped tRNA nuclions, heterogeneous enveloped tRNA nuclions, a solution of any member of this group, a solid form of any member of this group, a liquid form of any member of this group, an aerosol form of any member of this group, a formulation of any member of this group, a mixture containing any member of this group, any mixture of two or more members of this group, any combination of two or more members of this group, and any hybrid of two or more members of this group.

Nuclion target: As used herein, the term 'nuclion target' refers to a composition comprising a nuclion sub-structure and a means for preventing, promoting, changing or disrupting the structure, function or activity of a nuclion; wherein a nuclion sub-structure comprises a predefined portion of the structure of a nuclion, its components, or any combination of such components. In several embodiments, such predefined portion of the structure is selected from the group consisting of a primary structure, a secondary structure, a tertiary structure, a quaternary structure, an R-form structure, an S-form structure, a T-form structure, a combination of any two or more members of this group, and a hybrid of any two or more members of this group. In several embodiments, Nuclion yield: As used herein, the term 'nuclion yield' refers to the percentage of core nucleic acid that is converted into nuclions during nuclion assembly.

Oligomer (or oligomeric): As used herein, the terms 'oligomer' and 'oligomeric' refer to a set of repeating subunits, which is limited in length, wherein most subunits have sufficient structural homology for oligomer integrity. In some embodiments, most subunits have one or more means to bind to an adjacent subunit, a core molecule or both. In some embodiments, this means is a non-covalent bond. In some embodiments, this means is a covalent bond. In some embodiments, this means is a combination of non-covalent and covalent bonds.

Polymer (or polymeric): As used herein, the terms 'polymer' and 'polymeric' refer to a set of repeating subunits, which in principle is unlimited in length, wherein most subunits have sufficient structural homology for polymer integrity. In some embodiments, most subunits have one or more means to bind to an adjacent subunit, a core molecule or both. In some embodiments, this means is a non-covalent bond. In some embodiments, this means is a covalent bond. In some embodiments, this means is a combination of non-covalent and covalent bonds. As used herein, the terms 'polymer' and 'polymeric' also refer to oligomer and oligomeric, respectively.

Prevalence topogram: As used herein, the term 'prevalence topogram' refers to a presentation of (i) statistical information regarding the composition of an object, on (ii) a three-dimensional representation of that object. In several embodiments, 'prevalence topogram' and 'nucleoside prevalence topogram' refer herein to a presentation of nucleoside prevalence data on the tertiary structure of a transfer RNA molecule.

Protein synthesis marker sequence: As used herein, the term 'protein synthesis marker sequence' refers to a nucleic acid sequence in messenger RNA that is (i) upstream of, downstream of, or comprises, a start codon, and (ii) is operably linked to the initiation, termination, promotion, inhibition or control of protein synthesis. For example, protein synthesis marker sequence includes, but is not limited to, a Shine-Dalgarno sequence and a Kozak sequence.

Pure: As discussed above, a substance or entity is 'pure' or 'purified' if it is substantially free of other components. For example, a preparation that contains more than about 90% of a particular substance and/or entity is typically considered to be a pure preparation. In some embodiments, a substance and/or entity is at least 50%, 60%. 70%, 80%, 90%, 91%, 92%, 93%, 94%, 95%, 96%, 97%, 98%, 99% or 99.9% pure.

Ribocapsid: As used herein, the term 'ribocapsid' refers to an oligomer or polymer of two or more ribocapsid subunits, wherein said oligomer or polymer includes a means for binding said oligomer or polymer to the whole, a part, or parts, of a core nucleic acid. In several embodiments, the term 'ribocapsid' refers to a set of contiguous adjacent ribocapsid subunits bound to a core nucleic acid. In several embodiments, a nuclion may contain one, two or more ribocapsids, reflecting the number of oligomers or polymers of ribocapsid subunits that are bound to a single core nucleic acid.

Ribocapsid subunit: As used herein, a ribocapsid subunit refers to a composition that is mostly nucleic acid, wherein such composition has a means for binding said composition to a core nucleic acid, and also has a means for binding said composition to at least one adjacent ribocapsid subunit bound to the same core nucleic acid. For the avoidance of doubt, a ribocapsid subunit is not a single nucleotide or nucleoside.

Ribocapsid subunit preparation: As used herein, a 'ribocapsid subunit preparation' is a composition (not a method or process) that refers to a preparation of a member selected from the group comprising a natural ribocapsid subunit, a non-natural ribocapsid subunit, natural ribocapsid subunits, non-natural ribocapsid subunits, homogeneous ribocapsid subunits, heterogeneous ribocapsid subunits, a solution of any member of this group, a solid form of any member of this group, a liquid form of any member of this group, an aerosol form of any member of this group, a formulation of any member of this group, a mixture containing any member of this group, any mixture of two or more members of this group, any combination of two or more members of this group, and any hybrid of two or more members of this group.

Symmetry: As used herein, the terms 'symmetry' and 'symmetrical' refer to geometrical symmetry under a sub-group of the Euclidean group of isometries in two or three dimensional Euclidean space. These isometries consist of reflections, rotations, translations and any combination of these basic geometric operations. Helical symmetry is an example of a symmetry which combines a rotation with a translation. For example, in several embodiments of the present invention, ribocapsid subunits substantially composed of tRNA are arranged in an S-form tRNA nuclion, wherein, in some embodiments, these subunits exhibit helical symmetry around a central axis through the core nucleic acid. As used herein, the terms 'asymmetry' and 'asymmetrical' refer to the absence of symmetry.

Transfer RNA: A person skilled in the art of molecular biology has previously understood that the terms 'transfer RNA' and 'tRNA' generally mean a ribonucleic acid which functions as a molecular adaptor to translate the genetic code in messenger RNA into polymers of amino acids in proteins, and that this translation normally occurs in a ribosome. As used herein, the terms 'transfer RNA' and 'tRNA'refer to a member selected from the group comprising a tRNA without an attached amino acid (an 'uncharged tRNA'), a tRNA with an amino acid attached to its CCA tail (a 'charged tRNA'), a tRNA with an amino acid attached to a location other than its CCA tail, a modified tRNA, a selected tRNA, a natural tRNA, a non-natural tRNA, an archaeal tRNA, a bacterial tRNA, a viral tRNA, a plastid tRNA, a eukaryotic tRNA, a cytoplasmic tRNA, a mitochondrial tRNA, a native tRNA, a non-native tRNA, a tRNA that is charged, a tRNA that is not charged, a tRNA that is not chargeable, a tRNA charged with a natural amino acid, a tRNA charged with a non-natural amino acid, a tRNA charged with a standard amino acid, a tRNA charged with a non-standard amino acid, a tRNA charged with the correct amino acid, a tRNA charged with the wrong amino acid, a charged tRNA which employs normal acylation to connect the amino acid, a charged tRNA which does not employ normal acylation to connect the amino acid, a tRNA chargeable with one amino acid, a tRNA chargeable with more than one amino acid, an initiator tRNA, an elongator tRNA, a suppressor tRNA, a tRNA that serves as a primer, a tRNA that serves as a primer for enzymatic synthesis, a tRNA that serves as a ribozyme, a tRNA that serves as a primer for a ribozyme, a tRNA that serves as a retroviral primer, a hyperactive tRNA, a hypoactive tRNA, a tRNA with a correct anticodon, a tRNA with an incorrect anticodon, a tRNA with an anticodon of three nucleotides, a tRNA with an anticodon of other than three nucleotides, a tRNA that functions normally in a ribosome, a tRNA that does not function normally in a ribosome, a tRNA that is charged correctly by an aminoacyl synthetase, a tRNA that is not charged correctly by an aminoacyl synthetase, a tRNA that binds an elongation factor, a tRNA that does not bind an elongation factor, a tRNA that will form a ternary complex, a tRNA that will not form a ternary complex, a tRNA that will form an initiation complex, a tRNA that will not form an initiation complex, a labeled tRNA, an analytic tRNA, a diagnostic tRNA, a therapeutic tRNA, an imaging tRNA, a prophylactic tRNA, a tRNA vaccine, a tRNA standard, a radioactive tRNA, a tRNA radiopharmaceutical, a fluorescently-labeled tRNA, an enzymatically-tagged tRNA, a biotinylated tRNA, a magnetically-tagged tRNA, a tRNA attached to an imaging agent, a tRNA modified to be an imaging agent, a purified tRNA, an unpurified tRNA, a separated tRNA, an unseparated tRNA, an isolated tRNA, an unisolated tRNA, a tRNA in vivo, a tRNA in vitro, a tRNA ex vivo, a preparation of tRNAs, a homogeneous preparation of tRNAs, a heterogeneous preparation of tRNAs, a tRNA with a natural tRNA link site ('TLS'), a tRNA with a non-natural TLS, a tRNA with a natural tRNA connector ('TC'), a tRNA with a non-natural TC, a tRNA without a TLS, a tRNA without a TC, a contemporary tRNA, a tRNA with a CCA tail, a tRNA without a CCA tail, a tRNA with part of a CCA tail, a tRNA ancestor, a tRNA precursor, an immature tRNA, a mature tRNA, a tRNA metabolite, a primordial tRNA, an abnormal tRNA, a consensus tRNA, a hybrid tRNA, a tRNA with one or more mutations, a tRNA with one or more natural modifications, a tRNA with one or more non-natural modifications, a tRNA with a non-natural nucleotide or nucleoside, a tRNA with a non-natural modified base, a tRNA with a non-natural backbone, a tRNA with a modified backbone, a tRNA with one or more peptide bonds instead of phosphodiester bonds in the backbone, a tRNA with a non-natural amino acid stem, a tRNA with a non-natural dihydrouridine stem, a tRNA with a non-natural anticodon stem, a tRNA with a non-natural pseudouridine stem, a tRNA with a non-natural dihydrouridine loop, a tRNA with a non-natural anticodon loop, a tRNA with a non-natural pseudouridine loop, a tRNA with a modified amino acid stem, a tRNA with a modified dihydrouridine stem, a tRNA with a modified anticodon stem, a tRNA with a modified pseudouridine stem, a tRNA with a modified dihydrouridine loop, a tRNA with a modified anticodon loop, a tRNA with a modified pseudouridine loop, a tRNA conjugated to another molecule, a tRNA bound to another molecule, a tRNA associated with another molecule, a tRNA with primary structure, a tRNA with secondary structure, a tRNA with tertiary structure, a tRNA in a quaternary structure, a multimeric tRNA, a dimeric tRNA, a trimeric tRNA, a coated tRNA, an activated tRNA, an inactivated tRNA, a blocked tRNA, a customized tRNA, a specialized tRNA, a formulated tRNA, a tRNA formulated with an excipient, a stabilized tRNA, a cross-linked tRNA, a dried tRNA, a freeze-dried tRNA, a tRNA in solution, a tRNA crystal, a tRNA powder, a tRNA amalgam, a tRNA suspension, a tRNA colloid, a tRNA precipitate, a tRNA aerosol, a tRNA ointment, a tRNA mixture, any combination of two or more members of this group, and any hybrid of two or more members of this group.

tRNA nuclion: As used herein, 'tRNA nuclion' refers to a nuclion with at least one tRNA ribocapsid.

tRNA nuclion preparation: As used herein, a 'tRNA nuclion preparation' is a composition (not a method or process) that refers to a nuclion preparation in which at least one of the nuclions is a tRNA nuclion.

tRNA ribocapsid: As used herein, 'tRNA ribocapsid' refers to a ribocapsid in which at least one ribocapsid subunit is a tRNA ribocapsid subunit.

tRNA ribocapsid subunit: As used herein, 'tRNA ribocapsid subunit' refers to a ribocapsid subunit that is mostly tRNA.

tRNA ribocapsid subunit preparation: As used herein, a 'tRNA ribocapsid subunit preparation' is a composition (not a method or process) in which at least one of the ribocapsid subunits is a tRNA ribocapsid subunit.

Transfer RNA

Contemporary transfer RNA molecules serve as molecular adaptors, to translate the nucleotide sequence information on messenger RNA into a polymer of amino acids (as the length of this polymer increases, it is referred to, progressively, as a peptide, oligopeptide, polypeptide or protein). Each tRNA is aminoacylated ('charged') with a specific amino acid by a protein enzyme (an aminoacyl tRNA synthetase). Every tRNA normally contains a three-nucleotide anticodon which specifically binds to the corresponding three-nucleotide codon on mRNA (Labuda et al., 1982, *Biochem. Biophys. Acta*, 689:230). One tRNA molecule is normally attached to only one type of amino acid, but because the genetic code contains multiple codons that specify the same amino acid, tRNA molecules bearing different anticodons may carry the same amino acid. The specificity of a given tRNA is indicated herein by including a reference to the associated amino acid, in the form of 'tRNAaaa' or 'tRNA$^{aaa}$' where 'aaa' is the name of the amino acid (for example, methionine') or the standard three-letter symbol for the amino acid (for example 'Met' or 'met' for methionine). A charged (aminoacylated) tRNA is described herein using the format 'AAA-tRNA', 'AAA-tRNAaaa' or 'AAA-tRNA$^{aaa}$', where 'AAA' is the name of the amino acid connected to the tRNA or the standard three-letter symbol for the amino acid.

Inside the contemporary ribosome, the polypeptide on one tRNA bound to a codon is transferred to the amino acid on the tRNA bound to the next codon ('peptidyl transfer'), whereupon the polypeptide chain is extended by one amino acid. The tRNA previously holding the polypeptide exits the ribosome and becomes available for recharging. In each organism, there are two classes of transfer RNA molecules, elongator tRNAs and initiator tRNAs. Elongator tRNAs, which represent the majority of tRNA molecules, are responsible for the routine delivery of amino acids to the growing polypeptide chain. Initiator tRNAs are specialized tRNA molecules, which participate in the recognition of start codons on the mRNA, and have customized structural features to fulfill this role. In bacteria and related eukaryotic organelles, a formyl group is added to the methionine on the CCA tail of the initiator tRNA. Many eukaryotes, on the other hand, replace the ribosylthymine at position 54 in their cytoplasmic initiator tRNAs with an adenosine. The class of a given tRNA, initiator or elongator, is indicated herein by inclusion of the letter 'i' or 'e', respectively, in the tRNA abbreviations defined in the previous paragraph.

Although there has been speculation on the possibility of intermolecular interactions between adjacent transfer RNA molecules bound to messenger RNA (Webb, 1973, A Role for Pseudo-uridine, pages 1-7, 20-23 and 223-240 in *The Purification and Crystallisation of Transfer Ribonucleic Acids from Escherichia Coli*. A thesis submitted for the degree of Doctor of Philosophy in the University of London by Nigel Lawrence Webb, King's College, London, U.K.; Schimmel et al., 1994, *Proc. Natl. Acad. Sci. U.S.A.*, 91:11283), none of this speculation predicted that tRNA molecules could form nuclions and ribocapsids as taught by several embodiments of the present invention, nor did this speculation correctly predict the inter-tRNA binding mechanisms found in nature. Synthetic quaternary structures of tRNA molecules have been built (Severcan et al., 2010, *Nat. Chem.*, 2:772), but such structures have not been shown to exist in nature and do not have the physical and chemical characteristics or the advantages of nuclions or ribocapsids, including but not limited to the means by which the latter can encapsulate nucleic acids.

In molecular biology, the primary structure of a typical unbranched, un-crosslinked macromolecule such as DNA, RNA or protein is the specification of its atomic composition and the chemical bonds connecting those atoms. The primary structure of a biological macromolecule is equivalent to specifying the chemical sequence of its monomers, for example the nucleotides or amino acids. The direction of a macromolecule usually refers to the end-to-end chemical orientation of a single strand. With nucleic acids, the chemical convention of naming carbon atoms in the nucleotide numerically gives rise to a 5'-end and a 3'-end. The 5'-end designates the end of the DNA or RNA strand that has the fifth carbon in the sugar-ring of the deoxyribose or ribose, respectively, at its terminus. The 3'-end of a strand is so named due to its terminating at the hydroxyl group of the third carbon in the sugar-ring, and is known as the 'tail'. The relative positions of structures along a strand of nucleic acid, such as genes, codons and various binding sites, are usually noted as being either 'upstream' (towards the 5'-end) or 'downstream' (towards the 3'-end).

Secondary structure is normally defined by the intramolecular hydrogen bonds: in proteins, between backbone amide and carboxyl groups; in nucleic acids, between pairs of nitrogenous bases ('base pairs'). The secondary structure of RNAs can often be decomposed (into stems and loops) and further classified (for example, into hairpins, stacked stems, stem-loops, tetraloops and pseudoknots). Many of these secondary structural elements are functionally important to biological RNAs such as transfer RNA.

Nuclions and Ribocapsids

In several embodiments of the present invention, nuclions and ribocapsids are characterized, manufactured and tested with one or more of the following methods:

Data mining. Conserved patterns in the structure and composition of tRNA molecules are identified from large data sets of tRNA sequences and modified tRNA bases.

Computer modeling. Computer modeling is conducted to define the interactions between adjacent tRNA molecules bound to mRNA and the structures which result.

Nuclion manufacturing. Nuclions and ribocapsids are manufactured and tested under a variety of conditions using multiple types of tRNA, mRNA and synthetic RNA molecules.

Data Mining

In one embodiment, FIG. 3A presents the results of our data mining study of nucleoside prevalence in 623 transfer RNA sequences reported in the public database referenced to herein as 'tRNAdb' (Jühling et al., 2009, *Nucleic Acids Res.*, 37:D159), including natural initiator and elongator tRNAs in all biological domains, classes, specificities and cellular compartments (see 'Materials and methods for data mining and computer modeling'). The tRNA nucleoside location numbering in FIG. 3A follows the convention adopted by Jühling et al. (this numbering convention is employed for tRNA throughout this document) In the consensus tRNA secondary structure shown in FIG. 3A, dotted lines indicate canonical base-pairing, and arrows indicate stacking of (i) the amino acid stem (1-7; 66-72) with the pseudouridine stem (49-53; 61-65), and (ii) the anticodon stem (27-31; 39-43) with the dihydrouridine stem (10-13; 22-25). 'Nucleoside' in this figure includes both the base molecule and any modifications thereof. A linear representation of the nucleotides in a particular tRNA in a direction from the 5' end of the RNA to the 3' end would constitute the primary structure of the molecule.

The amino acid ('AA'), pseudouridine ('P'), anticodon ('AC') and dihydrouridine ('D') stems are marked in FIG. 3A and elsewhere termed AA-stem, P-stem, AC-stem and D-stem, respectively. Throughout this document, 'aa' and "AA' are used as abbreviations for amino acid. Other tRNA structural elements marked in FIG. 3A include the amino acid binding site ('aa' within a circle next to 76), the pseudouridine loop (54-60, P-loop), the anticodon loop (32-38, AC-loop) containing the anticodon (34-36 within the green box), the dihydrouridine loop (14-21, D-loop) and the variable loop (44-47, V-loop). The seventy six locations labeled 1-76 are usually occupied by a nucleotide and marked O (for occupied), unless otherwise marked for prevalence (see below). In contrast, twenty-three locations (0, 17a, 20a, 20b, e1-5, e11-17 and e21-27) are not usually occupied and are marked E (for extra).

Yellow boxes in FIG. 3A indicate locations where one nucleoside group (G, A, C or U), together with any modifications thereof) has a sequence prevalence (SP) of 90% or more within the 623 sequences analyzed. The letters in regular or italic type within such yellow boxes indicate, respectively, (i) the nucleoside group with an SP of more than 90% at that location (G, A, C or U) or (ii) the modified nucleoside with an SP of more than 50% at that location (P or T). Blue boxes indicate locations where the nucleoside class (purine or pyrimidine) has an SP of 90% of more. The letters in regular or italic type within such blue boxes indicate, respectively, (i) the nucleoside class with an SP of more than 90% at that location (R for purine, Y for pyrimidine) or (ii) the modified nucleoside with an SP of more than 50% at that location (H for modified adenosine). The D at position 20 indicates dihydrouridine with an SP of more than 50% at that location. FIG. 3B is a table of the sequence prevalence symbols and nucleoside abbreviations used in FIG. 3A. Certain nucleosides are marked with an asterisk to indicate that the related data refer to both the basic and modified forms of such nucleoside.

There are normally 7, 5, 5 and 4 base pairs in the AA-, P-, AC- and D-stems, respectively, for a total of 21 base pairs in four double-stranded RNA helices. This high level of conservation of nucleosides, nucleoside class and helical structures is observed substantially across all the biological domains, classes of tRNA, amino acid specificities and cellular compartments represented by these 623 sequences.

Computer Modeling

The tertiary structure of a macromolecule is the three-dimensional structure of a single chain, preferably defined by the atomic coordinates. In one embodiment, FIG. 4A shows the results of our computer modeling study in which ten reported tRNA tertiary structures, determined by X-ray diffraction from tRNA crystals, were superimposed and viewed from the right side of the molecules (throughout this document, 'right' is when the tRNA is viewed from its 3'-tail, with the AC-stem down). FIG. 4B is a view from the side distal to the 3'-tail of the same structures as those presented in FIG. 4A. FIG. 4C provides the color key and other information for the structures presented in FIG. 4A and FIG. 4B.

The remarkable degree of conservation of tRNA structure across all biological domains, implied by the earlier analysis of tRNA secondary structures, was corroborated in this comparison of tRNA tertiary structures. In all the tRNA crystal structures determined to date, the amino acid stem and pseudouridine stem helices stack together, while the anticodon and dihydrouridine stem helices stack together. The elbow of this conserved L-shaped tRNA structure is formed primarily by intra-molecular interactions between the pseudouridine and dihydrouridine loops.

Quaternary structure is the defined organization of two or more macromolecules with tertiary structure. The great majority of natural quaternary structures reported to date are protein molecules (examples: hemoglobin, muscle filaments), or combinations of protein molecules with nucleic acids (examples: ribosomes, viruses). All these quaternary structures are held together by a combination of hydrogen bonding, Van der Waals and electrostatic forces. The term 'quaternary order' has been applied to DNA for its higher-level organization in chromatin, where the DNA is complexed with histones. The interactions between separate RNA units in the ribosome and the spliceosome have also been described as nucleic acid quaternary structures but most, if not all, of these complexes contain proteins. Other than double helices of nucleic acids, few natural quaternary structures comprised solely of nucleic acids have been reported to date. Certain aptamers are quaternary structures of multiple RNA molecules, but these RNAs do not have a ribocapsid shell with the oligomeric or polymeric subunits that are characteristic of nuclions.

Computer modeling (in silico study) is being used to predict and determine the secondary and tertiary structures of tRNA molecules (see, for example, U.S. Patent Publication 2011/0112817), but there are no reports or claims of computer modeling studies which yielded the nuclion or ribocapsid structures taught by several embodiments of the present invention.

Inter-tRNA Binding Sites

In one embodiment, FIG. 5A is a nucleoside prevalence topogram in which the 15 tRNA nucleosides with a global sequence prevalence of 90% or more ('GSP90') are presented on the tertiary structure of yeast tRNA$^{Phe}$ (Shi et al., 2000, *RNA*, 6:1091). FIG. 5B provides the color key to the nucleotides in FIG. 5A. This topogram reports the prevalence of individual nucleosides, not merely the nucleoside type (purine or pyrimidine). These 15 GSP90 nucleosides in tRNA are located in four conservation zones, two of which have well-documented functions, the anticodon loop and the 3' CCA tail attached to the amino acid stem. The highly conserved CCA tail, which is esterified ('aminoacylated') with an amino acid specific for the tRNA preparatory to protein synthesis, also serves as the tRNA connector (TC) in a ribocapsid and usually binds to the tRNA link site on a 5'-adjacent ribocapsid tRNA bound to the same mRNA.

Most of the GSP90 nucleosides, 11 out of 15, are in the tRNA elbow region. Three of these eleven GSP90 nucleosides (A14 and A21 from the D-loop plus U8 between the AA-stem and D-stem) form a planar triple structure at the base of the elbow (the 'AUA triple'), which likely allows the tRNA molecule to adjust its structure under certain circumstances.

Figures 6A, 6B, 6C:
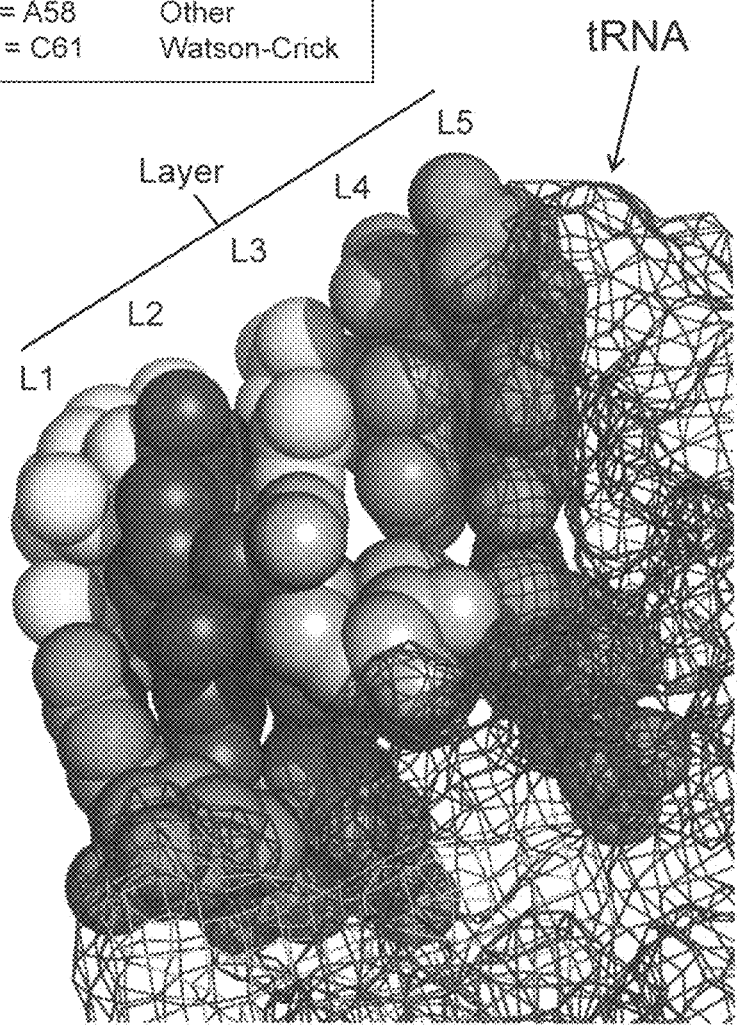
FIG. 6A is a computer model of the tRNA link site (TLS) in yeast tRNA$^{Phe}$ and its nine conserved TLS nucleosides, comprising eight GSP90 nucleosides and one PSP90 purine, stacked in five layers marked L1 through L5. Atoms in these TLS nucleosides are shown as space-filling; other nucleosides are represented by mesh.
FIG. 6B shows which TLS nucleosides in FIG. 6A are base-paired to other TLS nucleosides and by which method.
FIG. 6C provides the color key to the TLS nucleotides in FIG. 6A using the abbreviations defined in FIG. 3B.

In one embodiment, eight of the eleven elbow nucleosides are located together within a substantial five-layered stack (shown in FIG. 6A) built from nine nucleotides: six GSP90 nucleosides from the P-loop (G53-T54-P55-C56, A58, C93), two GSP90 nucleosides from the D-loop (G18-G19) and one PSP90 purine (R57), also from the P-loop. FIG. 6B shows which of the TLS nucleosides in FIG. 6A are base-paired to other TLS nucleosides and by which method ('Watson-Crick' indicates a canonical base pair, 'other' indicates a Hoogsteen or other type of base pair). FIG. 6C provides the color key to the TLS nucleotides in FIG. 6A, using the abbreviations defined in FIG. 3A.

This stack of nine nucleotides in the tRNA elbow is the active center of the tRNA link site, which usually binds the CCA tail of the 3'-adjacent ribocapsid tRNA. Not only are the types of nucleoside in this tRNA link site highly conserved across all biological domains, but their conformations are also highly conserved. For more than forty years it had been the understanding of those skilled in the art that the primary role of the tRNA nucleotide sequence G53-T54-P55-C56 was to bind to the ribosome (Phillips, 1969, *Nature*, 223:347), so the discovery of inter-tRNA links and several embodiments of this invention are unexpected.

In one embodiment, FIG. 7A is a close-up view of these TLS nucleotides in the ten reported tRNA structures previously compared in FIG. 4A. FIG. 7B provides the color key and other information for the structures presented in FIG. 7A. With one exception, the locations of the atoms in these TLS nucleotides in these structures are substantially fixed in space. This observation is remarkable when one considers that the nine conforming structures include bacterial initiator methionine tRNA from *E. Coli* and eukaryotic elongator tRNAs from three species (yeast phenylalanine and aspartic acid, calf lysine and human selenocysteine tRNAs). By standardizing the structures of the TLS and TC binding sites in all elongator tRNAs, and using tRNA molecules with conserved geometry (insofar as the geometry impacts nuclion formation), an organism is able to assemble uniform ribocapsids, while permitting the component tRNAs and their associated anticodons to vary in accordance with the required amino acid specificity programmed by the codons on the messenger RNA.

The one substantial structural exception in FIG. 7A is yeast initiator tRNA. Yeast, as is typical for many eukaryotes, replaces the T54 in its cytoplasmic initiator tRNAs with an adenosine (Kolitz et al., 2010, *FEBS Lett.*, 21:584), hence the observed spatial variance. This atypical adenosine plays a critical role in the modulation of nuclion structure and the associated flagging of start codons on mRNA in eukaryotes, as described below. Initiator tRNAs can turn off selected TLS and TC binding sites and thereby precisely interrupt ribocapsid segments, providing a powerful mechanism for marking start codons with distinct nuclion flag structures.

Prior to the discovery of nuclions and ribocapsids, and the embodiments of the present invention, there have been several reported experimental studies of binding and complex formation between nucleic acids, tRNAs and other molecules, and associated patent activity (see, for example, U.S. Pat. Nos. 7,902,169; 7,745,594; 7,049,431; 5,821,052; and U.S. Patent Publications 2010/0056768; 2010/0016409; 2008/0026389; 2005/0266416; 2004/0157304), including but not limited to reports of the binding of tRNA anticodons to complementary codons on mRNA and complementary codons on other tRNAs, but none of the reported studies or patent claims has addressed the inter-tRNA binding between the TLS and TC sites on tRNA molecules which leads to polymeric ribocapsid formation.

T-Form Nuclion

In one embodiment, FIG. 8A shows a computer model (see 'Materials and methods for data mining and computer modeling') of two tRNA molecules bound to adjacent mRNA codons in the repeating structure typical of one conformation of tRNA nuclion (designated the 'T-form'). FIG. 8B provides the color key to the nucleotides in FIG. 8A using the abbreviations defined in FIG. 3B.

The aminoacylated CCA in the TC on the tRNA in the 3' mRNA (downstream) direction (blue) binds to the TLS on the 5'-adjacent (upstream) tRNA (dark green). The left and right sides of the TLS are marked by the sequences T54-P55-C56 (yellow) and G18-G19 (cyan), respectfully. The mRNA (orange) is close to the axis of the nuclion which is represented by a dashed line. In this and subsequent computer models of nuclions, the crystal structure of yeast tRNA$^{Phe}$ was employed (the conformation of the associated anticodon loop in such structure is designated as 'L-form'). Phenylalanine molecules (red) were added using the build function with the PyMOL computer software employed for modeling (*PyMOL* by Surhone et al., VDM Publishing House, 2010) to the CCA tail (raspberry) to facilitate visualization and analysis of the aminoacyl construct. However, the tail configuration reported from X-ray structural studies was retained. In practice, this CCA tail is known to be very flexible. As a result, the probable CCA configuration in vivo is closer to the TLS site than is shown in this and subsequent computer models.

The tRNAs in the T-form ribocapsid repeat in a right handed helix about the indicated axis, with each CCA tail (colored raspberry) towards the 5' mRNA direction and each anticodon (colored light green) towards the 3' mRNA direction (all 5' and 3' references henceforth refer to the mRNA orientation). The A76 of each tRNA aligns with the right side of the TLS on the adjacent tRNA in the 5' direction ('right' when viewed from the AA-stem on the tRNA, with the anticodon down). The tRNA helix rotation per tRNA (~98±10°) is substantially that of three nucleotides in canonical A-form RNA (98°) but the T-form helix rise per tRNA is different (~15±3 Å versus ~8.4 Å for three nucleotides in A-RNA). Throughout this document, the symbol '~' means approximately.

In one embodiment, FIG. 9A shows a computer model of three such tRNAs when viewed on the nuclion axis from the 5' direction. FIG. 9B provides the color key to the nucleotides in FIG. 9A using the abbreviations defined in FIG. 3B. The dihydrouridine moieties on each tRNA are adjacent to the aminoacyl stem on the 3'-adjacent tRNA, consistent with a role for the DHUs as intermolecular electrostatic insulators between TC and TLS sites, presumably to enhance TC-TLS link specificity.

In another embodiment, FIG. 10A shows a computer model of ten such L-form tRNAs in a T-form nuclion. No steric interference was observed at this level of axial compression, so, in principle, there is substantially no geometric limit to its length (accordingly, the tRNA subunits in a T-form ribocapsid are deemed to be 'polymeric'), although its thermodynamic stability may limit its length in practice, under certain environmental conditions. FIG. 10B provides the color key to the nucleotides in FIG. 10A using the abbreviations defined in FIG. 3B.

Figure 11:
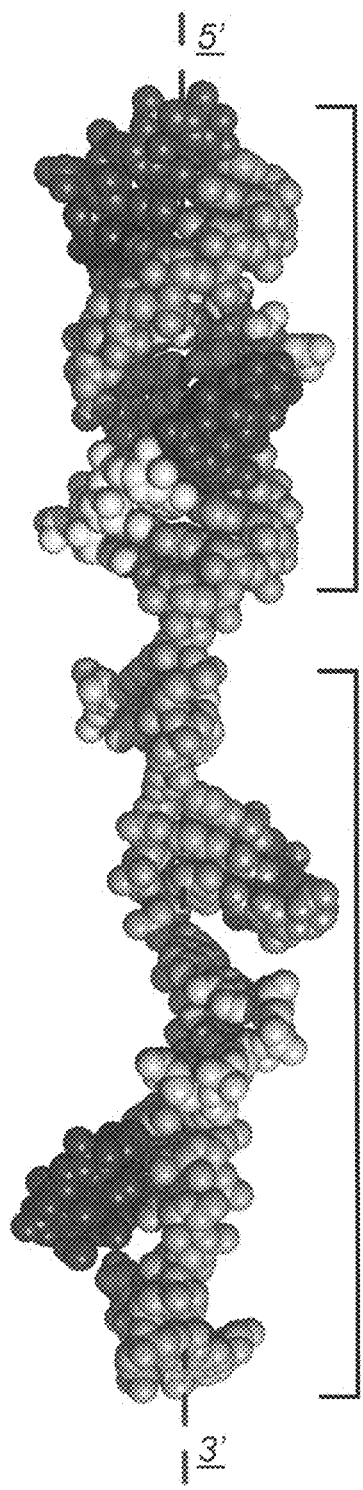
FIG. 11 is a computer model of mRNA codons bound to tRNA anticodons in adjacent S- and T-conformations of a tRNA nuclion (other tRNA atoms are not shown). The mRNA codons are orange. All the other colors are tRNA anticodons. The adjacent table presents the helix rise and helix turn values per tRNA for the nuclion helices corresponding to these two nuclion conformations, together with the associated tRNA anticodon conformations.

The overall fit between adjacent tRNAs in this T-form nuclion is good, but some space remains between tRNAs in the axial direction. Although the L-form tRNAs in this ribocapsid are arranged in a helical structure, the codons and anticodons for each tRNA in the T-form nuclion are not stacked with those of adjacent tRNAs, as shown in FIG. 11, in another embodiment.

With the AC-loop L-conformation found in yeast tRNA$^{Phe}$ crystals, potential steric interference between adjacent AC-stems prevents greater axial packing of the tRNAs in this T-form nuclion. The codons are close to the nuclion axis, with the anticodons off-axis. The anticodons are only stacked within their parent tRNAs, not with each other. The codons in this T-form nuclion are not stacked with each other.

S-Form Nuclion

Evidence for a second tRNA anticodon loop conformation ('K-form') comes from NMR studies with *E. Coli* tRNA$^{Phe}$ in solution (Cabello-Villegas et al., 2005, *Nucleic Acids Res.*, 33:6961), which suggest that nucleotides 32-33 and 37-38 can stack opposite each other under the anticodon stem. In one embodiment of the present invention, our computer model of this second AC-loop conformation (FIG. 12A) shows the three anticodon nucleotides 34-36 unstacked from the tRNA stem, in contrast with the anticodon stacking under the 3' side of the AC-stem as seen in the L-form AC-loop structure (FIG. 12B) generally reported from X-ray determinations of tRNA crystal structures. Studies of the effect of magnesium concentration on tRNA structure also indicate more than one anticodon loop confirmation (Bujalowski et al., 1986, *Biochem.*, 25:6365) and suggest that the whole tRNA tertiary structure is magnesium dependent (Friederich et al., 1997, *Biochem.*, 36:6090). Temperature-jump kinetics using a fluorescently-labeled modified base on the tRNA show that the anticodon loop is flexible and changes conformation on binding the codon (Yoon et al., 1975, *J. Molec. Biol.*, 99: 507). Electrophoretic studies also suggest multiple conformations of the anticodon loop (Pieczenik, 1980, *J. Molec. Biol.* 138:897). Accordingly, depending on its physical and chemical environment, the AC-loop can adopt more than one conformation, and hybrids of such conformations, inter alia to facilitate tRNA participation in ribocapsids and nuclions.

In one embodiment, adoption of the K-form of the AC-loop in a nuclion allows both codons and anticodons to stack with those of their tRNA neighbors (FIG. 11), forming a helical core structure with dimensions substantially similar to those of a canonical A-form RNA helix. The lower energy state of the resulting compressed nuclion (designated 'S-form') is thermodynamically preferable to that of the less-stacked T-form, driving an automatic transition from T-form to S-form ribocapsid concomitant with the anticodon loop transition from the L to the K form. In the T-form nuclion, the L-form anticodon is stacked under the AC-stem (but not with adjacent anticodons), the conserved uridine 33 is flipped out and the modified purine 37 is partially stacked, while none of the codons is stacked with its neighbor. In the S-form nuclion, each K-form anticodon primarily stacks with adjacent anticodons instead of its parent tRNA, but U33 and R37 do now stack with their parent tRNA, and adjacent codons are also stacked. This S-form nuclion generates more total stacked bases per tRNA than the T-form nuclion and more bases in double helices. Once tRNAs bind to mRNA and their TLS connections align them in a T-form nuclion, this thermodynamic difference can, provided there are no upstream geometric constraints, automatically drive a nuclion transition from T- to S-form.

In one embodiment, FIG. 13A shows a computer model of four K-form aminoacylated tRNAs in an S-form nuclion in which all the codons and anticodons stack with those of their tRNA neighbors. FIG. 13B provides the color key to the nucleotides in FIG. 13A using the abbreviations defined in FIG. 3B. The resulting helix turn per tRNA is ~98° (substantially the same as A-RNA and the T-form nuclion), but the helix rise per tRNA is now ~8.4 Å (versus ~15±3 Å for the T-form), the same as that for three nucleotides in an A-RNA helix. The primary structural impact of the T-form to S-form transition is a ~45% axial compression of the nuclion, leading to closer packing of tRNAs around the mRNA. In the S-form nuclion, the approach angle of the aminoacylated A76 to the TLS is substantially similar to that in the T form. No stereochemical impediments to the proposed T to S transition were evident from the computer modeling studies. Due to steric interference, and in contrast with the T-form, the number of adjacent tRNAs participating in an S-form nuclion is substantially limited to four (accordingly, the tRNA subunits in an S-form ribocapsid are deemed to be 'oligomeric'). Contact between the most 5' tRNA in the S-form (tRNA1) and the tRNA four codons away (tRNA5) substantially prevents the latter from joining the S-form nuclion and keeps it in the T-form or a hybrid S/T structure.

R-Form Nuclion Cap

Computer modeling showed that an S-form nuclion can be capped on its 5' end with a single tRNA molecule. In one embodiment of the present invention, FIG. 14A shows a computer model of such an R-form nuclion tRNA cap, which has an even lower energy state than tRNAs in the S or T forms of nuclion, because its L-form anticodon loop stacks with both its parent AC-stem and the core nuclion helix. FIG. 14B provides the color key to the nucleotides in FIG. 14A using the abbreviations defined in FIG. 3B.

In contrast, the tRNA AC-loops in S and T form nuclions stack with either the parent AC-stem or the nuclion helix, but not both at the same time. Computer modeling studies showed that such a tRNA cap with full AC stacking can occur for only one tRNA molecule at a time and that its TC-TLS connections have first to be severed. The thermodynamic drive for such stacking and severance is amplified by coaxial alignment of the AC-stem of the tRNA cap with the nuclion core helix, effectively trebling the length of the stacked S-form RNA helix through the addition of 10 or more base pairs in the capping tRNA above its AC-loop.

In one embodiment of the present invention, the aminoacyl stem of the capping tRNA in the R-form nuclion binds to an upstream structure in the RNA, in order inter alia to register and phase the binding of a initiator tRNA molecule, concomitant with accurate frame registration and improved formation of a nuclion complex to mark the initiation site in a mRNA. In one embodiment, an example of such an interaction in bacteria is the binding of the aminoacyl stem of the initiator tRNA to a protein synthesis marker sequence, such as the Shine-Dalgarno ('SD') sequence which is often located a short distance upstream of the initiation codon in bacterial mRNA. The Shine-Dalgarno sequence also functions to bind a ribosome, whereupon the initiator tRNA is presumably displaced from binding to the SD site.

Nuclion Dynamics

Figure 16:
FIG. 16 is a computer model of a compound tRNA nuclion and an associated information table, both of which correspond to the schematic drawing in FIG. 15. Two aminoacylated tRNAs are shown bound to the mRNA downstream from the nuclion. The dashed line is the nuclion axis, marked 5' and 3' to indicate the direction of the mRNA which is orange.

In one embodiment in contemporary cells, the thermodynamic properties of the different forms of tRNA nuclion can, under predefined conditions, automatically drive the transition of aminoacylated tRNAs from free solution to (i) initial mRNA binding in a relatively uncompressed T-form ribocapsid structure of variable length; then to (ii) a fully compressed S-form ribocapsid up to four tRNAs long; and finally to (iii) a single coaxial R-form tRNA capping the nuclion structure. The most stable portion of the nuclion structure comprises the R and S forms, for a total of five tRNAs (or six tRNAs, when the hybrid S/T tRNA is included). In one embodiment, a schematic diagram of a resulting compound tRNA nuclion is provided in FIG. 15 and a computer model of this nuclion is shown in FIG. 16.

In another embodiment, FIG. 17 summarizes the physical characteristics of the three different forms of tRNA nuclion, and presents the stacking, base pairing and axial dipole properties which confer progressively lower energy states on the T, S and R forms. The energetic relationships between these three nuclion forms explain why messenger RNA is normally translated in the 5' to 3' direction. The structure of a tRNA molecule necessitates that it first enters the T-form nuclion from the 3' direction, then progressively transitions to S-form to R-form in the 5' direction. Each time an R-form tRNA is removed for protein synthesis, the 3'-adjacent S-form tRNA transitions to R-form and the nuclion moves along the mRNA in the 5' to 3' direction by one codon.

In this model of tRNA nuclion dynamics in cellular organisms, tRNAs are progressively transported from the nuclion to the ribosome by elongation factor proteins, whereupon the nuclion segment containing the five current tRNAs in R and S form moves along the mRNA in the 5' to 3' direction with a T-form tail, the length of which depends in part on the supply of aminoacylated tRNAs. The incoming charged tRNAs bind randomly to triplets (not necessarily codons) on mRNA, with a short residence time, but are then rapidly qualified by the ribocapsid. At any given time, only one charged tRNA, properly bound to the codon immediately adjacent to the 3' end of the T-ribocapsid, can lock into the one available and open TLS on the 5'-adjacent tRNA, adopt the lower T-form energy state, and stay. This selection process efficiently qualifies charged tRNAs and preserves frame integrity while amplifying rejection of non-cognate tRNAs. In so doing, the nuclion also acts as a charging accelerator by binding aminoacylated tRNAs from free solution early, in substantially the quantities needed for upcoming translation (i.e. cache preloading), thereby advancing feed-back loops which modulate their synthesis. The model provides that, depending on the capping status and other factors, the number of contemporary tRNAs contiguously-bound at an mRNA site is four or five, corresponding to the aggregate of the R and S nuclion forms. In several embodiments of this invention, the relative stability of this T-form structure under predefined conditions is substantially less than less than that of the S-form. In several embodiments, the hybrid S/T tRNA immediately adjacent to a S-form tRNA can stack with the latter, giving a total of six contiguous tRNAs in a compressed nuclion.

In one embodiment of this invention, a tRNA must be aminoacylated in order to transition from a T-form structure to an S-form structure, and this requirement provides an additional screening method for ensuring the integrity of charged tRNAs. Whereas, in this embodiment, tRNAs in the S-form must be charged, the T-form nuclion can accommodate both charged and uncharged tRNAs. It is also possible that the aminoacylation of a tRNA changes its electrical properties and facilitates the conversion of its anticodon into the preferred conformation for an S-form nuclion structure.

The modern tRNA nuclion securely warehouses aminoacylated tRNAs, which would otherwise have a relatively short half-life in free solution (Piltz et al., 1997, *Nucleic Acids Res.*, 125:1862) and waste valuable free energy. In other words, the tRNA nuclion functions as a battery. The FIFO (first-in-first-out) inventory management system also acts as a translation accelerator by preloading the mRNA, so the ribosomal peptidyl transfer center does not have to wait as long for sequential Brownian access by the necessary charged tRNAs; input kinetics are favorably saturated. A nuclion cap marks qualified codon stretches and facilitates control by other molecules. Translation is started by initiator tRNA blocking of TC-TLS links, thereby triggering capping by the initiator or its neighbor. The tRNA ribocapsid may also protect the messenger RNA from hydrolysis, enzymatic attack or corruption, and serve as a vehicle to transport the message within the cell and between different compartments in eukaryotic cells. These insights form the basis of several embodiments of the present invention.

Initiation Nuclions

The central role of TC-TLS links between adjacent ribocapsid tRNAs provided a natural mechanism for a tRNA nuclion to mark a start codon on messenger RNA. Such a nuclion is referred to herein as an 'initiation nuclion'. Initiator tRNAs have evolved to block one of the two TC-TLS links with their 5' and 3' neighbors on the mRNA, forcing a tRNA into the cap position on the nuclion and providing a ribocapsid flag for the ribosome to initiate protein synthesis. As shown in the schematic drawings of FIG. 18 and FIG. 19, two link-blocking directions were possible in evolution: upstream or downstream of the initiator tRNA, that is, towards its 5' or 3' neighbor, respectively. One or both of these blocking directions are employed in several embodiments of the present invention.

An upstream block (shown in FIG. 18), which is utilized by bacteria and related eukaryotic organelles, requires modification of the TC aminoacyl tail on the initiator tRNA, to prevent connection with the upstream tRNA, thereby forcing the initiator tRNA into the R-form cap position. The resulting bacterial initiation nuclion marks the start codon for protein synthesis. With this type of initiator tRNA in bacteria, a formyl group is attached to the methionine on the CCA tail, in order to prevent this TC site binding to the TLS on the upstream adjacent tRNA. A further benefit of such formylation is that it stabilizes the aminoacyl linkage on the initiator tRNA. This linkage is exposed and not protected by normal ribocapsid binding because the initiator tRNA is the most 5' ribocapsid subunit.

Figure 19:
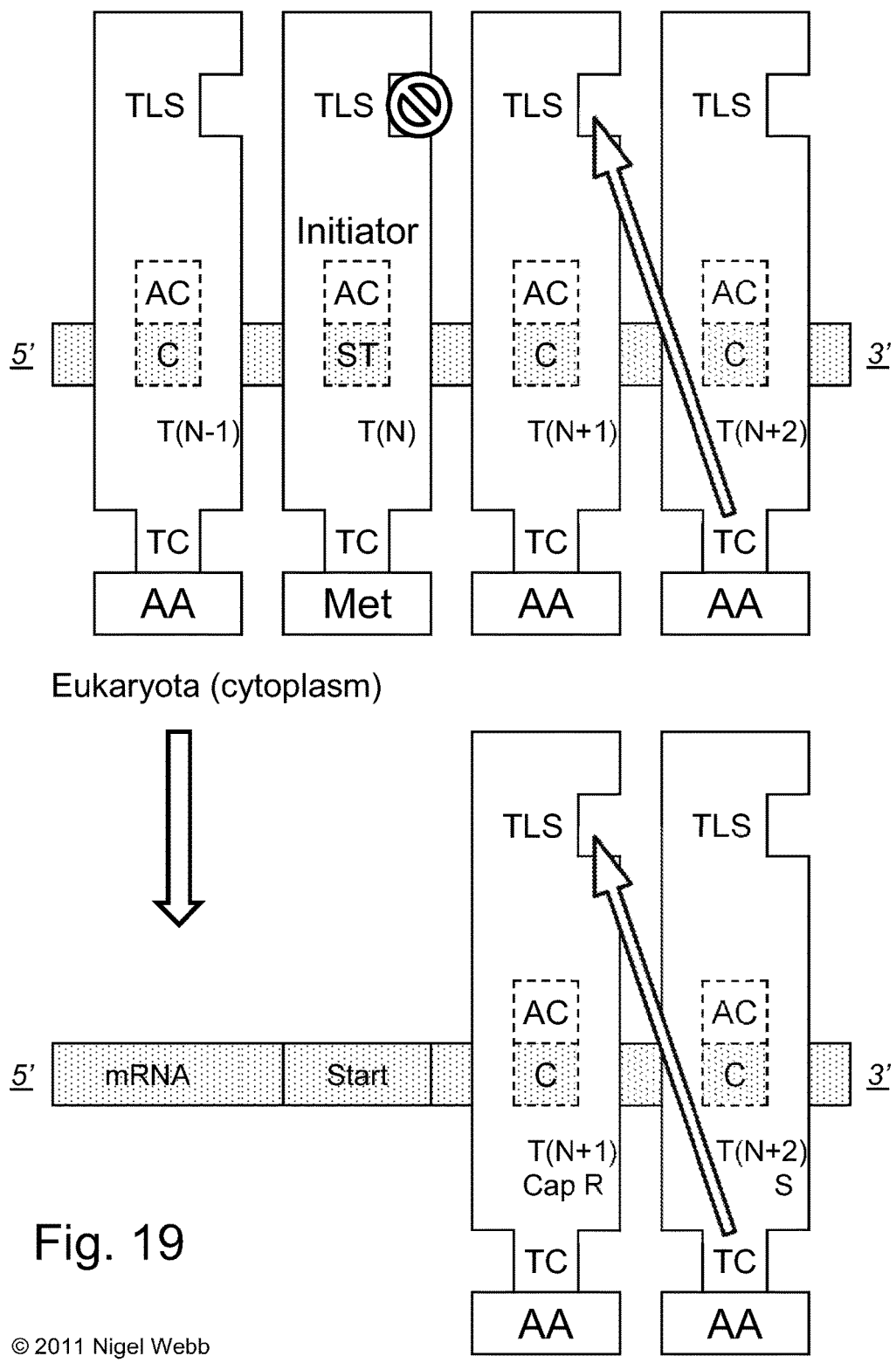
FIG. 19 is a drawing of initiation (start) codon marking by tRNAs in the cytoplasm of eukaryota, before (upper) and after (lower) the formation of an initiation nuclion. T(N−1) through T(N+2) represent tRNA molecules, AA represents an amino acid attached to an elongator tRNA. Met (methionine) is attached to the initiator tRNA. 5' and 3' mark the direction of the ends of the mRNA. C represents a codon on the mRNA. AC represents an anticodon on a tRNA. R and S indicate the nuclion conformation at that tRNA. The angled arrows indicate the binding of a tRNA connector (TC) on one tRNA to a tRNA link site (TLS) on another tRNA. The 'no parking' sign indicates that the modified TLS site cannot bind the TC connector on the adjacent downstream tRNA.

In contrast, the downstream block (as shown in FIG. 19) utilized by cytoplasmic initiator tRNAs in eukaryota, employs a modification to the initiator TLS site, in order to prevent binding of the CT on the 3'-adjacent tRNA, thereby forcing this downstream neighbor into the cap position and generating a eukaryotic initiation nuclion.

These nuclion initiation mechanisms generate different capping outcomes for the two types of link block. With an upstream block, the cap on the initiation nuclion is the initiator tRNA itself, which occupies the start codon on the mRNA. With a downstream block, however, the cap on the initiation nuclion is not the initiator tRNA but its 3' neighbor, and the start codon is vacated. This distinction between initiator nuclions is consistent with the observed differences in ribosomal initiation between bacteria and eukaryota. Whereas bacterial ribosomes initiate directly at the occupied start codon, the eukaryotic ribosome first forms a complex which includes an initiator tRNA, remote from the start codon, then the ribosomal complex scans the mRNA looking for an open start codon. Eukaryotic marking of the initiation site with an R-tRNA nuclion cap on the second codon to be translated provides a prominent target for the scanning ribosome and reduces the need for upstream codon recognition or preliminary frame registration. These difference in nuclion initiation mechanisms are also consistent with the fact that messenger RNAs in bacteria and related eukaryotic organelles are generally polycistronic (that is, have multiple open reading frames, or 'ORFs'), whereas most mRNAs in the cytoplasm of eukaryotes (including animals and humans) are monocistronic (with one ORF). In bacteria, the ribosomes can bind to the mRNA at multiple start codons flagged by multiple nuclion structures, whereas the ribosomes in eukaryota normally attach just to the 5' end of the mRNA. In one embodiment of the present invention, our computer modeling studies indicate that certain viruses in eukaryota have learned how to bypass these nuclion flag control systems by simulating nuclion start signals in the middle of the mRNA and attracting ribosomes directly to these internal ribosomal entry sites ('IRES').

In all biological domains, the tRNA nuclion structure of five downstream-qualified tRNAs on sense codons (one R-form plus four S-forms) provides excellent codon frame registration with the accuracy of at least fifteen consecutive, stacked and canonical RNA base pairs. This cache of pre-qualified, charged tRNAs is also important for the efficient operation of ribosomes, by building an organized inventory of aminoacylated tRNAs and accelerating their synthesis. Eukaryota may well have evolved a different initiator tRNA link blocking strategy from bacteria as a selective advantage with which to thwart infection. Nevertheless, the stringent stereochemical requirements for nuclion formation, driven by the physics and chemistry of the nuclion's RNA helix, meant that the fundamental tRNA geometry had to be retained.

Protein Synthesis by Nuclions

Our studies of the nucleosides in the tRNA link site indicate that the ancestors of modern nuclions conducted protein synthesis before the advent of ribosomes, with a primordial TLS containing pseudouridine nucleosides at both positions 54 and 55 (this primordial tRNA link site is termed a 'PLS'). Pseudouridine is the only modified nucleoside which can demonstrably be synthesized by RNAs without proteins (it isomerizes from uridine), providing a supportive rationale for the early and critical role of pseudouridine in peptidyl transfer. This insight into early evolution is relevant to today's medicine and several embodiments of the present invention, for example because changes in modern tRNAs which revert the TLS to its ancestral PLS configuration can trigger off-ribosome peptidyl transfer. Such unwanted protein synthesis can lead to perturbations in cellular control and, in certain circumstances, to uncontrolled cellular proliferation and associated disorders such as cancer. In several embodiments of the present invention, an understanding of the origin of protein synthesis by nuclions, before the availability of ribosomes, will assist a person skilled in the art to design, manufacture and use nuclions and ribocapsids for a range of industrial applications.

The critical sequence of events, which transitioned life on our planet from an exclusively RNA world (*The RNA World* by Gesteland et al., Cold Spring Harbor Monograph Series, Third Edition, 2005) to our current biosphere, which is based on the translation of nucleic acids into proteins, likely unfolded as follows (although whether or not the following explanation is accurate does not impact upon the nature, scope or usefulness of the embodiments of the present invention).

In the RNA world, the molecules replicated randomly, leading to complex mixtures of plus and minus RNA strands, in some part complementary. They were degraded quickly, so selective pressure led to RNAs with secondary then tertiary structures to better withstand the environment. Molecules combined in haphazard exchanges. Then, two hairpin structures merged into a larger RNA, an ancestor of modern transfer RNA (Bernhardt et al., 2010, *Biology Direct*, 5:16), which could both replicate and surround itself with a ribocapsid. Nuclions had entered the world.

Later, an unusual conformation in one RNA descendant caused U55 to isomerize to pseudouridine, which enhanced ribocapsid stability by binding an adenosine in the 3'-adjacent RNA. There were no cells at this point, but specialization occurred nonetheless. Within the mixture of RNA molecules, plus and minus strands developed different but synergistic skills, while remaining complementary. The endless transcription of plus strands to minus strands continued, and vice versa. With the increased protection now afforded by ribocapsids, the plus RNA strand in the core of the nuclion progressively grew in length.

It developed ribozymic activity which cut up the newly formed minus strands into multiple ribocapsid RNA segments.

Each long, core plus RNA strand bound several short minus strands by triplet pairing, driven by RNA helix stereochemistry and nuclion thermodynamics, not by any prescient desire for amino acids. All three nuclion conformations formed routinely, with T compressing to S then capping with R. The R-cap was the lowest energy state for a ribocapsid RNA, so, at this stage of evolution, it didn't move once formed. These local RS structures accorded a selective advantage to the nuclions as they increased their stability. The ribocapsid RNAs gradually evolved different characteristics, even though all were programmed by one core strand.

The plus strand RNA soon learned that some minus strand RNAs were better than others at different places in the ribocapsid. A rudimentary genetic code emerged in this core RNA to program ribocapsid binding, using just one or two of the three ribocapsid-binding nucleosides. Darwinian survival pressure led to progressively more sophisticated code which programmed multiple ribocapsid RNAs, precursors of the modern tRNAs but not yet charged with amino acids. The nuclions began to exhibit more structure. By programmed blocking of inter-ribocapsid RNA binding, distinct but linked nuclion segments could be assembled into higher-order structures. Primitive genes and initiation mechanics had begun to evolve. Nonetheless, the primary role of the first nuclion genome was the specification and assembly of ribocapsid RNAs, not amino acids, let alone proteins.

These early nuclions protected their RNA genomes and, later, transported them to locations such as the ocean surface where abundant amino acids bound randomly to the 3' ends of the ribocapsid RNAs. Their descendants learned how to usefully decorate their ribocapsids with amino acids, and, later, attract specific amino acids to individual ribocapsid RNAs. In time, a portion of the nuclion genome logically transitioned from programming ribocapsid RNAs to programming the amino acids attached to those RNAs, in recognition of the increasing contribution of amino acids to nuclion integrity, survival and replication. Most but not all of the ribocapsid RNAs were progressively transitioned to the role of molecular adaptors for amino acids. But, as yet, there were still no proteins.

Then U54 in ancestral tRNA isomerized to pseudouridine and the nuclion was transformed into a helical engine. The nuclion began moving along the RNA genome, while repetitive capping catalyzed the transfer of successive amino acids from one ribocapsid subunit to the next. Initially, the mix of amino acids in the resulting polypeptides passively reflected that of the capsid amino acids. These early polypeptides had little if any biochemical utility, but their electrochemistry and novel structures did improve ribocapsid stability and nuclion thermodynamics. All without needing incremental free energy, as the additional fuel to drive this RNA helical engine had come from aminoacylation in locations such as the ocean surface. Protein synthesis had been born.

Up to this point in molecular evolution, the only life forms were nuclions containing a single RNA molecule within one or more ribocapsids. The RNA genome contained all the data to make ribocapsid RNAs, ribozyme activity to manufacture them, and a program to assemble them. The nuclions worked well for millions of years, but were ultimately limited by Brownian motion which tended to disperse their RNA components. Compartments became necessary. Initially, tiny holes in pumice could have sufficed, or perhaps the peptide decorations held the nuclion at solution surfaces in the ocean. In any event, the RNA genomes needed a new home.

The first programmed proteins likely were simple repeating polymers, rich in amino acids like glycine and alanine to make beta sheet glue and reduce Brownian migration. Later this helpful glue evolved into more sophisticated structural proteins, ancestors of keratin, to better constrain the local environment. Much later, protein enzymes evolved, which, initially, could only operate on macromolecules constrained by the protein glue. Eventually, crude cells developed to reduce the migration of small molecules and enable their biochemical conversion by the evolving enzymes.

The RNA genome in the nuclion was now getting too big and clumsy to accurately preserve all the information it needed for replication, translation and control, while continuing to provide ribozyme services. Once it had moved into its new, cellular home, this pioneering molecule began out-sourcing activities which could be done by others. Two ribocapsid RNAs fused to form the first ribosome (our analysis of the RNA sequence at the peptidyl transfer center of contemporary ribosomes indicates that this PTC evolved from two tRNA-like P-loops, which now serve to align the CCA tails of the tRNAs in the A and P sites). Later, all the programs and data were copied onto a new molecule called DNA, which was good at reproduction and storage but not much else, whereupon the RNA genome assumed the role of messenger RNA. The proteins and other RNAs continued to divide the structural and catalytic work, and collaborated from time to time. Life as we now know it in our biosphere had begun to evolve.

Figure 20:
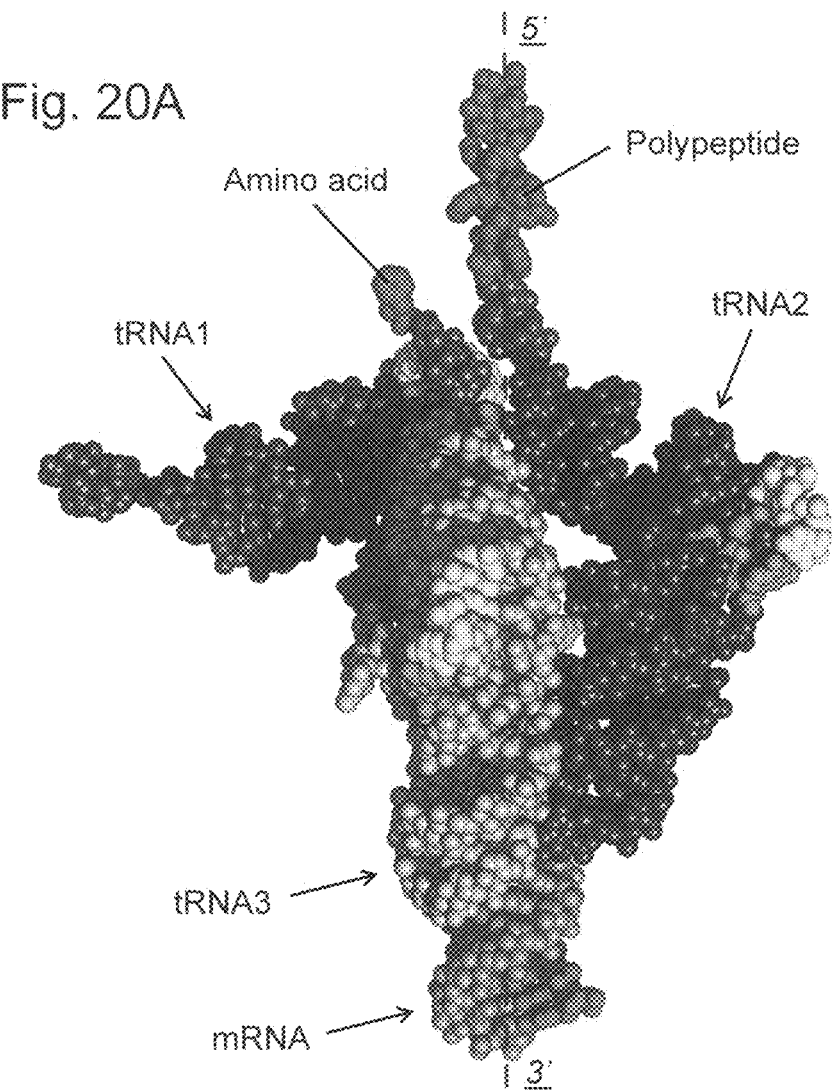
FIG. 20A is a computer model of a primordial (or abnormal contemporary) R-form nuclion tRNA cap (tRNA1) catalyzing peptidyl transfer between the CCA tails of the next two downstream tRNAs:tRNA2 (which holds the growing polypeptide chain) and tRNA3 (which holds the next amino acid). The dashed line is the nuclion axis, marked 5' and 3' to indicate the mRNA direction.
FIG. 20B provides the color key to the nucleotides in FIG. 20A using the abbreviations defined in FIG. 3B.

In one embodiment of the present invention, FIG. 20A is a computer model of peptidyl transfer by three interacting tRNAs at the 5' end of an ancestral, abnormal contemporary, or non-natural nuclion, where at least the capping tRNA T1 has a primordial-type TLS site ('PLS') containing two pseudouridines at positions 54 and 55. FIG. 20B provides the color key to the nucleotides in FIG. 20A using the abbreviations defined in FIG. 3B.

This PLS on the tRNA1 cap is close to the nuclion axis, so that the CCA connectors on the next two tRNAs (tRNA2 and t-RNA3) can bind at the same time to the PLS on tRNA1, configuring the 5' end of this nuclion for protein synthesis. In another embodiment, and in accordance with the schematic drawing shown in FIG. 21, the resulting peptidyl transfer center ('PTC') operated as follows (where 'left' and 'right' refer to the view of the PLS from the aminoacyl stem on tRNA1, with its anticodon stem down):

1. tRNA1 caps the nuclion, positioning the PLS near the nuclion axis;
2. The CCA-peptide on tRNA2 binds to the left side of the PLS;
3. The CCA-amino acid on tRNA3 binds to the right side of the PLS;
4. The growing peptide is transferred from tRNA2 to the amino acid on tRNA3;
5. tRNA2, with no peptide attached, displaces tRNA1;
6. tRNA1 exits the nuclion; and
7. The cycle repeats with tRNA2 as the cap (tRNA numbering increments by one).

Figure 21:
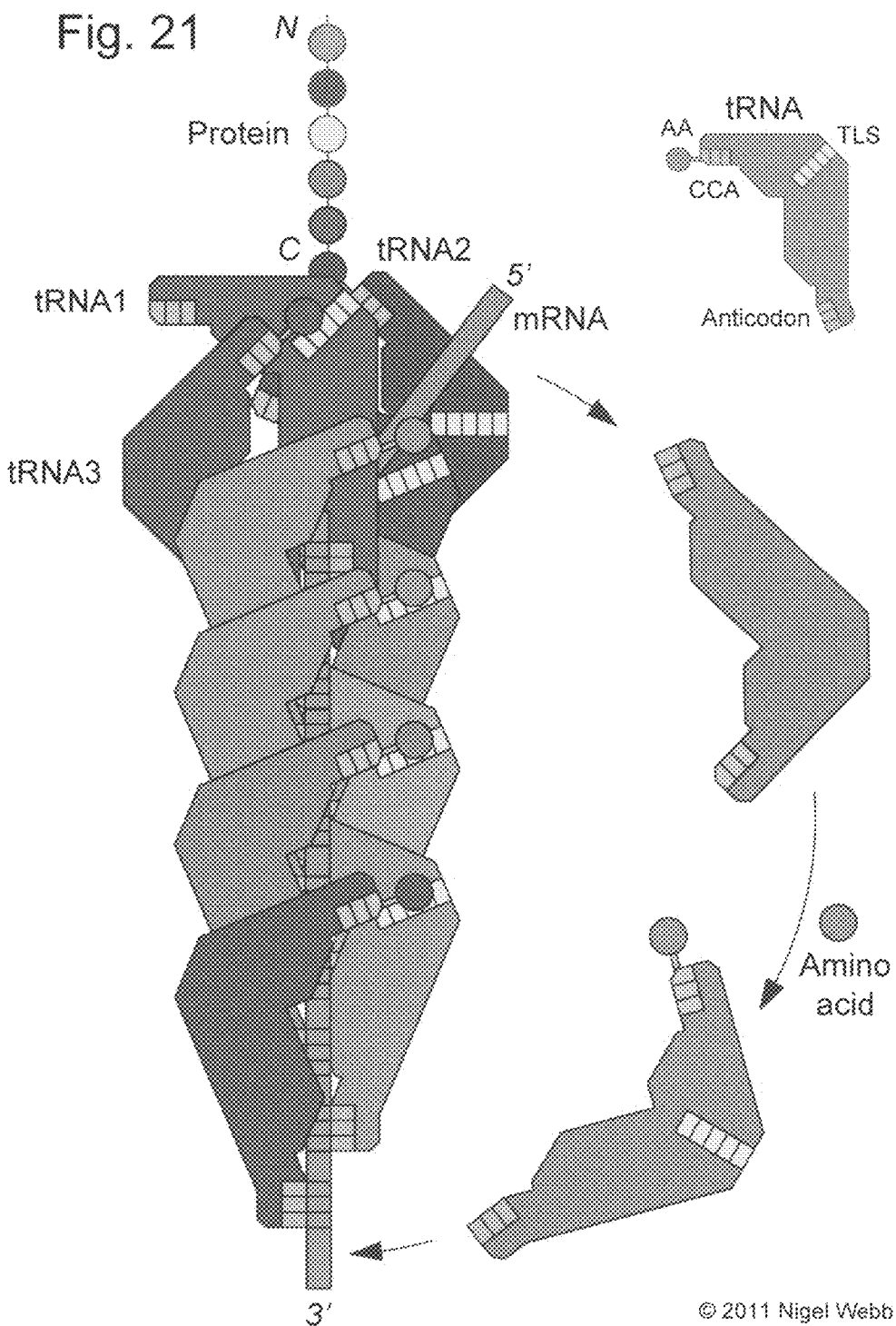
FIG. 21 is a schematic diagram of protein synthesis by a primordial (or abnormal contemporary) compound nuclion containing eleven tRNA molecules, nine of which are aminoacylated, one of which (tRNA2, green) is acylated with the growing polypeptide (marked 'Protein') and one of which, the tRNA cap (tRNA1, red), is not acylated with an amino acid or peptide. Two tRNAs in free solution are shown schematically to indicate free tRNAs being recharged and recycled. The schematic conventions for tRNA are defined in the image displayed in the upper right corner.
Figure 22:
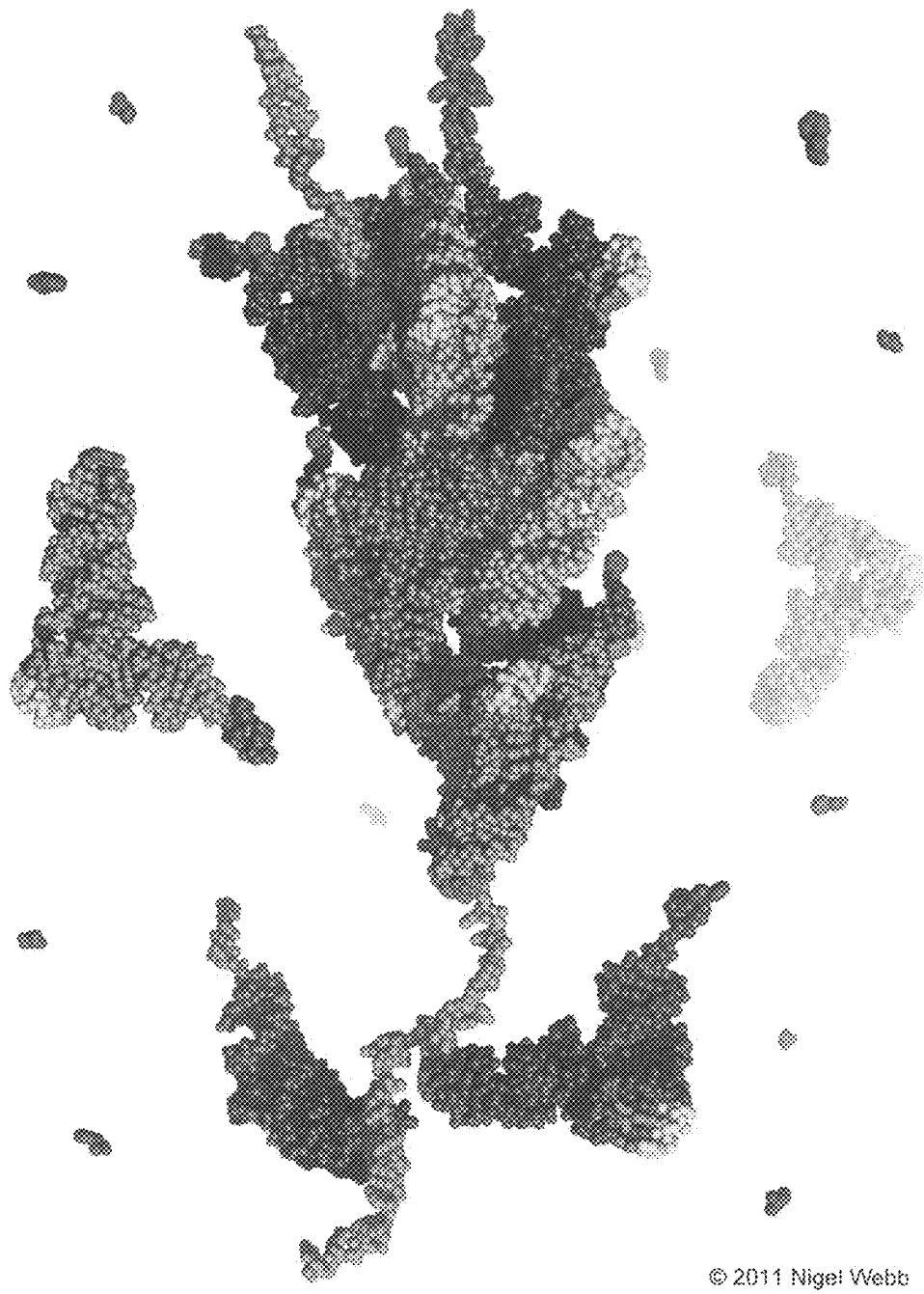
FIG. 22 is a computer model of protein synthesis by a compound tRNA nuclion corresponding to the schematic drawing in FIG. 21, with the addition of two aminoacylated tRNAs on mRNA downstream from the nuclion and an uncharged tRNA in free solution. The small red molecules are amino acids. The polypeptide emerging from the top of the nuclion is red. mRNA is orange.

In one embodiment, FIG. 22 is a computer model of protein synthesis by the primordial (or an abnormal contemporary) nuclion, corresponding to the schematic drawing of FIG. 21. Energy to drive the process comes from the thermodynamic drivers of nuclion transition and the sequential release of high energy bonds connecting the amino acids to their tRNAs. The resulting polypeptide chain is substantially co-axial with the nuclion, and the helical turn for one amino acid in a protein alpha-helix) (100° is (probably not coincidentally) substantially similar to that for each S- and T-form tRNA in the nuclion (~98°). Accordingly, nuclion-driven peptidyl transfer can proceed with minimal if any torsional stress on the mRNA or the growing protein.

In one embodiment, FIG. 23A is a computer model of the peptidyl transfer center in a primordial (or abnormal contemporary) nuclion, in which the left side of the PLS on the R-cap tRNA1 binds the CCA tail of tRNA2 with the growing polypeptide chain PP, and the right side of the PLS on tRNA1 binds the CCA tail of tRNA3 with the next amino acid AA. FIG. 23B provides the color key to the nucleotides in FIG. 23A using the abbreviations defined in FIG. 3B. The black links with round ends between certain nucleosides indicate some of the inter-molecular interactions which contribute to peptidyl transfer. The columns in the table indicate which nucleosides from the three tRNAs align in the six active site layers marked L0 through L5.

The anticodons of all three tRNAs are still bound in canonical form to their respective codons and these three codon-anticodon pairs remained fully stacked on each other within the tight grip of the core nuclion helix. When tRNA2 and tRNA3 bind to tRNA1, their TC-TLS links with other tRNAs are severed. The nine conserved GSP90 nucleosides in the tRNA1 PLS are stacked in five consecutive layers L1 through L5. In this example with yeast tRNA$^{Phe}$, layer 1 contains a naked Watson-Crick base pair C56-G19, which can stack on the amino acid stem of tRNA2, Layer 2 in the PLS is conserved purine R57, which acts catalytically in peptidyl transfer, analogous to the conserved adenosine A2602 in the 70S ribosome. Layer 3 in the PLS is ubiquitous P55 bound by G18 in a Hoogsteen structure; layer 4 is P54 is bound by A58 also per Hoogsteen. Layer 5, which brackets the PLS, is G53-C31, another Watson-Crick pair.

In one embodiment, FIG. 24A shows the six nucleosides in levels 3 and 4 of the quaternary complex formed by the three tRNAs, when viewed from the direction of the pseudouridine stem in tRNA1. When tRNA2 and tRNA3 bind to tRNA1, their 3'-terminal adenosines (A76) bind to P54 and P55, respectively. The ellipse marked 'Reaction' highlights the active site where the amino group in aminoacyl tRNA3 attacks the carboxyl group in peptidyl tRNA2.

In a related embodiment, FIG. 24B shows a closer view of this peptidyl transfer reaction between the two A76 adenosine nucleotides (when viewed from above the PTC) which transfers the growing polypeptide chain from tRNA2 to tRNA3. The ellipse marked 'Reaction' highlights the active site where the amino group in aminoacyl tRNA3 attacks the carboxyl group in peptidyl tRNA2.

FIG. 24C provides the color key to the nucleotides in FIG. 24A and FIG. 24B using the abbreviations defined in FIG. 3B. The black links with round ends between certain nucleosides indicate inter-molecular interactions in layers L3 and L4 which contribute to peptidyl transfer.

In this reaction complex, the P55 triple base-pair (T1: G18-T1:P55-T3:A76) and the P54 triple base-pair (T1:A58-T1:P54-T2:A76) stack on adjacent layers 3 and 4, respectively, within the firm grip of a multistranded RNA stack of 14-plus nucleosides on six levels, amplified by the helix dipole from the coaxial aminoacyl and pseudouridine stems in tRNA1. The substantial quantity of hydrogen bonding, stacking and electrostatic interactions between these three tRNAs drives the formation of the complex. In this quaternary structure, the three tRNAs are precisely aligned for peptidyl transfer. The amino group in aminoacyl tRNA3 can readily attack the carboxyl group in peptidyl tRNA2. Equipped with a PLS containing P54-P55, a tRNA ribozyme in an ancestral nuclion was capable of protein synthesis without proteins or ribosomes, with its tRNA siblings as substrates.

In the TLS of most normal contemporary tRNAs, the pseudouridine at position 54 is replaced with a ribosylthymine, which blocks the binding of A76 in tRNA2 required for peptidyl transfer (see FIG. 25A), as such non-ribosomal protein synthesis is not desirable in modern cells. FIG. 25B provides the color key to the nucleotides in FIG. 25A using the abbreviations defined in FIG. 3B.

In one embodiment, FIG. 25C shows the triple base structure enabled by P54 in the ancestral PLS configuration, which can trigger the binding of T2 by T1. FIG. 25D provides the color key to the nucleotides in FIG. 25C using the abbreviations defined in FIG. 3B. The black link with round ends indicates the inter-molecular base pairing.

Transfer RNA sequences reported to date with P54-P55 constructs include, but are not limited to, tRNA$^{Trp}$ from chicken cells infected with Avian Myeloblastosis Virus (AMV) (Hu et al., 1983, *Nucleic Acids Res.*, 11:4823) and tRNA$^{Pro}$ from mouse cells infected with Murine Leukemia Virus (MLV) (Harada et al., 1979, *J. Biol. Chem.*, 254:0979). Both these viruses are retroviruses.

FIG. 26 is a table of the control logic for nuclion operations and summarizes the states of the left and right TLS sites, driven in part by the nucleosides at positions 54 and 55 in a tRNA T(N), together with the associated and resulting nuclion conditions. T(N−1) refers to the adjacent tRNA immediately upstream of tRNA(N), and T(N+1) refers to the adjacent tRNA immediately downstream of tRNA(N). tRNA (N+2) is the tRNA immediately downstream of tRNA(N+1). In several embodiments, this nuclion logic table is employed to design, develop, manufacture, deploy and use new biopharmaceutical products and services.

TLS Modulation

In several embodiments, natural and non-natural compounds may be employed as agonists or antagonists of particular nuclion structures and activities, inter alia to alter nuclion formation, modulate the associated biological effects, and treat nuclion-mediated medical disorders. These compounds may be designed to bind to, or compete with, nuclion targets in the TLS and/or TC structures, or a sub-set of such structures.

In its role as the original ribozyme site for peptidyl transfer, the ancestral PLS site on the tRNA1 cap was able to bind the CCA tail of tRNA2 (with its growing polypeptide chain) primarily to its left side, while binding the CCA tail of tRNA3 (with the next amino acid) primarily to its right side. The right side of the PLS was also used, as is the right side of TLS is normally used today, for routine links between adjacent tRNA molecules in the ribocapsid. The crucial ability of the TLS-TC interaction to bind adjacent ribocapsid tRNAs explains the substantial conservation of the eight GSP90 nucleosides throughout our biosphere. Comparison of this tRNA sub-structure with the peptidyl transfer site on 23 S RNA in 70S ribosomes indicates that, when nuclions conducted protein synthesis in early evolution, the conserved purine R57 in tRNA may have served as a catalyst for peptidyl transfer. Like ribosomal A2602, this purine is not hydrogen bonded but is located strategically within an RNA helix that originally evolved to hold two A76s from two other tRNAs. In contrast with the protruding ribosomal A2602, however, the R57 seen in tRNA crystal structures is stacked within its parent helix.

In one embodiment, our computer modeling studies indicate that, in normal contemporary nuclion formation, the 3' A76 on a ribocapsid tRNA binds to P55 in the right side of the TLS on the 5'-adjacent tRNA, but the studies did not identify an open TLS site for binding the C74 and C75 from the 3'-adjacent tRNA. The G18 and G19 in the TLS are close to the C74-C75, but they are otherwise engaged in TLS-stack binding, at least in the tRNA crystal structures reported to date, substantially all of which employed polyamines for crystallization. It is likely that these polyamines locked the TLS site into a conformation similar to that exhibited for T2 binding in primordial protein synthesis, thereby preventing contemporary ribocapsid-type T2 binding by the TLS.

Evidence for this polyamine locking of the TLS site comes from X-ray structural studies of tRNA crystals with spermine, one of the polyamines which are usually required for tRNA crystallization (Dock e al., 1984, *Biochem.*, 66:179). FIG. 27A shows the spermine binding site from a high-resolution structure reported for yeast tRNA$^{Phe}$ (Jovine et al., 2000, *J. Mol. Biol.* 301:401), when viewed from the left of the TLS. FIG. 27B is the same structure when viewed from the end of the TLS.

The spermine is bound in large part by nucleosides T54 and P55 on the left side of the tRNA link site, consistent with conformational locking of the TLS. Given the reported flexibility of the tRNA elbow region in solution, such conformational locking may be essential for tRNA crystallization. One unintended consequence of such polyamine locking is distortion of the right side of the TLS normally employed in ribocapsid formation. The TLS likely has one or more alternate conformations not seen in tRNA crystal structures, in which the TLS G18 and G19 bind to C75 and C74, respectively, in the 3'-adjacent tRNA, with the concomitant protrusion of R57 similar to that observed for A2602 in the 70S ribosome. This insight suggests that polyamines such as spermine inhibit ribocapsid formation and their hitherto wide-spread inclusion in laboratory reagents ('to stabilize RNA') probably delayed the discovery of nuclions. In several embodiments of the present invention, polyamines are specifically excluded from predefined manufacturing solutions and reaction mixtures.

Nuclion Target

Some embodiments of the present invention relate to a method for dissociating a nuclion by bringing said nuclion into association with a compound that binds to at least a part of one or more components of said nuclion. In further embodiments, the nuclion sub-structure that binds one or more of such compounds is a nuclion target. In further embodiments, the nuclions and related structures manufactured as described herein may be used to screen compounds which bind to a nuclion target. In some embodiments, the compound employed as an agonist or antagonist of nuclion structure or activity is a nuclion component other than a nuclion component incorporated in the targeted nuclion.

Some embodiments of the present invention relate to a nuclion target comprising a nuclion sub-structure which is operably linked to the prevention, promotion, change, modulation or disruption of the structure, function or activity of a nuclion, wherein (i) a nuclion sub-structure comprises a predefined portion of the structure of a nuclion, its components, or any combination of such components, and (ii) the predefined portion of the structure is selected from the group consisting of a primary structure, a secondary structure, a tertiary structure, a quaternary structure, an R-form structure, an S-form structure, a T-form structure, a combination of any two or more members of this group, and a hybrid of any two or more members of this group. In further embodiments, the nuclion target is selected from the group consisting of a nuclion target not naturally occurring in nature, an isolated nuclion target, a purified nuclion target an amplified nuclion target, a nuclion target separated from cellular components, a nuclion target substantially without other nuclion structure, a nuclion target extracted from other nuclion structure, a nuclion target distinguished from other nuclion structure, and a combination of any two or more members of this group.

In one aspect, the nuclion target is located in or on a nuclion selected from the group consisting of a basic nuclion, an enveloped nuclion, an initiation nuclion, a tRNA nuclion, an enveloped tRNA nuclion, a normal nuclion, an abnormal nuclion, a revertant nuclion, a mutant nuclion, a primordial nuclion, a natural nuclion, a non-natural nuclion, an archaeal nuclion, a bacterial nuclion, a viral nuclion, a plasmid nuclion, a eukaryotic nuclion, a cytoplasmic nuclion, a plastid nuclion, a mitochondrial nuclion, a tRNA nuclion, an enveloped tRNA nuclion, a combination of any two or more members of this group, and a hybrid of two or more members of this group.

In another aspect, the nuclion target, in whole, parts or parts, is the whole, part or parts of a member selected from a the group consisting of connector site, link site, tRNA connector, tRNA link site, anticodon, codon, a connector site bound to a link site, a tRNA connector site and tRNA link site bound together, an anticodon and codon bound together, a connector site and a core nucleic acid structure to which it is bound, a connector site and a core nucleic acid structure to which it is bound, a tRNA connector and the mRNA structure to which it is bound, a tRNA connector and the mRNA initiation structure to which it is bound, a tRNA connector and the Shine Dalgarno structure on the mRNA to which it is bound, a tRNA connector and the Kozak structure on the mRNA to which it is bound, a link site and the core nucleic acid structure to which it is bound, a link site and the core nucleic acid structure to which it is bound, a tRNA link site and the mRNA structure to which it is bound, a tRNA link site and the mRNA initiation structure to which it is bound, a tRNA link site and a Shine Dalgarno structure on the mRNA to which it is bound, a tRNA link site and a Kozak structure on the mRNA to which it is bound, pseudouridine loop, dihydrouridine loop, a pseudouridine loop bound to a dihydrouridine loop, anticodon loop, an anticodon loop bound to a core nucleic acid, CCA tail, P-stack, sub-structure comprising tRNA nucleotides from positions 53 through position 56, tRNA sub-structure comprising nucleotides G53-T54-P55-C56, tRNA sub-structure comprising nucleotides G53-P54-P55-C56, tRNA sub-structure comprising the tRNA nucleotides G53-T54-P55-C56 and G18-G19 and R57-A58 and C61, tRNA sub-structure comprising the tRNA nucleotides G53-P54-P55-C56 and G18-G19 and R57-A58 and C61, a homologue of any one or more members of this group, a combination of any two or more members of this group, and a hybrid of any two or more members of this group.

In another aspect, the means for preventing, promoting, changing or disrupting the structure, function or activity of a nuclion is a means for achieving the effect selected from the group consisting of preventing nuclion formation, slowing nuclion formation, blocking nuclion formation, enabling nuclion formation, promoting nuclion formation, promoting nuclion destruction, promoting nuclion dissolution, accelerating nuclion dissolution, changing nuclion structure, changing nuclion conformation, breaking nuclion structure, modifying nuclion structure, modifying a nuclion component, dissociating one or more nuclion components, inhibiting a nuclion function or activity, enhancing a nuclion function of activity, down-regulating a nuclion function or activity, up-regulating a nuclion function or activity, accelerating a nuclion function or activity, decelerating a nuclion function or activity, interfering with a nuclion function or activity, blocking a nuclion function or activity, enhancing a nuclion function or activity, turning on a nuclion function or activity, turning off a nuclion function or activity, adjusting a nuclion function or activity, competing with a nuclion function or activity, adding a nuclion function or activity, deleting a nuclion function or activity, changing a nuclion function or activity, controlling a nuclion function or activity, a combination of any two or more members of this group, and a hybrid of any two or more members of this group.

In another aspect, the means above for preventing, promoting, changing or disrupting the structure, function or activity of a nuclion is selected from the group consisting of another nuclion, a nuclion component, a physical agent, a chemical agent, a biological agent, an antibody, an enzyme, a ribozyme, a nucleic acid, an antisense compound, an aptamer, an RNA interference agent, a genetic agent, a vaccine, an adventitious agent, a virus, a pharmaceutical agent, a therapeutic agent, a prophylactic agent, a diagnostic agent, a combination of any two or more members of this group, and a hybrid of any two or more members of this group. In some embodiments, the present invention relates to a method to screen for a nuclion target described herein by synthesizing a nuclion or related structure as described herein, contacting the nuclion or related structure with one or more compounds from the library of natural and non-natural nuclion components, and identifying those compounds that bind to and modulate the structure and/or activity of the nuclion or related structure. Specifically, this method may be employed to screen compounds that prevent, promote, modulate, change or disrupt the structure, function or activity of a nuclion. In further embodiments, this method may be performed in vitro to screen for natural and non-natural nuclion components that prevent, promote, modulate, change or disrupt the structure, function or activity of a natural nuclion in vivo. For example, when a nuclion or related structure synthesized as described herein is contacted with an appropriate nuclion component in vitro, the structural conformation of the nuclion or related structure may be disrupted, resulting in a change of the function or activity of the nuclion or related structure.

Elongation Factors Bind to Nuclions

The bacterial elongation factor EF-Tu and its eukaryotic equivalent eEF1A normally deliver aminoacylated tRNAs to the ribosome for protein synthesis (Mateyak et al., 2010, *J. Biol. Chem.*, 285:21209). In one embodiment, our computer modeling studies indicate that these elongation factors bind to certain tRNA nuclions under predefined conditions, consistent with their trucking the aminoacylated tRNAs from the nuclion warehouse to the ribosome factory. These elongation factors also play an important role in controlling and constraining the rate and type of nuclion formation. A nuclion with one or more elongation factors bound to its surface is an example of an 'enveloped nuclion' as taught by several embodiments of the present invention, and the resulting coat of elongation factor molecules is an example of a 'nuclion envelope' as taught by other embodiments.

In one embodiment, FIG. 28 shows a computer model of 12 EF-Tu molecules (marked E1 through E12) bound to 12 tRNAs in a T-form nuclion, generating a protein capsid around the nucleic acid ribocapsid in the nuclion. T12 indicates tRNA12 to which E12 is bound. The computer study indicated that each EF-Tu(N) may also bind to EF-Tu (N+4), where downstream (towards the 3' end of mRNA) is the positive direction. There is no apparent geometric limit to the number of EF-Tu molecules bound to a T-form nuclion (although, in practice, thermodynamic factors limit the number). In contrast, up to four EF-Tu molecules may bind snugly to an S-form nuclion (FIG. 29), but substantially no more, because of interference between EF-Tu(N) and an incoming EF-Tu(N+4). This stereochemical binding limit for EF-Tu in S-nuclions is consistent with the limit of four tRNAs in an S-ribocapsid described earlier from computer modeling studies in another embodiment.

In one embodiment, computer models of the mechanism by which EF-Tu pries each aminoacylated tRNA off the nuclion are shown in FIG. 30A, FIG. 30B, FIG. 30C and FIG. 30D. The model in FIG. 30A and FIG. 30B shows a pre-binding conformation, and the model in FIG. 30C and FIG. 30D shows the post-binding configuration. These models utilize the crystal structure of EF-Tu complex with tRNA$^{Thr}$ as reported in 2WRN (Schmeing et al., 2009, *Science*, 326[5953]:688), and align the amino acid stem of tRNA$^{Thr}$ with that of the 3' tRNA$^{Phe}$ in the S-form nuclion format described earlier. In the pre-binding model, the tRNA$^{Thr}$ is hidden; in the post binding model the tRNA$^{Phe}$ is concealed.

The EF-Tu molecule is entirely located on the outer surface of the nuclion, consistent with its function. When the EF-Tu pries the tRNA off the nuclion, it retracts the aminoacylated CCA from the TLS on the upstream tRNA while simultaneously removing the tRNA anticodon from its mRNA codon (FIG. 30C and FIG. 30D). The EF-Tu molecule attached to the tRNA does not encroach significantly into the TLS on the cognate tRNA, allowing for multiple EF-Tu molecules to bind simultaneously to the nuclion.

In one embodiment, our computer studies indicate that EF-Tu has a second tRNA binding site to lock down a capped nuclion and prevent non-ribosomal protein synthesis with the associated potentially-negative consequences discussed earlier. FIG. 31A, FIG. 31B and FIG. 31C show a view parallel to the nuclion axis of a computer model of how an R-tRNA cap is sandwiched between two EF-Tu molecules on the same nuclion. FIG. 31A shows four EF-Tu molecules (EFTu-2 through EFTu-5) bound to their four cognate tRNAs in an S-form nuclion. FIG. 31B shows the R-tRNA cap (T1) added to this structure; the CCA-AA tail from this tRNA cap sits in a cleft on EFTu-4 (E4) attached to tRNA4. In contrast to the reported first binding site on EF-Tu, this second site binds the right side of the aminoacyl stem of tRNA1, allowing for tRNA1 to be firmly sandwiched between EF-Tu-1 and EF-Tu-4 (FIG. 31C). FIG. 32A, FIG. 32B and FIG. 32C show three views of these same quaternary structures from the 5' direction on the nuclion axis, corresponding to the three structures in FIG. 31A, FIG. 31B and FIG. 31C. These EF-Tu quaternary complexes with the nuclion are compatible with the reported structure and functions of EF-Tu, and are also consistent with an ancestral role of EF-Tu as a protein capsid surrounding the primordial nuclion. An additional benefit of Ef-Tu molecules surrounding the capping tRNA is that they protect and stabilize the labile aminoacyl bond between the amino acid and the CCA tail in this capping tRNA. Absent such protection (and absent interaction with an initiation structure such as a Shine Dalgarno sequence), the aminoacyl bond on the first (most 5') tRNA is exposed and susceptible to hydrolysis, whereas such bonds on other acylated tRNAs in the S-form nuclion are protected by TLS binding.

The concentrations of both tRNA and the elongation factor EF-Tu (or the eEF1A equivalent molecule in eukaryotes) are very high in cells. tRNA is the one of the most prevalent RNA molecules in the cell, normally second only to ribosomal RNA. There is a high level of EF-Tu in *Escherichia coli* cells, frequently comprising 5-10% of the total cell protein, in significant molar excess over the other essential protein components of the translation machinery. Given that tRNA nuclions can bind EF-Tu (or eEF1A, as applicable), most of these nuclions in vivo are coated with EF-Tu (or eEF1A, as applicable) within the cell and provide an example of enveloped nuclions. The fact that most nuclions are normally coated with elongation factor proteins impacts the ways they are isolated from natural sources, according to several embodiments of the present invention. For such enveloped nuclions to be purified, gentle methods known to those skilled in the art have to be employed to retain the binding of this protein coat to the ribocapsid.

In several embodiments, the assembly of a nuclion significantly increases the aggregate molecular weight of the resulting quaternary structure relative to the underlying messenger RNA. For example a mature eukaryotic messenger RNA about 500-600 nucleotides long can have molecular weight of about 170,000. A typical tRNA molecule has a molecular weight in the range 25,000 to 30,000. In one embodiment, when five tRNA molecules are added to this mRNA (in the R and S-conformations) to form a small nuclion, the aggregate molecular weight of the resulting nuclion is about 300,000. If an elongation factor coat of five eEF1A molecules is applied to this nuclion, the derived enveloped nuclion has an aggregate molecular weight in excess of 500,000. In several embodiments, these significant differences in aggregate molecular weight, together with the distinct physical, chemical and electrical properties of these quaternary structures, are leveraged to isolate and purify nuclions and enveloped nuclions from other materials.

Nuclion Symmetry

In several embodiments, the degree and type of symmetry of a nuclion reflect the manner in, and degree to, which its ribocapsid subunits are organized. In several embodiments, the ribocapsid subunits in a nuclion are arranged symmetrically, and such a nuclion is termed a 'symmetrical nuclion'. In other embodiments, the ribocapsid subunits in a nuclion are arranged without symmetry and such a nuclion is termed an 'asymmetrical nuclion'. In some embodiments, the nuclion contains some ribocapsid subunits arranged with symmetry and some ribocapsid subunits arranged asymmetrically; such a nuclion is termed a 'partially symmetric nuclion'. In some embodiments, the nuclion contains ribocapsid subunits with more than one type of symmetry and such a nuclion is termed a 'mixed symmetry nuclion'. In other embodiments, the ribocapsid subunits in the nuclion exhibit symmetries substantially similar to those seen in virions (see the section on viruses), but ribocapsid subunits are mostly nucleic acid whereas viral capsid subunits ('capsomers') are mostly protein. For example, in several embodiments of the present invention, ribocapsid subunits composed substantially of tRNA molecules are arranged in an S-form tRNA nuclion, wherein, in some embodiments, these RNA subunits exhibit helical symmetry around a central axis through the core nucleic acid. In comparison, helical viruses (such as tobacco mosaic virus) are typically composed of substantially identical protein capsomers stacked around an axis in a helical structure which may have a central cavity, a hollow tube, although in such viruses, the viral nucleic acid is not necessarily contained in this tube. In other words, a reference herein to the same or similar type of symmetry does not require or imply that the different components of a structure necessarily have the same or similar spatial relationships with respect to each other.

Different Types of Nuclion

In different embodiments, there are different types of nuclion. In several embodiments, the basic requirement for a majority of functional ribocapsid subunits is that they have the means to bind simultaneously to both the core nucleic acid and another ribocapsid subunit. In practice, for these embodiments, this requires the ribocapsid to possess a molecular configuration and size which is compatible with both these roles. However, in some embodiments, it is not a requirement that the ribocapsid subunit be transfer RNA nor is it a requirement that its structure is similar to that of transfer RNA. Modern transfer RNAs have evolved to fulfill multiple roles substantially beyond those necessary for basic nuclion formation, so tRNAs have certain specialized attributes and associated structural elements, which are not essential for nuclion formation. Furthermore, in some embodiments, it is not essential for nuclion formation that the ribocapsid subunits stack in the same helical direction, nor in the same 5' to 3' orientation, as natural transfer RNA molecules. In several embodiments, ribocapsid subunits can be smaller or larger than tRNA molecules, and have substantially different shapes than tRNAs. While the ribocapsid subunit (ribocapsid unit N) in several embodiments binds to adjacent ribocapsid subunits (N+1 and/or N−1), the ribocapsid subunits in other embodiments bind to non-adjacent ribocapsid subunits (for example: N+2 and/or N−2; N+3 and/or N−3; etc.).

In several embodiments, both the anticodon and the codon are three nucleotides long. However, this length is not a requirement for nuclion formation. In certain embodiments, the length of the anticodon and the codon are more or less than three nucleotides (for example, four nucleotides). Furthermore, in several embodiments, it is not a requirement that the anticodon and codon be composed of natural nucleotides. Indeed, in some embodiments, it is desirable to use non-natural nucleotides in order to confer certain desirable attributes on the resulting nuclions.

In several embodiments, the connector site is a CCA tail, either with or without an amino acid attached. In several embodiments, the link site includes a GTPC sequence. However, neither of these structures is a requirement for the links between ribocapsid subunits. In several embodiments, molecular structures that are substantially unrelated to CCA or GTPC are employed to link ribocapsid subunits. In other embodiments, more than one type of inter-subunit link is employed within the same nuclion.

In several embodiments, the predefined permutations of ribocapsid subunit structures, connection geometries, linking mechanisms, and codon:anticodon interactions generate a plethora of different nuclion structures with a wide range of useful industrial applications.

Materials and Methods for Data Mining and Computer Modeling

In several embodiments of the present invention, the nucleoside data mining studies were conducted using information from the tRNAdb database maintained by Leipzig University in Germany (Jühling et al., 2009, *Nucleic Acids Res.*, 37:D159), although other databases are used in other embodiments. In several embodiments, sequence information was used in preference to genetic information because the former reports the presence of modified nucleosides, although genetic information is employed in other embodiments. In several embodiments, algorithms were written in Microsoft Excel to compute the sequence prevalence ('SP') of each nucleoside at every tRNA location, where the information on each unmodified or modified nucleoside was quarantined separately. SP was calculated as the number of nucleoside occurrences at a particular tRNA location expressed as a percentage of the total number of sequences in the population (623).

In several embodiments, the SP data were allocated and analyzed within the following cohorts when applicable and available: [elongator or initiator] and [archaea, bacteria, eukaryota or virus] and [cytoplasm or organelle]. The SP results were not normalized, because all cohorts were not adequately represented, or, in some cases, not represented at all. Accordingly, the results were unavoidably biased statistically by the disproportionate sequence representation by cohort, reflecting the population of sequences contributed to the tRNAdb database.

In several embodiments, prevalence topograms by cohort were constructed by projecting SP results onto yeast tRNA$^{Phe}$ architecture (PDB: 1EHZ) (Shi et al., 2000, *RNA*, 6:1091), as its structure has been determined in crystal studies by independent laboratories to the highest resolution of any tRNA. Crystal structures were not available for every cohort, so conserved secondary structure was used a guide to tertiary structure conservation, all subject to the exceptions noted earlier.

In several embodiments, the computer modeling studies referenced in this document were conducted using the computer program PyMOL version 1.2r3pre (Schrodinger LLC; *PyMOL* by Surhone et al., VDM Publishing House, 2010), although other software is employed in other embodiments. The structure of yeast tRNA$^{Phe}$ was the architectural platform for most of the models; other tRNAs were substituted or added depending on the context. To facilitate the investigations, amino acids were sometimes added to these tRNAs, using the PyMOL build function.

The following table contains the ten tRNA structures, determined from crystal studies, which were used in this work. The references corresponding to the stated Protein Data Bank ('PDB') IDs are as follows: CW5 and 3CW6 (Barraud et al., 2008, *Nucleic Acids Res.*, 15:4894); 1YFG (Basavappa et al., 1991, *EMBO J.*, 10:3105); 2TRA and 3TRA (Westhof et al., 1988, *Acta. Crystallogr. A.*, 44:112); 1EHZ (Shi et al., 2000, *RNA*, 6:1091), 1EVV (Jovine et al., 2000, *J. Mol. Biol.* 301:401), 2WDK (Voorhees et al., 2009, *Nat. Struct. Mol. Biol.*, 5:528); 1FIR (Bénas et al., 2000, *RNA*, 6:1347); 3A3A (Itoh et al., 2009, *Nucleic Acids Res.*, 37:6259).

TABLE 1 tRNA structures used

| Source | Specificity | PDB ID |
| --- | --- | --- |
| *Escherichia Coli* | Initiator | 3CW5, 3CW6 |
| Yeast | Initiator | 1YFG |
|  | Aspartic acid | 2TRA, 3TRA |
|  | Phenylalanine | 1EHZ, 1EVV, 2WDK |
| Calf | Lysine | 1FIR |
| Human | Selenocysteine | 3A3A |

The structures of the *Thermus Thermophilus* ribosome reported as 2WDG-N (Voorhees et al., 2009, *Nat Struct. Mol. Biol.*, 5:528), 318F-I and 319B-E (Jenner et al., 2010, *Nat. Struct. Mol. Biol.*, 17:555), were employed for the work on the 70S ribosome. The codon-anticodon structure reported in 2WDK for the tRNA in the A site was used for the L-conformation of the anticodon loop. The modeling with *Thermus Thermophilus* EF-Tu used the structures from 2WRN (Schmeing et al., 2009, *Science*, 326[5953]:688).

Given the limited availability of relevant tertiary structures, some consensus computer models were constructed with molecular components from different species. The high degree of conservation of tRNA geometry across biological domains facilitated this approach. The preliminary topographical conclusions from certain key computer modeling were confirmed by building scale models.

Nuclion Manufacturing

In several embodiments of the present invention, nuclions and ribocapsids are manufactured from tRNA molecules and a range of RNA molecules. In a series of manufacturing studies, we assembled such nuclions and ribocapsids, determined their biochemical and biophysical properties, and tested their performance as taught by several embodiments of the present invention.

Example 1: Stability of the Aminoacyl Linkage

In order to determine the stability of the aminoacyl linkages in the charged tRNAs to be used as ribocapsid subunits for tRNA nuclion manufacturing in certain embodiments of the present invention, we measured the rates of hydrolysis for methionine-specific elongator tRNA ('tRNAeMet') at 10° C. and 37° C., and for cysteine-specific tRNA ('tRNACys') at 37° C. The results are shown in FIG. 33, where the y-axes indicate the fraction hydrolysed and the x-axes indicate the time in minutes. The aminoacylated tRNAs (with $^{35}$S-labelled methionine or cysteine) were first prepared as described below in 'Materials and methods for nuclion manufacturing'. The hydrolysis reactions were then carried out at the indicated temperatures in 50 mM Tris-HCl pH 7.5 and 10 mM MgCl$_2$. Reaction aliquots were quenched with formic acid and free amino acid was resolved from aminoacyl-tRNA by electrophoretic separation on a cellulose TLC under acidic conditions. The $^{35}$S-labelled products were visualized by phosphorimaging and quantified using ImageQuant.

The half-life of the aminoacyl linkage on the methionine-specific elongator tRNA under these conditions was approximately 20 minutes at 37° C. (FIG. 33A) and 100 minutes at 10° C. (FIG. 33B). The half-life of the aminoacyl linkage on the cysteine-specific tRNA, under these conditions, was approximately 40 minutes at 37° C. (FIG. 33C). These half-lives are substantially consistent with previously reported data and provide a basis for determining whether nuclion formation increases the stability of the aminoacyl linkage, as predicted by the tRNA nuclion model in several embodiments of the present invention. The half-life of the aminoacyl linkages vary with the type of tRNA and other embodiments of the present invention.

Example 2: Effect of tRNA to mRNA Molar Ratio

In one embodiment, tRNA nuclions were assembled by incubating varying molar ratios of aminoacylated methionine-specific elongator tRNA ('Met-tRNAeMet') with a $^{32}$P-labelled mRNA which contained nine consecutive AUG triplets (the AUG codon is specific for both elongator and initiator methionine-specific tRNAs). The sequence of this mRNA containing methionine codons ('mRNAMet'), with the AUG's underlined, was:

(SEQ ID NO: 1)
5'--GGG-AUG-AUG-AUG-AUG-AUG-AUG-AUG-AUG-AUG-CUU-UCU-AGG-CAC--3'.

Reactions [6 µL in volume with 15 µM native Met-tRNAeMet, 0.0047-3.6 µM $^{32}$P-mRNAMet, and 150 mM MgCl$_2$ in Buffer A (50 mM Tris-HCl pH 7.5, 4% glycerol, 0.05% xylene cyanol, and 0.05% bromophenol blue)] were incubated for 10 minutes at 37° C. or in an ice bath (4° C.). The molar ratio of tRNA to mRNA was adjusted by adding varying amounts of unlabeled mRNAMet to reaction mixtures that contained a fixed amount of $^{32}$P-labelled mRNAMet. Aliquots of 2 µL were added to non-denaturing 12% PAGE gels (8 cm×7 cm×0.8 mm) run at 200 V in 89 mM Tris-borate pH 8.3 buffer with 5 mM MgCl$_2$ until the bromophenol blue dye reached the bottom of the gel. One gel was electrophoresed at room temperature (~45 min, 22° C.) while the other was electrophoresed in a cold room (~80 min, 8° C.). After drying, the gels were exposed to a phosphorscreen for 3.25 hrs and visualized on a Typhoon phosphorimager.

FIG. 34A and FIG. 34B report the results from these gels run at room temperature or in cold room, respectively ('Gel temp'). Each figure shows the effect of different molar ratios of tRNA to mRNA on complex assembly at both 37° C. and in an ice bath ('Rxn temp'). The unbound mRNA migrated as a discrete band furthest down the gel, as confirmed by independent analysis with the mRNA alone (experiment not shown). At least five discrete bands of tRNA:mRNA complexes were visible on the gels ('Complexes 1-5'). Adjacent bands of complexes were substantially equidistant from each other, consistent with polymeric tRNA nuclion structures in which, successive bands contained n+1 additional tRNAs per mRNA. In this embodiment, reactions conducted at 37° C. yielded more nuclions than those carried out at 4° C. and electrophoretic resolution of the individual multimers was better in gels run in the cold room when compared to gels run at room temperature. Different temperature effects are observed in different embodiments of the present invention.

The data in FIG. 34C and FIG. 34D were derived by quantifying the $^{32}$P-labelled bands corresponding to mRNA and complexes 1-5 in FIG. 34A and FIG. 34B, respectively, using ImageQuant. The results show the progressive conversion of free mRNA into polymeric tRNA:mRNA complexes at 37° C. with increasing molar ratios of tRNA to mRNA. At high molar ratios of tRNA to mRNA, substantially all the mRNA was converted into polymeric tRNA nuclion complexes. In this embodiment, non-denaturing gels run in the cold room appeared to preserve the tRNA:mRNA complexes, formed at 37° C., slightly better than comparable gel runs at room temperature. When the gels were run at 8° C., the proportion of retained higher order complexes was higher at increased molar ratios than the proportion seen in gels run at room temperature, where the nuclion assembly in both cases was conducted at 37° C.

The impact of the molar ratio of tRNA to mRNA on the rate and type of nuclion assembly varies with different embodiments of the current invention.

Example 3: Effect of Magnesium Concentration

In another embodiment, the effect of magnesium chloride ($MgCl_2$) concentration on the assembly of nuclion complexes of aminoacylated methionine-specific elongator tRNA with $^{32}$P-labelled mRNAMet containing nine consecutive methionine codons was studied. The molar ratio of Met-tRNAeMet (15.5 μM) to mRNAMet (0.24 μM) was 65. The reactions, which were carried out in Buffer A and supplemented with the indicated concentrations of $MgCl_2$, were incubated for 10 min in an ice bath. Complex formation was monitored by electrophoretic analysis of reaction aliquots in a cold room as described in Example 2. The dried gel was phosphorimaged for 10 hours. FIG. 35A presents the gel image, which again shows the formation of discrete bands of polymeric tRNA:mRNA nuclion complexes ('Complexes 1-5'). FIG. 35B is a graph derived by quantifying the $^{32}$P-labelled bands corresponding to mRNA and complexes 1-5 in FIG. 35A using ImageQuant. FIG. 35C is a graph displaying the data from FIG. 35B below a concentration of 100 mM magnesium chloride.

In this embodiment, the binding of charged tRNA to mRNA is substantially promoted by predetermined increases in the concentration of $MgCl_2$. A $MgCl_2$ concentration substantially in excess of 100 mM is desirable for tRNA nuclion formation under the conditions tested. Different concentrations of $MgCl_2$ are desirable in other embodiments of the present invention.

Example 4: Effects of Aminoacylation Status and Codon Recognition

In another embodiment, the impact of aminoacylation status and cognate versus non-cognate anticodon:codon pairing on nuclion assembly was studied by comparing reactions between methionine-specific mRNA (mRNAMet, with nine consecutive AUG codons) and native Met-tRNAeMet, native deacylated tRNAeMet, and native Cys-tRNACys. The reaction mixtures, which contained 15 μM tRNA and 4.7 nM $^{32}$P-labelled mRNAMet (with a molar ratio of tRNA to mRNA of 3200) in Buffer A with or without 150 mM $MgCl_2$, were incubated for 10 minutes in an ice bath. An aliquot of each reaction mixture was electrophoresed for 80 min at 200 V in a 12% PAGE gel run in 89 mM Tris-borate pH 8.3 buffer with 5 mM $MgCl_2$ in the cold room. FIG. 36 reports the results. The first two lanes in the gel (lanes marked 1) contained $^{32}$P-labelled mRNA but no tRNA. Addition of either native methionine-specific elongator tRNA (lanes marked 2) or aminoacylated methionine-specific elongator tRNA (lanes marked 3) triggered a substantial amount of nuclion complex formation, whereas the addition of aminoacylated cysteine tRNA (lanes marked 4) did not, regardless of the presence or absence of 150 mM $MgCl_2$. In this embodiment, the number and pattern of polymeric bands depends on the aminoacylation status of the tRNA. In the presence of 150 mM $MgCl_2$ and aminoacylated methionine-specific elongator tRNA, the ladder of nuclion complexes exhibits more lower order multimers than the ladder using the native unacylated methionine-specific elongator tRNA. This observation is consistent with the explanation that, in this embodiment, the T-form nuclion can accommodate both charged and uncharged tRNA, but the S-form nuclion can only accommodate charged tRNAs. This explanation supports the nuclion model for this embodiment, in which one of the screening criteria in nature for adding a tRNA to an existing S-form nuclion is that said tRNA must be charged with an amino acid. These results show that, in this embodiment, both charged and uncharged tRNAeMet can form a nuclion on the mRNAMet but that Cys-tRNACys, which does not bind to the AUG codons, cannot. This is consistent with the requirement for specific codon-anticodon interactions in the formation of this type of tRNA nuclion. In other embodiments of the present invention, the degree and type of nuclion formation and the degree of specificity of the codon-anticodon interaction are different from the results described in this paragraph.

Example 5: Kinetics of tRNA Nuclion Assembly

In one embodiment of the present invention, a time course of tRNA nuclion complex assembly at 37° C. was measured using a molar ratio of Met-tRNAeMet to $^{32}$P-labelled mRNAMet (with nine consecutive AUG's) of 3200 in Buffer A with 150 mM $MgCl_2$. At the indicated times (see 'min' on the gel results in FIG. 37) aliquots of the reaction mixture were transferred to a dry ice bath until jointly thawed as a group and loaded onto a 12% PAGE gel for electrophoretic separation (80 min at 200 V in 89 mM Tris-borate pH 8.3 buffer) of the reaction components in a cold room. The resulting phosphorimage shows that while initial tRNA nuclion formation is very rapid (1 min or less) the appearance of higher order structures takes somewhat longer. We note that the reaction course observed here should be interpreted in light of the fact that complex formation can take place during the time required for thawing and loading of samples on the gel. In other embodiments, the kinetics of nuclion complex formation is different from that described in this paragraph.

Example 6: Nuclion Dissociation by an Agent Associating with a Nuclion Target

In several embodiments, natural nuclions and ribocapsids from or in a living organism are modulated, blocked, disrupted or enhanced by administering natural or non-natural substances with a means to achieve a predetermined biochemical, physiological or medical effect. In several embodiments, the administered substance is designed with a means to associate with a specific nuclion target. In several embodiments, the targeted nuclions are dissociated by administering a compound which competes with one or more of the nuclion components, in order to substantially reduce the concentration of nuclions so targeted. In an example of one embodiment, we examined the kinetics of dissociation of predetermined tRNA nuclions, when a compound comprising a means to compete with the nuclions' core nucleic acid was added. This means was a set of multiple codons on an added RNA which was complementary to a set of anticodons on the ribocapsid in the targeted nuclion. In this example, this set of anticodons constitutes a 'nuclion target' and the added RNA is the effective agent.

In this example, a time course for dissociation of the ribocapsid formed between Met-tRNAeMet (15 µM) and $^{32}$P-labelled mRNAMet (nine consecutive AUG triplets; 0.0075 µM) was determined by incubating the preformed complex in the presence of 15 µM cold mRNAMet (the RNA agent) in Buffer A with 150 mM MgCl$_2$ at 37° C. As before, aliquots were removed into a dry ice bath for subsequent electrophoretic analysis in a 12% polyacrylamide gel run for 80 min at 200 V and 8° C. in 89 mM Tris-borate pH 8.3 buffer with 5 mM MgCl$_2$. The resulting phosphorimage (FIG. 38A) and associated time course (FIG. 38B) demonstrate that, in this embodiment, the summed nuclion complexes dissociate with a half-life of approximately 3 min, when a substantial excess of free mRNAMet (1000 times the concentration of core nucleic acid) is present to compete with or displace the mRNAMet in the nuclions. In this example of one embodiment, the added RNA agent rapidly disrupted the nuclions by binding to the ribocapsid anticodons that constitute the nuclion target. In other embodiments, the kinetics of nuclion complex dissociation is different from that described in this paragraph.

Example 7: Molar Ratio Variation with Nuclion Length

In an example of one embodiment, we determined the molar ratios of tRNA to mRNA in a series of tRNA nuclions by preparing a set of fixed-length 42-mer mRNAs that differed in the number of consecutive AUG triplets (i.e., 1, 2, 3, 4, 6, and 9). These mRNAs were 5' end-labeled with $^{32}$P and incubated with 15 µM Met-tRNAeMet for 10 min at 37° C. in Buffer A with 150 mM MgCl$_2$ (the molar ratio of tRNA to mRNA was 200). A phosphorimage of the resulting PAGE gel is shown in FIG. 39A. The number of consecutive AUG triplets in each mRNA is shown at the top of the gel while the apparent molar ratio of tRNA to mRNA in each band is shown on the sides. The results of an Imagequant analysis of this phosphorimage is shown in FIG. 39B. In the accompanying bar graph the fraction of each mRNA in the respective bands is quantified. Based on the resulting patterns we assigned molar ratios to the respective multimeric bands. In this embodiment, the observed molar ratios indicate that the binding of one Met-tRNAeMet to a lone AUG triplet can to some extent promote the non-templated polymerization of additional tRNAs.

Example 8: Core Nucleic Acid is Required for Nuclion Formation

A theoretical but unlikely explanation for some of the polymeric complexes we observed between Met-tRNAeMet and mRNAMet could have been that the tRNA forms higher order oligomers on its own to which the radiolabelled mRNA happens to associate. We ruled out this explanation by analyzing the mobility of a concentration series of $^{32}$P 3' end-labeled Met-tRNAeMet that had been incubated 10 min at 37° C. in Buffer A with 150 mM MgCl$_2$. The concentrations of tRNA ranged from 0.075 to 20 micromolar ('µM' or 'uM'). Reaction aliquots were electrophoresed for 80 min at 200 V in a 12% PAGE gel run in a cold room with 89 mM Tris-borate pH 8.3 buffer and 5 mM MgCl$_2$. A phosphorimage of the resulting gel is shown in FIG. 40. Although bands corresponding to dimer and trimer tRNA species are observed in nearly every lane (consistent with published reports of tRNA dimer and trimer formation), they represent minor components of the total tRNA (15% and 3%, respectively) and do not increase in proportion as the concentration of the tRNA is raised, in contrast to the mRNA-directed formation of nuclions which leads to a well-defined ladder of higher order oligomers. Accordingly, under the conditions of this embodiment, aminoacylated tRNA does not form nuclions in the absence of cognate mRNA as the core nucleic acid.

Example 9: Initiator Nuclion Binds to Shine-Dalgarno Sequence

In an example of one embodiment, we verified the generality of nuclion formation and examined whether fMet-tRNAiMet can recognize the Shine-Dalgarno ('SD') sequence in an mRNA, when the ribocapsid tRNA is bound to this mRNA. It is known to those skilled in the art that the SD sequence occurs in bacteria and, when present on an mRNA, can bind to a ribosome, but there have been no previous reports of the SD sequence binding to tRNA. In eukaryota such as humans, an analogous mRNA sequence involved in translation is the Kozak sequence. However, there are significant differences between the ways in which bacteria and eukaryota employ ribosomes to initiate protein synthesis. Insights into such differences, including those taught by several embodiments of the present invention, can provide medically and commercially important new strategies and tools for designing, manufacturing and using novel pharmaceutical compounds such as antibiotics. The Shine-Dalgarno and Kozak sequences are examples of protein synthesis marker sequences, which serve to improve the efficiency, accuracy and control of translation in cellular organisms.

We prepared an mRNA with the following sequence:

```
                                         (SEQ ID NO: 2)
5'---GGGAAGGAGGUAAAA-AUG-UUU-UUU-UUU-UGC-UUU-UGC-
UAG-GCA--3'
```

In this mRNA, the Shine-Dalgarno sequence (underlined) is separated from the coding triplets by an A$_4$ linker (four contiguous adenosines). In translation this mRNA would specify synthesis of a heptapeptide with the amino acid sequence fMF$_3$CFC (Formyl-methionine, phenylalanine, phenylalanine, phenylalanine, cysteine, phenylalanine, cysteine). After end-labeling with $^{32}$P, this mRNA was incubated for 10 min in an ice bath with various combinations of Met-tRNAeMet, fMet-tRNAiMet, Phe-tRNAPhe, and Cys-tRNACys in Buffer B (100 mM Tris-HCl pH 7.5, 4% glycerol, 0.05% xylene cyanol and 0.05% bromophenol blue) with 150 mM MgCl$_2$. (where fMet-tRNAiMet is initiator methionine-specific tRNA amino acylated with N-formyl methionine; Phe-tRNAPhe is aminoacylated phenylalanine-specific tRNA). Each tRNA was present at 15

µM, resulting in a molar ratio of tRNA to mRNA of 2000. Reactions were analyzed electrophoretically in a cold room as described in Example 8 and a phosphorimage of the gel is shown in FIG. 41. A substantial shift in bands on the gel is seen whenever fMet-tRNAiMet is present. By contrast, a complete set of charged tRNAs in which initiator methionyl tRNA was replaced by elongator methionyl tRNA showed no significant gel shift, implying that fMet-tRNAiMet may specifically interact with the Shine-Dalgarno sequence to stabilize the initiation nuclion and, possibly, help phase the initiator nuclion into the correct reading frame.

Example 10: Effect of Molar Ratio on Initiator Nuclion Assembly

In one embodiment, and using this same radiolabelled mRNA with the sequence coding for fMF$_3$CFC described above, we examined the extent of initiator nuclion formation when the molar ratio of tRNA to mRNA was varied from 10 to 2000. As before, reactions were carried out in Buffer B with 150 mM MgCl$_2$ for 10 min in an ice bath employing 15 µM each of fMet-tRNAiMet, Phe-tRNAPhe, and Cys-tRNACys. FIG. 42A presents a phosphorimage of the electrophoretic analysis of these reactions carried out as described in Example 8. FIG. 42B is a graph of the extent of nuclion formation as function of tRNA:mRNA molar ratio, determined from the phosphorimage shown in FIG. 42A. The binding curve is substantially similar to what was observed when Met-tRNAeMet was incubated with mRNAMet, showing that, for the conditions studied, the kinetics of nuclion assembly were substantially similar. In other embodiments of the present invention, the kinetics of nuclion assembly varies depending on the predetermined conditions.

Materials and Methods for Nuclion Manufacturing

In several embodiments of the present invention, we employed the following materials and methods for our nuclion manufacturing studies, although other materials and methods are employed in other embodiments.

Native transfer RNAs. Methionine-specific elongator tRNA (tRNAeMet) from *E. coli* (1000 pmoles methionine acceptor activity per A$_{260}$ unit) and phenylalanine-specific tRNA (tRNAPhe) from yeast (1000 pmoles phenylalanine acceptor activity per A$_{260}$ unit) were purchased from Chemical Block Ltd., Moscow, Russia. Other native tRNAs (e.g. formylmethionine-specific initiator tRNA, tRNAiMet, and cysteine-specific tRNA, tRNACys) were over-expressed in *E. coli* from an IPTG inducible promoter in pKK223-3 (Liu et al., 2011, *Nat. Commun.*, 2:329). Cultures were maintained for 12-18 hrs after induction to insure sufficient time for post-transcriptional modification of the tRNA and each tRNA was isolated as part of a pool of total tRNA by phenol lysis followed by a series of differential precipitations. The tRNA pools were deacylated by incubation for 3 hrs in pH 9.0 Tris buffer at 37° C. Native tRNACys was further purified by hybridization to a complementary biotinylated oligonucleotide followed by capture on streptavidin-sepharose, washing, and release from the solid support by incubation at elevated temperature (Yokogawa et al., 2010, *Nucleic Acids Res.*, 38:e89).

Aminoacylation. Recombinant His-tagged eMetRS and eCysRS were each expressed at 37° C. in BL21 (DE3) upon induction with 0.4 mM IPTG and were purified using Talon resin, followed by chromatography through a Mono Q column on an Akta FPLC. Enzyme concentrations were measured by Bradford assay with BSA as the standard, and corrected by active site burst assay (Fersht et al., 1975, *Biochemistry*, 14:1). Native tRNACys (90 µM) was aminoacylated with cysteine (180 µM) by incubation with 20 µM CysRS at 37° C. for 10 min in 20 mM Tris-HCl, pH 7.5, 20 mM KCl, 10 mM MgCl$_2$, 25 mM DTT, 2 mM ATP. The reaction was quenched by adding 0.1 volume of 2.5 M NaOAc pH 5.0 and extracted with an equal volume of pH 5.2 phenol-chloroform-isoamyl alcohol (25:24:1). After ethanol precipitation the tRNA was dissolved in 25 mM NaOAc pH 5.0 and stored at −20° C. Charging efficiency was determined by including a small amount of $^3$H-cysteine in the reaction. Following ethanol precipitation an aliquot of the charged tRNA was centrifuged through a Centrispin-20 gel filtration cartridge (Princeton Separations) to insure complete removal of free amino acid and ATP. From the A$_{260}$ and tritium counts of the flow through the fraction of charged tRNA could be calculated. Native $^{35}$S-labelled Cys-tRNACys was prepared by replacing $^3$H-cysteine with $^{35}$S-cysteine in the charging reaction. Charging of native tRNAeMet and tRNAiMet were carried out in similar fashion using MetRS in the presence of $^3$H-methionine or $^{35}$S-methionine. Formylation of Met-tRNAiMet was performed at the same time as aminoacylation by including methionyl formyl transferase and N$^{10}$-formyltetrahydrofolate in the reaction.

Elongator Met-tRNA was 3' end-labeled by incubation of the deacylated tRNA with CCA adding enzyme in the presence of 5 mM CTP and a limiting amount of α-$^{32}$P-ATP. The labeled tRNA was phenol extracted, spun through a Centrispin-20 cartridge, and ethanol precipitated. The recovered tRNA was charged as described above.

Native yeast tRNAPhe was charged using eFx flexizyme in the presence of Phe-CME as described by Murakami (Murakami et al., 2006, *Nat. Methods*, 3:357). Charging efficiency was determined by electrophoresing the aminoacylated tRNA down a 12% denaturing PAGE gel after biotinylation and streptavidin addition as described by the same authors.

Preparation of messenger RNAs. mRNAs were prepared by in vitro transcription using synthetic double-stranded DNA templates which contained a promoter for T7 RNA polymerase. Transcripts were purified by electrophoresis through a 7 M urea denaturing 12% polyacrylamide gel. Bands were visualized by UV shadowing and mRNA was extracted into TE buffer by shaking overnight. mRNA was ethanol precipitated from the clarified supernatant and stored in TE at −20° C. mRNAs were 5'-end labeled by first incubating with shrimp alkaline phosphatase followed by treatment with T4 kinase in the presence of γ-$^{32}$P-ATP or γ-$^{32}$P-GTP. Free counts were removed by ethanol precipitation and centrifugation through a Centrispin-20 cartridge.

Electrophoretic separations. $^{35}$S-Met-tRNAeMet and $^{35}$S-Cys-tRNACys were separated from the free amino acid by electrophoretic TLC on cellulose backed plastic sheets run in pyridine-acetate pH 2.8 buffer (Zaher et al., 2009, Nature, 457:161; Youngman et al., 2004, Cell, 117:589). Nuclions were resolved from $^{32}$P-labelled mRNA by electrophoresis in 12% polyacrylamide gels run in Tris-borate pH 8.3 buffer with 5 mM MgCl$_2$. Analysis of $^{32}$P-labelled Met-tRNAeMet for oligomer formation was carried out using the same gel system. These gels (usually 6.5 cm×8 cm×0.75 mm) were run at 200 V in a cold room or at room temperature until bromophenol blue reached the bottom of the gel. Following electrophoresis the gels were dried onto filter paper under vacuum. $^{32}$P labeled bands were visualized by phosphorimagery and their intensity was determined using Imagequant software. TLC's were analyzed in a similar fashion. For a general overview of the gel electrophoresis methods employed here, see Sambrook and Russell (Sambrook et al., 2001, Molecular Cloning: A Laboratory Manual, Cold Spring Harbor Laboratory, Cold Spring Harbor, N.Y.).

Manufacturing Processes

In several embodiments, nuclions are manufactured: (i) by purifying natural nuclions (the resulting material is termed herein a 'biologic nuclion' or 'biologic nuclions'), or (ii) by assembling nuclions from natural or synthetic components (the resulting material is termed herein a 'synthetic nuclion' or 'synthetic nuclions'). 'Purifying natural nuclions' means isolating nuclions from cellular components with which they are associated when present within cells or cell lysates. In some embodiments, purification can also include preparing a homogeneous preparation of nuclions of the same or substantially the same compositions. In some embodiments, the manufacture of biologic nuclions involves isolating natural nuclions from an organism, biological product, cell culture or fermentation source and purifying them to an adequate extent for their intended use. In some embodiments, the manufacture of synthetic nuclions involves combining a core nucleic acid molecule with ribocapsid nucleic acid molecules. In several embodiments, both biologic and synthetic nuclions are subjected to additional manufacturing steps, including purification and further modification. In several embodiments, the resulting nuclion preparations are homogenous (in which substantially all the nuclions have the same composition) or heterogeneous (containing a mixture of nuclions with different compositions).

In several embodiments, a person skilled in the chemical, biological and pharmaceutical arts for nucleic acids will be familiar with the procedures for isolating or manufacturing the two primary raw materials for the production of nuclions, the nucleic acid molecules for use in the nuclion core and the subunit molecules for use in the ribocapsid (Vomelová et al., 2009, Folia. Biol. Praha, 55:243; Tan et al., 2009, J. Biomed. Biotechnol., 2009:574398). In one embodiment, the core nucleic acid ('CNA') is single-stranded RNA. In another embodiment, single stranded DNA is used. In some embodiments, one or more species of transfer RNA are be used for the ribocapsid subunits. In other embodiments, other forms of nucleic acid may also be used. In several embodiments, the primary, secondary and tertiary structures of the core and ribocapsid subunits are those found in nature, or not, or a mixture thereof. The core and ribocapsid subunits may be extracted from natural sources, produced synthetically, or derived from a combination of natural and synthetic materials. In several embodiments, the core and ribocapsid subunits are chains of natural nucleotides, non-natural nucleotides, modified natural nucleotides, nucleotide analogs, nucleotide substitutes, any combination thereof or any hybrid thereof. In several embodiments, the backbones of the core and ribocapsid subunits are (i) the backbones found in nucleic acids in nature in DNA or RNA, or any combination thereof; (ii) non-natural backbones, modifications of natural backbones, analogs of natural backbones, substitutes for natural backbones or any combination thereof; (iii) any combination of natural and non-natural backbones; or (iv) any hybrid of natural and non-natural backbones. The methods used to make or modify the polymers of nucleotides, their analogs or substitutes, which constitute the raw materials for nuclion production, may employ natural or non-natural processes or any combination thereof.

In the embodiments which employ transfer RNA molecules for the ribocapsid subunits, such tRNA molecules are in a form found in nature, or in a form not found in nature, or a combination, hybrid or mixture thereof. Such natural tRNA molecules include all transfer molecules found in nature, including but not limited to (i) all species of tRNAs with acceptor specificity for any amino acid found in nature in any biological domain or virus or other life form; and (ii) all classes of tRNAs, regardless of whether or not they are initiation molecules to recognize start codons, elongation molecules to contribute additional amino acids, primer molecules for enzymatic activity, or molecules which serve some other function. Non-natural tRNAs include but are not limited to any tRNA molecule which (i) has a length or any portion of its nucleotide sequence different from that of a complete natural tRNA, (ii) includes one or more nucleotides which is different from that found in nature at the same location, (iii) has, in whole or part, a backbone type or modification different from that found in nature at the same location, (iv) has any extension or deletion of one or more nucleotides to or from the sequence of nucleotides found in nature, or (v) has any modification or cross-linking to or between any part of the tRNA molecule not seen in nature at that location. In several embodiments, nuclions are prepared using tRNAs from the species in or for which the nuclion is intended to be used, or species other than the species in or for which the nuclion is intended to be used, or a mixture of tRNAs from different species. In some embodiments, tRNAs for nuclion production are restricted to those found in the species in or for which the nuclion is intended to be used, in order to minimize or reduce the immunogenicity, pyrogenicity or other side effect of the derived nuclion.

In several embodiments, one or more ribocapsid subunit molecules ('RSM'), including but not limited to one or more tRNA molecules, are conjugated with an amino acid, a precursor of an amino acid or a modified amino acid, before the ribocapsid subunits are used to make nuclions. A person skilled in the chemical, biological, and pharmaceutical arts as applied to amino acids and nucleic acids will be familiar with the procedures for isolating, manufacturing and modifying amino acids, and conjugating them or their precursors to nucleic acids. In several embodiments, such amino acids for conjugation are (i) amino acids which are used in nature for protein synthesis ('translation') including but not limited to alanine, arginine, asparagine, aspartic acid, cysteine, glutamic acid, glutamine, glycine, histidine, isoleucine, leucine, lysine, methionine, ornithine, phenylalanine, proline, pyrrolysine, selenocysteine, serine, taurine, threonine, tryptophan, tyrosine and valine (individually and collectively 'standard amino acids'); (ii) 'non-standard' amino acids which occur in nature as a result of post-translation modification or other biological process; (iii) synthetic and modified standard or non-standard amino acids not found in nature; or (iv) a precursor or combination of any of the amino acids in such categories (i), (ii) or (iii). In one embodiment, the amino acid is conjugated to the 3' end of the tRNA and the conjugate is used as a ribocapsid subunit. In another embodiment, the amino acid conjugated to the 3' end of the tRNA molecule is a standard amino acid or its precursor, for which in nature such tRNA molecule is specific (the 'usual amino acid').

In several embodiments, atoms, molecules, macromolecules, polymers or moieties other than the usual amino acid (individually and collectively, 'AA substitutes') are conjugated to one or more ribocapsid nucleic acid molecules (including but not limited to ribocapsid tRNA molecules), in place of, in addition to or in the absence of the usual amino acid. An AA substitute may itself be an amino acid, provided that it is not the usual amino acid. In one embodiment, an AA substitute is covalently attached to the 3' end of a tRNA molecule. In another embodiment, the AA substitute attached to the 3' end of the tRNA molecule is a standard amino acid other than the usual amino acid. AA substitutes may be used inter alia to increase, decrease or modulate the quantity, quality or stability of the links (including but not limited to the TC-TLS links) between adjacent tRNAs in the ribocapsid, and to confer particular attributes on the ribocapsid, the nuclion or both.

In several embodiments, the chemical link used to conjugate the amino acid or an AA substitute to a tRNA is the ester bond used in nature, or any other natural or non-natural ester or chemical bond including but not limited to an amide bond. In one embodiment, this conjugation link is an ester bond between the carboxyl group of an amino acid and the 2' or 3' hydroxyl in the sugar ring of the adenosine nucleotide at the 3' terminal position in the tRNA. In one embodiment, conjugation links are formed using natural enzymes specific for the purpose including but not limited to aminoacyl synthetases (Ibbaa et al., 2001, *EMBO Rep.*, 2:382), or by methods of organic or inorganic chemistry, with or without the use of a dedicated catalyst.

The combination of an unmodified core nucleic acid with unmodified ribocapsid subunits is termed herein a 'basic nuclion'. In several embodiments, molecules and modifications other than those existing in a basic nuclion are added or made to the basic nuclion to change its structure or function or both (whereupon, the resulting nuclion is termed herein a 'complex nuclion'). In several embodiments, such additional molecules and modifications, include but are not limited to (i) the addition of one or more molecules (including but not limited to nucleic acids, proteins, lipids, carbohydrates, polymers, small chemical moieties or other molecules) to bind to a portion of the core nucleic acid molecule not involved in binding ribocapsid subunits, wherein the binding of such additional molecules is achieved by hydrogen bonding, base-pair stacking, covalent bonding, ionic interaction or otherwise); (ii) the addition of a chemical cap to or modification of the 5' or 3' ends of the core nucleic acid molecule (or both such ends), wherein such a cap may be any chemical or material (including but not limited to a methylated guanosine 5' cap, a terminal triphosphate 5' cap or a poly(A) tail at or near the 3' end), which is attached by any means and is intended for any purpose (including but not limited to adjusting the half-life, enzymatic susceptibility or transport of the nuclion or its components); (iii) the conjugation of additional molecules to the ribocapsid nucleic acids, beyond the aforementioned amino acids, their precursors, modifications and substitutes; (iv) the additional treatment of, coating of, or the provision of an envelope for, the nuclion, the ribocapsid or the core nucleic acid by, or a combination of the nuclion with, a natural or non-natural material (including but not limited to a protein, carbohydrate, lipid, cholesterol, nucleic acid, synthetic polymer, liposome, aggregate, dispersant, aggregate, attractant, repellant, adjuvant, fluorescent material, magnetic material, radioactive material, radio-opaque material, metal, cellulose, silica, plastic, or any other organic or inorganic material); (v) the modification of the design or manufacture of one or more of the nucleic acid components in the basic nuclion which result in additional primary, secondary, tertiary or quaternary structure (including but not limited to the introduction of a double helix, triple helix, stem, loop, stem-loop, hairpin, pseudoknot, tetraloop, riboswitch, ribozyme, polyadenosine sequence, Shine-Dalgarno sequence, or Kozak sequence); and (vi) the connection, inclusion, incorporation, introduction, mixing, association or co-administration of additional molecules or molecular components which impact or act in co-operation with the structure or function of a nuclion, including but not limited to single-stranded RNA, double-stranded RNA, coding RNA, non-coding RNA, messenger RNA, introns, exons, transfer RNA, ribosomal RNA, ribozyme RNA, antisense RNA, sense RNA, nonsense RNA, regulatory RNA, microRNA, small interfering RNA, small nuclear RNA, small nucleolar RNA, spliceosome, single-stranded DNA, double-stranded DNA, combination of DNA and RNA, aptamer, intercalating material, virus, viral component, viral RNA, viral DNA, protein, enzyme, histone, antibody, initiation factor, elongation factor, termination factor, translation factor, lipid, carbohydrate, control compound or any other biochemical, chemical or inorganic atom, element, molecule, compound, material or precursor to any molecule listed in this paragraph; or (vii) any combination, hybrid or mixture of the molecules or modifications set forth in the preceding phrases (i) through (vi).

In several embodiments, complex nuclions have, but are not limited to, one or more of the following properties:
(i) The core nucleic acid used to make the nuclion is a single-stranded RNA molecule with a chemical cap at the 5' end;
(ii) The core nucleic acid used to make the nuclion is a single-stranded RNA molecule with a chemical cap at the 3' end;
(iii) The core nucleic acid used to make the nuclion is a single-stranded RNA molecule with a poly(Adenosine) tail at the 3' end, which is optionally further modified to resist degradation and improve nuclion performance;
(iv) The core nucleic acid used to make the nuclion is a single-stranded RNA molecule with a chemical cap at the 5' end and a poly(A) tail at the 3' end;
(v) The core nucleic acid is a single-stranded RNA molecule designed with a self-annealing hairpin loop at the 5' end to improve stability and nuclion performance;
(vi) A core RNA molecule is partly enclosed by ribocapsid subunits, and the remaining core nucleic acid molecule is not bound to ribocapsid subunits;
(vii) A core RNA molecule is partly enclosed by ribocapsid subunits, and the remaining core nucleic acid molecule contains one or more 'smart RNA components', embodiments of which include but are not limited a ribozyme, riboswitch, aptamer, spliceosome, poly(A) sequence or any other RNA component or structure which has a biological effect;
(viii) A core RNA molecule is partly bound to ribocapsid nucleic acids, and one or more other nucleic acid molecules complementary to part or all of the remaining core nucleic acid are bound to said remaining core nucleic acid;
(ix) A core RNA molecule is partly bound to ribocapsid subunits, and one or more other nucleic acid molecules complementary to part or all of the remaining core nucleic acid is bound to it, wherein this other RNA molecule contains one or more smart RNA components; or
(x) The core nucleic acid or one or more of the ribocapsid nucleic acids are labeled with a radioactive or radio-opaque material before or after nuclion manufacture.

Nuclion Design Factors

In several embodiments, the raw materials selected for nuclion manufacturing, the core nucleic acid and the ribocapsid nucleic acids (whether or not modified as set forth above), must substantially comply with the following acceptance criteria: (i) the core nucleic acid molecule ('CNA') must include, as a portion or all of its structure, a region with multiple binding sites ('codons') with which to bind ribocapsid nucleic acids; (ii) all the ribocapsid subunits must include at least one binding site ('anticodon') to bind to a codon on the CNA; (iii) most of the ribocapsid subunits must include at least one ribocapsid link site (LS) to bind to a ribocapsid connector site (CS) on an adjacent ribocapsid subunit bound to the same CNA; and (iv) most of the ribocapsid subunits must include at least one CS to bind to an LS on an adjacent RNA on the same CNA.

In several embodiments, substantially all the ribocapsid subunits in a given nuclion are bound to the core nucleic acid, but not all the ribocapsid subunits are necessarily bound directly to adjacent ribocapsid subunits in both directions on the core nucleic acid. In one embodiment, as exemplified in the schematic drawing of a nuclion with four ribocapsid subunits in FIG. 1, the leftmost ribocapsid subunit R1 only binds directly to one ribocapsid subunit (R2) and the rightmost ribocapsid subunit (R4) only binds directly to one ribocapsid subunit (R3), whereas ribocapsid subunits R2 and R3 each bind directly to two ribocapsid subunits. In some embodiments, a ribocapsid subunit may not be bound to another ribocapsid subunit via the CS-LS link. In one embodiment, as exemplified in the model of an R-form tRNA in FIG. 14A and the schematic drawing of a tRNA nuclion in FIG. 15, a nucleic acid molecule which caps the ribocapsid in a nuclion is not be directly linked to another ribocapsid subunit, although it does remain bound to the same core nucleic acid.

Figure 18:
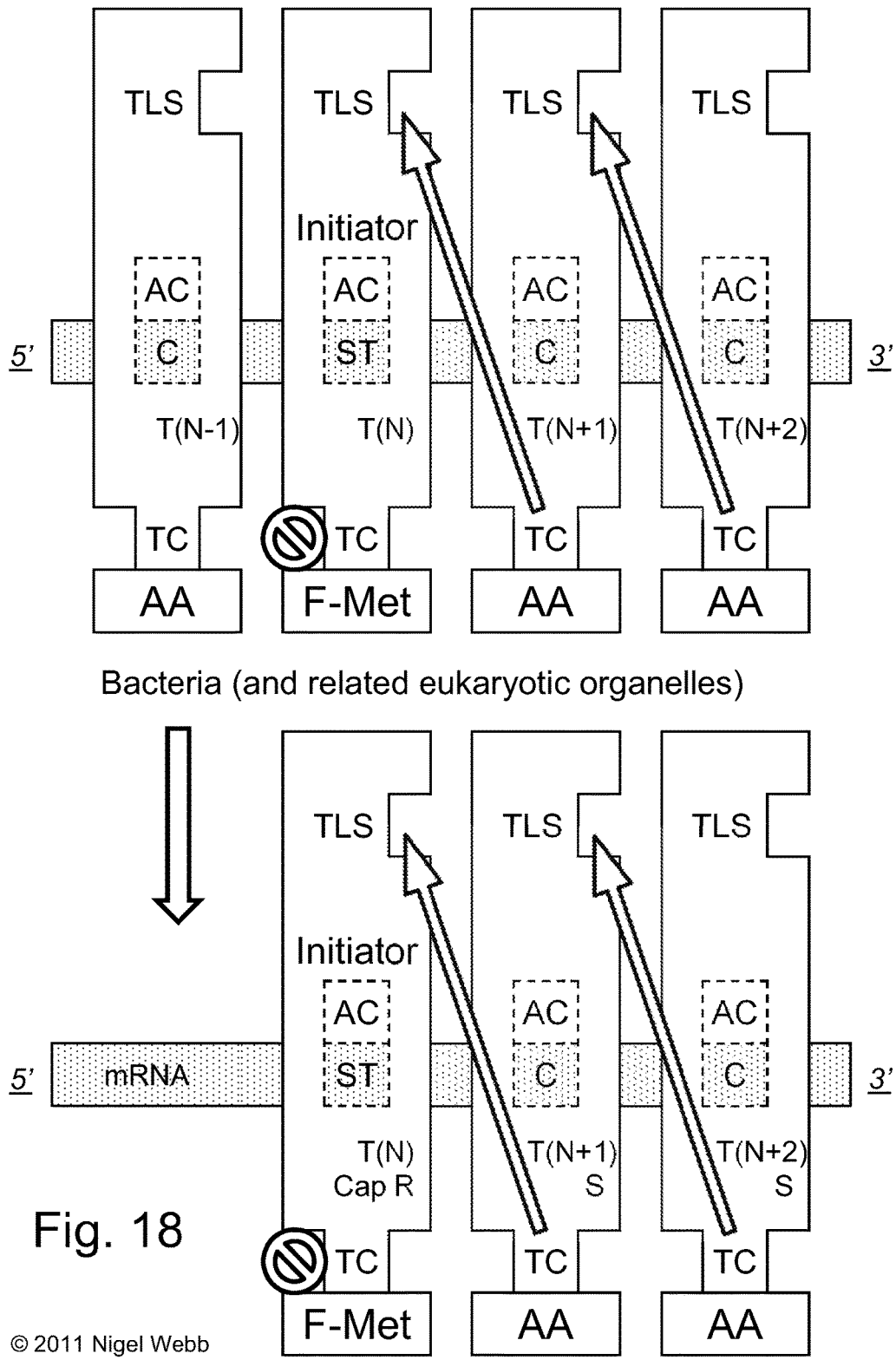
FIG. 18 is a drawing of initiation (start) codon marking by tRNAs in bacteria and related eukaryotic organelles, before (upper) and after (lower) the formation of an initiation nuclion. T(N−1) through T(N+2) represent tRNA molecules. AA represents an amino acid attached to an elongator tRNA. F-Met (formyl methionine) is attached to the initiator tRNA. 5' and 3' mark the direction of the ends of the mRNA. C represents a codon on the mRNA. AC represents an anticodon on a tRNA. R and S indicate the nuclion conformation at that tRNA. The angled arrows indicate the binding of a tRNA connector (TC) on one tRNA to a tRNA link site (TLS) on another tRNA. The 'no parking' sign indicates that the TC connector cannot bind to the TLS site on the adjacent upstream tRNA.

In several embodiments, CS-LS links are blocked or disrupted by design, in order to modify the structure or function of a nuclion, as exemplified in the schematic drawings of FIG. 18. In some embodiments, upstream and downstream blocking of CS-LS links (equivalent to TC-TLS links in tRNA nuclions) is utilized to mark start codons at translation initiation sites on messenger RNA. In an embodiment of an upstream block, the amino acid on the initiator tRNA is formylated to prevent connection with its 5' neighbor, thereby forcing the initiator tRNA into the R-form cap position and marking the start codon for protein synthesis. In an embodiment of a downstream block, the LS (TLS in tRNA nuclions) site on the initiator tRNA is modified, in order to prevent binding of the CS (CT in tRNA nuclions) on the 3'-adjacent tRNA, thereby forcing this neighbor into the cap position.

In several embodiments, nuclions are assembled with a wide range of structures, and a single nuclion structure may comprise one or multiple ribocapsid conformations. In one embodiment, exemplified by the design of a nuclion containing multiple nuclion conformations (a 'compound nuclion') provided in FIG. 16, three different nuclion conformations are shown combined to form an integrated tRNA nuclion structure. In this example of a compound nuclion, an R-form tRNA caps the 5' end of the nuclion, four S-form tRNAs bind together to form the mid-section, followed by a series of T-form tRNAs on the 3' side of the nuclion. Two additional aminoacylated tRNAs are shown bound to the mRNA downstream from the nuclion.

In one embodiment, FIG. 17 summarizes the properties and dimensions of the three nuclion conformation in this example of a compound tRNA nuclion. In another embodiment of a compound nuclion, multiple sections of contiguous ribocapsid on a single core nucleic acid are separated with structural breaks. In one embodiment, these breaks are accomplished through the selection of particular ribocapsid subunits (such as bacterial initiator tRNAs aminoacylated with formyl methionine) to bracket these nuclions sections. The CS or LS sites in these bracketing ribocapsid subunits are blocked in order to prevent continuation of the ribocapsid structure at those locations.

In several embodiments of the present invention, nuclions are assembled from core nucleic acid and ribocapsid nucleic acids using batch, continuous or other processes known to a person skilled in the pharmaceutical, chemical and biological arts to be suitable for the formation of nucleic acid complexes, provided that the methodologies, reagents and solutions employed do not denature nucleic acids and, in the event any of the raw materials is modified, does not alter or remove such modification. In several embodiments applicable to the manufacture of RNA nuclions, solutions of core RNA and ribocapsid nucleic acids (including any modifications thereto) are prepared and mixed, such that (i) the molar concentration of each species of ribocapsid nucleic acid is in excess of (ii) the number of corresponding codons on the core RNA multiplied by the molar concentration of the core RNA.

In several embodiments, the assembled nuclions are then separated from the unbound raw materials and purified by any of the standard biochemical or biophysical methods for nucleic acid fractionation known to a person skilled in the art (including but not limited to adsorption, affinity fractionation, centrifugation, chromatography, crystallization, dialysis, electrolysis, electrophoresis, enzyme treatment, evaporation, filtration, ultrafiltration, gel separation, magnetic separation, minicolumns, pH separation, temperature change, salt gradient, solvent gradient, temperature gradient, precipitation, solid phase separation or solvent fractionation).

In several embodiments of the manufacturing, separation and purification procedures for nuclions, conditions are employed which are sufficiently non-denaturing for nucleic acids to maintain and maximize nuclion integrity. In several embodiments, the solutions employed for the manufacture, separation and purification of nuclions have sufficiently low amounts of compounds to not interfere with intermolecular binding within the nuclion, including but not limited to sufficiently low levels of compounds which interfere with one or more (i) LS-CS links between adjacent tRNAs in the nuclion (in one embodiment, such interfering compounds relevant to tRNA nuclions include but are not limited to polyamines such as spermine and spermidine); (ii) codon-anticodon links between the ribocapsid nucleic acids and the core nucleic acid (in several embodiments, examples of such interfering compounds include oligonucleotides which are complementary in whole or part to the codon or anticodon); or (iii) links in a complex nuclion between any of the added molecules and the core nucleic acid or a ribocapsid nucleic acid.

In several embodiments, nuclions are designed and manufactured to contain a wide variety of information in their component nucleic acids including but not limited to DNA information, RNA information, viral Information or a combination thereof (individually and collectively, termed 'nucleic information' herein). In one embodiment, the nucleic information is stored in, on or with the core nucleic acid molecule. In another embodiment, nucleic information is stored in, on or with one or more ribocapsid subunits. In another embodiment, nucleic information is stored both in, on or with one or more ribocapsid subunits and in, on or with the core nucleic acid.

In several embodiments, tRNA nuclions are manufactured by first synthesizing a single-stranded core RNA molecule with a specific nucleotide sequence containing the nucleic information needed for a particular application. This CNA is then treated with charged tRNA molecules with anticodons which bind to consecutive triplets of nucleotides on the CNA, regardless of whether or not such triplets represent a valid sequence of codons in nature. The unbound tRNAs are then separated, leaving completed nuclions in which the nucleotide sequence on the CNA is holding nucleic information for a later biological function while simultaneously providing binding sites for the ribocapsid RNAs. In another embodiment, the first (most 5') nucleotide triplet on the CNA to bind a tRNA is an initiator sequence (including but not limited to the sequence AUG), which binds an initiator tRNA molecule.

In several embodiments, packaging the nucleic information in a nuclion can protect this information and facilitate its delivery to its intended target, not unlike the packaging of a viral genome within a viral capsid, although the nuclion capsid is composed substantially of nucleic acid whereas the viral capsid is composed substantially of protein. In several embodiments, packaging of nucleic information in nuclions can offer significant advantages compared to packaging nucleic information in virions. For example, nuclions containing ribocapsid subunits such as transfer RNA can be substantially less immunogenic than virions, in part because the protein capsids used by viruses generally elicit a substantially stronger response by cellular and humoral immune systems in higher organisms such as man. This immune response can lead to the destruction or diminution of the virus and its genomic nucleic information, whereas the nuclion is better able to avoid such host defense systems in what can be described as a 'Trojan horse' delivery approach. In this embodiment, the host treats the administered ('non-self') nuclion as if it is host ('self') material, and permits at least a portion or a substantial portion of its nucleic information to be delivered. In some embodiments, the nucleic acid in a tRNA nuclion is presented to the targeted cell in a form that facilitates subsequent processing and activation of the embedded nucleic information. In certain embodiments, the targeted cell views the nuclion structure as a normal part of the cellular process, and therefore acts on them to translate (in some embodiments), to transcribe (in some embodiments) or otherwise (in other embodiments) implement the embedded nucleic information.

In some embodiments, a nuclion is manufactured such that the core nucleic acid is only partly encapsulated with a ribocapsid, leaving one or more portions of the core nucleic acid without a shell. In one embodiment, this strategy is adopted when inter alia it is desired that a portion of the core nucleic acid be available for interaction with other molecules or cellular components. In another embodiment, the portion of core nucleic acid outside the nuclion shell serves as, or has attached to it, an aptamer to bind to a cellular target, thereby delivering the nucleic acid within the shell, which, in a related embodiment, is activated upon arrival at the target. In another embodiment, the portion of core nucleic acid outside the ribocapsid shell is single-stranded RNA which is bound prior to administration to another RNA molecule to form a substantially double-stranded RNA structure outside the shell. In one embodiment, this double-stranded RNA is of a length, configuration and modification status to function as interfering RNA. In several embodiments, the shell around the balance of the core nucleic acid serves as a delivery vehicle for the whole nuclion, thereby facilitating the targeting of the interfering RNA to its intended target. In another embodiment, the core nucleic acid outside the ribocapsid shell is an antisense oligonucleotide designed to modify cellular behavior, while the nuclion structure enhances the stability of the active ingredient and increases drug delivery to the desired tissue.

Manufacturing Considerations

There are a number of factors which affect the efficiency and yield of nuclion isolation and synthesis. In several embodiments, an important manufacturing consideration for certain types of nuclion is the stability of the core nucleic acid core and the ribocapsid nucleic acids being used as raw materials.

In several embodiments, the bond between the tRNA molecule and the attached amino acid in an aminoacyl (charged) tRNA may have a half-life in free solution of only 20-30 minutes under certain circumstances (Piltz et al., 1997*, Nucleic Acids Res.,* 125:1862), whereupon the amino acid is liberated. In one embodiment, the manufacturing process employed for the production of tRNA nuclions, in which an aminoacylated tRNA tail is a connector site, is completely sufficiently quickly in order to achieve an economically reasonable yield of aminoacylated tRNA molecules incorporated into completed nuclions. In several embodiments of tRNA nuclions made from aminoacylated tRNAs, the growing nuclion will tend to discriminate against uncharged tRNA molecules without an amino acid, so the purity of such a tRNA nuclion is not substantially reduced, despite an overall yield reduction, provided that sufficient qualified aminoacylated tRNAs remain to properly complete the nuclion assembly. In several embodiments, once these aminoacylated tRNAs have been incorporated into a nuclion, the aminoacyl bond held by a link site on an adjacent tRNA is stabilized and the half-life of the aminoacylated tRNA is greatly extended. In some embodiments, however, the aminoacyl bond on the first (most 5') tRNA in a ribocapsid segment is not normally so protected, so its half-life remains relatively short unless and until it is stabilized in some other manner, for example in one embodiment, by binding to an mRNA structure, such as but not limited to the Shine-Dalgarno sequence. In nature, initiation factors and certain mRNA structures can provide such stabilization. In one embodiment of nuclion manufacturing, where the amino acid needs to be retained on the first tRNA (which is not always the case) an alternate linkage (including but not limited to an amide linkage) is employed.

In several embodiments relating to nuclion manufacturing, the core nucleic is first substantially bound to a solid phase support (by methods including but not limited to adsorption, absorption, avidin-biotin binding, hapten-antibody binding, covalent linkage, ionic linkage or any other procedure which substantially immobilizes the core nucleic acid on such support). The ribocapsid nucleic acids are then added to substantially bind to the core nucleic acid and ribocapsid nucleic acids not bound to the core nucleic acid are subsequently and substantially removed. Finally, the assembled nuclions are substantially removed from the solid phase. Persons skilled in the biochemical, biological, pharmaceutical and chemical arts are familiar with the methods employed for the administration, adsorption, conjugation, elution and fractionation of nucleic acid molecules and complexes thereof to, from and on such solid phase materials. In one embodiment, biotin is connected or bound to the core nucleic acid and a streptavidin column is used as the solid phase support. In a related embodiment, a core nucleic acid is first prepared with a photocleavable biotin group attached to its 5' end, by conducting transcription of this RNA in the presence of a biotin-modified GMP derivative that is a substrate for T7 RNAP; the nuclions are assembled, then the reaction mixture is applied to streptavidin-sepharose, washed, and the purified nuclions are released from the solid support by exposure to a predetermined amount of light at the correct wavelength. In another embodiment, a hapten molecule is connected or bound to the core nucleic acid and a monoclonal antibody specific for the hapten is bound to the sold phase support. In another embodiment, a monoclonal antibody specific for the core nucleic acid is bound to the sold phase support.

In several embodiments, solid phase materials employed for such nuclion assembly are natural or non-natural materials including but not limited to silica-based and silica-coated material, ion exchange material, benzoylated DEAE cellulose, resin, plastic, metal, hydroxyapatite, magnetic materials, glass, plastic, nylon, cellulose, gels, Sepharose, agarose, streptavidin column and modified constructs of such materials). Methodologies employed for such solid phase assembly of nuclions include but are not limited to batch chemistry, centrifugation, column chromatography, magnetic separation, temperature gradient, solvent gradient, salt gradient, pH gradient, electrophoresis, filtration or any other method which separates unbound material from material bound to the solid phase or vice versa.

In one embodiment of solid phase nuclion assembly, the core nucleic acid is isolated or manufactured to include a poly(A) sequence, preferably but not necessarily at or near the 3' tail of the core nucleic acid. The solid phase is a resin to which oligo(dT) oligomers of deoxythymidine have been attached, such that substantially only the RNA having a poly-A tail will bind to the resin (Aviv et al., 1972, *Proc. Natl. Acad. Sci. U.S.A.*, 69:1408). This resin is loaded with the core nucleic acid, then exposed to a solution or solutions of ribocapsid nucleic acids (for example, but not limited, to nucleic acids such as tRNAs and aminoacylated tRNAs). The unbound ribocapsid nucleic acids are separated from nuclions bound to the resin by elution, centrifugation, magnetic separation or other means. The nuclions are then released from the resin by adjusting the chemical or physical environment of the resin, or by introducing molecules such as oligonucleotides which displace the nuclions from their binding sites on the resin. Chromatography on an oligo(dT) cellulose column is one embodiment of the large-scale preparation of nuclions assembled from core nucleic acid which contains a poly(A) sequence. It should be noted that the messenger RNAs in the cytoplasm of most eukaryotes have a poly(A) tail, whereas the mRNAs in bacterial cells and related organelles in eukaryotes do not. Accordingly, the use of such oligo(dT) columns is one embodiment for the preparation of nuclions and ribocapsids for use in eukaryotic organisms such as animals and humans.

In several embodiments, a polynucleotide is synthesized which is complementary to a portion of the core nucleic acid ('CNA') that is not intended for ribocapsid formation (a 'CNA probe'). Then the CNA probe is immobilized on a solid phase support or other separation device, after which the core nucleic acid is applied to the support or device, leaving exposed the binding sites for the ribocapsid subunits. Unbound core nucleic acid is removed, the ribocapsid subunits are applied to the column to form nuclions, then unbound subunits are removed. Finally, the assembled nuclions are eluted by disrupting the bonds between the CNA and the CNA probe, using a method which retains the integrity of the nuclions. In one embodiment, biotin is conjugated to the CNA probe. The CNA probe conjugated with biotin is then immobilized on a streptavidin column. The core nucleic acid is then applied to the column, whereupon a portion of the CNA binds to the CNA probe. The ribocapsid subunits are then applied to the column, whereupon the assembled nuclions are retained by the solid phase. Finally, the assembled nuclions are eluted from the column by severing the bonds between the CNA and the immobilized complementary polynucleotide. In several embodiments, the use of a CNA probe to indirectly immobilize the CNA provides a valuable alternative to directly immobilizing the CNA, in part because use of the former method permits final step elution with different methods than those employed for the latter.

In another embodiment applicable to the isolation and purification of assembled nuclions, a column is prepared in which an elongation factor such as EF-Tu or eEF1A is linked to a solid phase matrix, in accordance with the methods of Chinali (Chinali, 1977, *J Biochem. Biophys. Methods,* 34:1). The EF-Tu (or eEF1A) molecules immobilized on the solid matrix bind to the tRNA molecules in the ribocapsid shell of the nuclion, and enable the separation of nuclions from other materials. In one embodiment, and provided that tRNA molecules not bound in nuclions are first removed from the mixture by methods known to those skilled in the art (for example, by Sephadex gel filtration in a column), the EF-Tu (or eEF1A) columns provide a useful method of separating nuclions that are not enveloped.

Given that there is a high concentration of certain elongation factor proteins within cells, such as EF-Tu (in bacteria and related organelles in eukaryota) and eEF1A (in the cytoplasm of eukaryota), in several embodiments a substantial fraction of nuclions isolated from natural sources may be enveloped by such proteins. In several embodiments, special steps are incorporated in the procedures when isolating nuclions from natural sources to address these enveloped nuclions when present. In one embodiment, the higher molecular weight enveloped nuclions are first separated from the unbound lower molecular weight elongation factors (for example but not limited to, by gel filtration, centrifugation or precipitation). In one embodiment, this higher molecular weight fraction is then applied to a column containing a solid-phase support to which monoclonal antibodies specific for the applicable elongation factor (including but not limited to EF-Tu or eEF1A) have been previously conjugated. Conditions are selected which cause the enveloped nuclions to bind to the antibodies on the column, and the impurities are washed out of the column. By then applying a change in the chemical, pH, temperature or other conditions of the column, the enveloped nuclions are detached from the monoclonal antibodies and harvested from the column.

In several embodiments of nuclion purification, electrophoresis is used to separate nuclions and enveloped nuclions from other materials. Several examples of such uses of electrophoresis are provided in the section entitled 'Nuclion manufacturing'. In several embodiments, such electrophoretic methodologies are combined with other techniques, including but not limited to temperature gradients to improve the degree of separation of the nuclions from other materials.

Another important consideration for nuclion assembly is the susceptibility of RNA to nucleases. In one embodiment, when nuclions or enveloped nuclions are isolated from natural sources, they are processed in order that ribonucleases are inactivated rapidly, using methods familiar to persons skilled in molecular biology. In one embodiment, they are harvested immediately or promptly following cellular disruption. In another embodiment, a ribonuclease inhibitor is added following harvesting in order to inactivate ribonucleases. In another embodiment, when the nuclions are assembled synthetically from natural or non-natural raw materials, the raw materials are prepared substantially ribonuclease-free or that extant ribonucleases have been rendered sufficiently inactive. In several embodiments, solutions and equipment used for the manufacture and purification of nuclions are substantially free of ribonuclease activity.

In several embodiments, natural nuclions or natural enveloped nuclions can be isolated from natural sources, separated from other cellular components or separated from other nuclions, by using one or more indirect fractionation methodologies.

In several embodiments, another consideration when isolating nuclions or enveloped nuclions from natural sources is that the half-life of the messenger RNA used to form the core nucleic acid can be relatively short. The half-life of mRNAs in bacteria and related eukaryotic organelles is, on average, substantially even shorter than the half-life of mRNAs in the cytoplasm of eukaryota. Furthermore, mature mRNAs in bacteria are often polycistronic, whereas most eukaryotic mRNAs are monocistronic and can be shorter. The net effect of these differences, in several embodiments is that, under predefined conditions, nuclions and enveloped nuclions isolated from eukaryotic sources require different processing times than those from bacterial sources.

In several embodiments, there is a preferred order of ribocapsid assembly for certain types of nuclion, which is followed in the manufacturing process. In one embodiment, tRNA nuclions manufactured from a core RNA and ribocapsid aminoacylated-tRNAs are assembled starting with the charged tRNA on the codon at the 5' end of the ribocapsid region on the CNA, then the ribocapsid is progressively elongated by adding charged tRNAs to the ribocapsid in the 5' to 3' direction, such that the last charged tRNA to be added is bound to the codon at the 3' end of the ribocapsid region on the CNA. In other embodiments, such a sequencing of tRNA addition is not necessary or is not desirable. In other embodiments, such progressive tRNA addition may not be practical or not desirable if multiple codons on a core nucleic acid are specific for the same species of tRNA. In several embodiments, the nuclion will assemble automatically when presented with an appropriate mixture of core nucleic acid and cognate ribocapsid nucleic acids.

Molar Ratio and Nuclion Yield

In several embodiments, it is desirable when manufacturing nuclions to substantially achieve, maintain or exceed a predetermined molar ratio of ribocapsid molecules to core nucleic acid molecules. For example, when manufacturing tRNA nuclions in several embodiments, it is desirable to employ each tRNA in the formulation at a concentration of 10-15 µM and the core nucleic acid at a concentration of 0.05-0.3 µM. In some embodiments, when such conditions are employed and the molar ratio of tRNA:CNA is 50:1, approximately 75% of the CNA is converted to nuclions (that is, the 'nuclion yield' is 75%). In other embodiments, when the molar ratio is raised to 200:1, this nuclion yield increases to 95% or more. In several embodiments, the molar ratio required to achieve a given nuclion yield varies, depending upon the specific tRNAs and CNAs used, the concentration of monovalent, divalent, and polyvalent cations present in the buffer, as well as the pH and temperature of the reaction solution.

Homogeneous and Heterogeneous Preparations

In several embodiments, the manufacturer can elect to produce either homogeneous or heterogeneous preparations of nuclions and ribocapsids, in accordance with the design and functional specifications for a particular application. In some embodiments, the stability of a core nucleic acid ('CNA') is adequately increased by manufacturing a heterogeneous nuclion preparation in which the ratio of tRNA ribocapsid subunit molecules ('tRSM') to core nucleic acid molecules varies. For example, in one embodiment, a predefined core nucleic acid is mixed with a predefined set of tRNA ribocapsid subunits under predefined conditions, whereupon the nuclions assembled all have the same core nucleic acid but the tRSM/CNA ratio varies from 4 to 6. The nuclions in all three nuclion categories (tRSM/CNA ratios of 4, 5 and 6) are then harvested, purified and used as a heterogeneous preparation for the intended purpose.

In other embodiments, it is desirable to separate nuclions with a particular RSM/CNA ratio from nuclions with different RSM/CNA ratios. For example, in one embodiment, a predefined core nucleic acid is mixed with a predefined set of tRNA ribocapsid subunits under predefined conditions, whereupon the nuclions assembled all have the same core nucleic acid but the tRSM/CNA ratio varies from 4 to 6. The nuclions with a tRSM/CNA ratio of 5 are then harvested, purified and used as a homogeneous preparation for the intended purpose.

Methods for the further separation and purification of nuclions are described elsewhere herein and, in several embodiments, these methods are applied to heterogeneous and homogeneous preparations of nuclions. In some embodiments, examples of methods applicable to the separation of nuclions include but are not limited to preparative gel electrophoresis, gel filtration, fast protein liquid chromatography, and ultracentrifugation through a sucrose density gradient. In some embodiments, gel electrophoresis is a preferred nuclion separation method. In one embodiment, this nuclion separation method is implemented by applying a heterogeneous preparation of nuclions to a 7.5-15 cm long non-denaturing 12% polyacrylamide gel run in 90 mM Tris-borate pH 8.3 buffer with 5 mM $MgCl_2$. Depending upon the width and thickness of the gel (0.15-2.0 mm) nuclion preparations ranging from a few µL to a few mL can be applied to the gel. Prior to loading onto the gel the reaction is mixed with 0.1 volume of weighting solution such as 20% glycerol, 0.25% bromophenol blue, 0.25% xylene cyanol. Electrophoresis is then carried out at room temperature or in a cold room until the bromophenol blue indicator reaches the bottom of the gel. If the CNA is radiolabelled, the resolved nuclions (which vary in tRSM/CNA ratio) are visualized by autoradiography or phosphorimagery, otherwise UV shadowing is used. Each band of interest is excised from the gel and nuclion is recovered by electroelution or simple extraction into the buffer of choice. In different embodiments, depending upon the nature of the nuclions prepared, the percentage acrylamide in the gel, and the composition of the running buffer, the time of electrophoresis (as determined by the time at which the indicator reaches the bottom of the gel) varies.

Divalent Cations and Magnesium Concentration

In several embodiments, it is desirable when manufacturing nuclions to substantially achieve, maintain or exceed a predetermined concentration of one or more divalent cations. In several embodiments, the divalent cation is preferably a magnesium ion. Although, in some embodiments, nuclion formation can take place in the absence of divalent cations, in other embodiments the presence of magnesium ion enhances the yield. Relative to nuclion assembly conducted in the absence of divalent cations, the nuclion yield in several embodiments is increased by 40% in presence of 10 mM $MgCl_2$ and by 60% in the presence of 80 mM $MgCl_2$, which is close to saturating in those embodiments. Thus when manufacturing tRNA nuclions in several embodiments, it is desirable to maintain a $MgCl_2$ concentration of 40-80 mM.

Temperature

In several embodiments, it is desirable when manufacturing nuclions to substantially maintain or exceed a predetermined temperature. For example, in some embodiments, when identical reactions are carried out at 37° C. and in an ice bath, both the rate and extent of reaction are greater at the higher temperature. Therefore, when manufacturing tRNA nuclions, in several embodiments it is desirable to conduct the reaction at a predefined temperature of 25-37° C. In other embodiments, it is desirable to maintain a manufacturing temperature below a predefined temperature.

Cross Linking and Psoralens

In several embodiments, it is desirable when manufacturing nuclions to increase the stability of the assembled nuclions. In several embodiments, this is accomplished by cross-linking one or more nuclion components. In several embodiments, a predetermined cross-linker is employed to introduce a covalent linkage between two bases on separate strands of RNA. The strands may be base paired or merely in close proximity. In several embodiments, the cross-linking agent should be efficient, rapid, and reversible but not destructive to the overall nuclion structure. For example, bifunctional nitrogen mustards are inefficient cross-linkers and introduce non-reversible linkages while cis-diaminodichloroplatinum, which reacts with adjacent G's on the same strand, does not introduce interstrand cross-links. Formaldehyde, although an excellent bifunctional cross-linker, reacts with Watson-Crick determinants and denatures some double-stranded DNA and RNA. In contrast, psoralens represent preferred photochemical cross-linking agents for the stabilization of nuclion structure, in several embodiments. These compounds intercalate into double-stranded nucleic acid, including RNA-RNA duplexes, and in the presence of near-ultraviolet light form a covalent link between the two uridines in a double-stranded A-U or U-A sequence. In several embodiments, the photocrosslinkage is rapid and efficient and the resulting cross-link can be conveniently photo-reversed by exposure to 260 nm light. For example, in several embodiments, as long as one or more of the tRNAs that are part of a nuclion has an anticodon bearing A-U or U-A, the anticodons in the ribocapsid subunits and the codons in the codon nucleic acid can be photo-crosslinked by psoralen. Representative psoralens, in several embodiments, include 4,5',8-trimethylpsoralen, 8-methoxypsoralen, and 4-aminomethyl-4,5',8-trimethylpsoralen. Other embodiments employ different methods for the predetermined cross-linking of nuclion components. In several embodiments, cross-linking is desirable to increase the half-life of an active nucleic acid ingredient that is formulated as the core nucleic acid in nuclion complexes. In other embodiments, cross-linking is not necessary.

Example 11: Manufacture of a Basic Nuclion

In one embodiment, a tRNA nuclion composed of Met-tRNAeMet ribocapsid subunits is manufactured as follows: 15 μM Met-tRNAeMet and 0.15 μM core mRNA (with 9 consecutive AUG codons; 5'-GGG-AUG-AUG-AUG-AUG-AUG-AUG-AUG-AUG-AUG-CUU-UCU-AGG-CAC-ACG-AGA-3' SEQ ID NO: 3) are incubated 10 min at 37° C. in 2 mL of 50 mM Tris-HCl pH 7.5, 80 mM MgCl$_2$ ('X1 reaction buffer'). The product manufactured by this method is an example of a basic nuclion.

In order to purify this basic nuclion, it is advantageous to append a desthiobiotin group to the CNA so that nuclions can be purified away from excess tRNA. If the mRNA is chemically synthesized a desthiobiotin group can be directly conjugated to the 3'-end of the RNA at the time of synthesis. Otherwise, if the mRNA is prepared by transcription it can be hybridized to a complementary DNA oligonucleotide which itself is linked to desthiobiotin (e.g., 5'-desthiobiotin-TCTCGTGTGCCTAGAAAG-3': SEQ ID NO: 4). The 5' end of the mRNA can be optionally radiolabelled with $^{32}$P prior to use by treatment with shrimp alkaline phosphatase if needed and then T4 polynucleotide kinase in the presence of γ-$^{32}$P-ATP.

Affinity purification of the nuclions takes advantage of the differential affinity of streptavidin for biotin relative to desthiobiotin. In a related embodiment, following nuclion formation the reaction solution is mixed with streptavidin-sepharose (GE Healthcare) in the upper cup of several Ultrafree-MC filter cartridges (Millipore). After incubation for 10 min the cartridges are centrifuged 10 sec at 10,000 rpm to remove the aqueous solution. The sepharose is then washed twice to eliminate any free tRNA. CNA and associated nuclions are displaced from the streptavidin-sepharose by addition of free biotin, which has a greater affinity for streptavidin than does desthiobiotin. Note that, in this and several other embodiments, all purification steps are carried out in the X1 reaction buffer at 5-10° C.

If electrophoretic analysis demonstrates heterogeneity in the nuclion preparation, individual multimers can usually be resolved by gel filtration chromatography. In some embodiments, it is advantageous to covalently stabilize the ribocapsid subunits by photochemically cross-linking the codon-anticodon triplet by exposure to near-ultraviolet light in the presence of 4-aminomethyl-4,5',8-trimethylpsoralen.

Example 12: Manufacture of an Initiation Nuclion

In one embodiment, a tRNA initiation nuclion with a mixed ribocapsid sequence is manufactured by incubating 15 μM each of fMet-tRNAiMet, Phe-tRNAPhe, and Cys-tRNACys with 0.15 μM of a CNA which codes for fMet-(Phe)$_3$-Cys-Phe-Cys and contains an upstream Shine-Dalgarno sequence (5'-GGGAAGGAGGUAAAA-AUG-UUU-UUU-UUU-UGC-UUU-UGC-UAG-GCA-3'; SEQ ID NO: 5). Reactions are incubated 10 min at 37° C. in 2 mL of 50 mM Tris-HCl pH 7.5, 80 mM MgCl$_2$. Purification of the resulting initiation nuclion is as described in Example 11. The product manufactured by this method is an example of an initiation nuclion.

Example 13: Isolation of a Natural Nuclion

In one embodiment, a natural tRNA nuclion is isolated from a human cell-free extract capable of catalyzing in vitro translation. Such extracts should contain sufficient quantities of charged tRNAs to support ribocapsid formation on an exogenously added mRNA and are commercially available from both Pierce and Avidity. In this embodiment an in vitro transcript coding for β-actin or a portion thereof is added to such an extract. Prior to use, the mRNA is radiolabelled and/or hybridized to a complementary DNA oligonucleotide bearing desthiobiotin, thus facilitating detection and affinity purification. If the mRNA is radiolabeled it can be directly analyzed for nuclion formation by standard electrophoretic or chromatographic methods. Alternatively, if the mRNA has a desthiobiotin affinity tag, it can be purified using streptavidin-sepharose as described in Example 11.

In one embodiment, addition of unmodified β-actin mRNA provides a test for whether nuclions in endogenous mRNAs can be isolated and characterized from freshly lysed human cells. In this embodiment the β-actin mRNA is added together with a desthiobiotin-conjugated DNA oligonucleotide that is complementary to a region in the mRNA which is situated 5' or 3' to the coding sequence. During incubation both nuclion formation and hybridization can take place so that the resulting mRNA can be affinity isolated. Detection of the mRNA following electrophoretic or chromatographic analysis is facilitated, for example, by including a radiolabel in the DNA capture probe or by Northern hybridization. Finally, prior to isolating the β-actin mRNA, nuclion structure is fixed by photo-cross-linkage with psoralen for added stability. The mRNA sequence for human β-actin, including 3' and 5' untranslated regions, is described in Ponte et al. (Ponte et al., 1984, *Nucleic Acids Research* 12: 1687).

The product derived from this process is an example of an isolated nuclion.

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

In the claims articles such as 'a', 'an', and 'the' may mean one or more than one unless indicated to the contrary or otherwise evident from the context. Thus, for example, reference to 'a nuclion' includes a plurality of such nuclions, and reference to 'the tRNA' includes reference to one or more cells known to those skilled in the art, and so forth. Claims or descriptions that include 'or' between one or more members of a group are considered satisfied if one, more than one, or all of the group members are present in, employed in, or otherwise relevant to a given product or process unless indicated to the contrary or otherwise evident from the context. The invention includes embodiments in which exactly one member selected from the group is present in, employed in, or otherwise relevant to a given product or process. The invention includes embodiments in which more than one, or all, of the group members are present in, employed in, or otherwise relevant to a given product or process. Furthermore, it is to be understood that the invention encompasses all variations, combinations, hybrids, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each sub-group of the elements is also disclosed, and any element(s) can be removed from the group. It should it be understood that, in general, where the invention, or aspects of the invention, is/are referred to as consisting of or comprising particular elements, features, etc., certain embodiments of the invention or aspects of the invention consist, or consist essentially of, such elements, features, etc. For purposes of simplicity those embodiments have not been specifically set forth in haec verba herein. It is noted that the terms 'comprising' and 'consisting of' are intended to be open and permit the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nuclion composition, any ribocapsid composition, any nuclion component, any modification, any method of making nuclions, ribocapsids or a nuclion component, any application of nuclions, ribocapsids or nuclion components, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

What is claimed is:

1. A nuclion comprising (i) a core nucleic acid, and (ii) one or more ribocapsids each comprising a polymer of two or more ribocapsid subunits, wherein said ribocapsid subunits comprise nucleic acid, and one or more of said ribocapsid subunits is covalently linked to another ribocapsid subunit, said core nucleic acid or a nuclion envelope.

2. The nuclion of claim 1 wherein (a) at least 50% of the ribocapsid subunits are bound to at least a part of the core nucleic acid, and (b) at least 50% of the ribocapsid subunits are bound to at least a part of one or more adjacent ribocapsid subunits.

3. The nuclion of claim 1, wherein said nuclion additionally comprises one or more nuclion envelopes.

4. The nuclion of claim 3, wherein at least one of the nuclion envelopes is bound to at least a part of (a) the basic nuclion part of the nuclion, (b) a core nucleic acid, (c) one or more of the ribocapsids, (d) one or more of the ribocapsid subunits, (e) another nuclion envelope of the nuclion, or (f) any combination of the foregoing.

5. The nuclion of claim 1, wherein one or more of the ribocapsid subunits comprises RNA.

6. The nuclion of claim 1, wherein one or more of the ribocapsid subunits comprises transfer RNA.

7. The nuclion of claim 1, wherein one or more of the ribocapsid subunits comprises initiator transfer RNA and one or more of the ribocapsid subunits comprises elongator transfer RNA.

8. The nuclion of claim 1, wherein said nuclion is a mimic or counterfeit of (i) a natural nuclion, and said natural nuclion is associated with a cellular organism, an adventitious agent, a virus, a retrovirus, a retroviral tRNA primer complex, a human immunodeficiency virus tRNA primer complex, or any other natural source of a nuclion mimic, or (ii) a nuclion from any non-natural source.

9. The nuclion of claim 1, wherein the core nucleic acid comprises DNA.

10. The nuclion of claim 1, wherein the core nucleic acid comprises RNA.

11. The nuclion of claim 1, wherein the core nucleic acid comprises mRNA.

12. The nuclion of claim 1, wherein the core nucleic acid comprises mRNA, and one or more of the ribocapsid subunits are bound to said mRNA at a start codon or are operably linked to a start codon.

13. The nuclion of claim 1, wherein the core nucleic acid comprises mRNA, and one or more of the ribocapsid subunits are additionally bound to a protein synthesis marker sequence in said mRNA.

14. The nuclion of claim 1, wherein the core nucleic acid comprises mRNA, and one or more of the ribocapsid subunits is additionally bound to a Shine-Dalgarno or Kozak sequence in said mRNA.

15. The nuclion of claim 1, wherein the core nucleic acid comprises mRNA, and one or more nuclion components of the nuclion is additionally bound to at least a part of a ribosome.

16. The nuclion of claim 1, wherein the core nucleic acid comprises mRNA, and said mRNA is bound to at least a part of a ribosome.

17. The nuclion of claim 1, wherein said isolated nuclion is an initiation nuclion, wherein (i) the core nucleic acid comprises mRNA and (ii) at least a part of said mRNA comprises a ribocapsid and/or ribocapsid subunit binding sequence operably linked to the start codon in said mRNA.

18. The nuclion of claim 1, wherein said one or more of said ribocapsid subunits is covalently linked to another ribocapsid subunit.

19. The nuclion of claim 1, wherein said one or more of said ribocapsid subunits is covalently linked to said core nucleic acid.

20. The nuclion of claim 1, wherein said one or more of said ribocapsid subunits is covalently linked to a nuclion envelope.

21. The nuclion of claim 1, wherein said one or more of said ribocapsid subunits is covalently linked to another ribocapsid subunit, said core nucleic acid or a nuclion envelope.

22. The nuclion of claim 1, wherein one or more of said ribocapsids comprises a combination of ribocapsid subunits that does not occur in nature and further comprises (i) ribocapsid subunits from two or more species, (ii) an order of ribocapsid subunits that does not occur in nature, or (iii) a ribocapsid subunit occurring in nature that has been modified chemically or physically to a composition not found in nature.

23. A method of manufacturing a nuclion comprising (i) a core nucleic acid, and (ii) one or more ribocapsids each comprising a polymer of two or more ribocapsid subunits that contain nucleic acid, the method comprising
  combining at least one core nucleic acid and at least two ribocapsid subunits; wherein
  (a) said core nucleic acid comprises a region with multiple binding sites which bind to ribocapsid subunits,
  (b) said ribocapsid subunits each comprise nucleic acid and at least one binding site which binds to a binding site on the core nucleic acid,
  (c) at least 50% of said ribocapsid subunits comprise at least one binding site which binds to a binding site on an adjacent ribocapsid subunit; and
  (d) said ribocapsid subunits are bound within said nuclion by covalent or non-covalent bonds.

24. The method of claim 23, wherein the nuclion is manufactured by combining: (i) a core nucleic acid and two or more ribocapsid subunits, (ii) a core nucleic acid, two or more ribocapsid subunits, and one or more predefined nuclion envelopes, (iii) a basic nuclion and one or more predefined nuclion envelopes, (iv) a core nucleic acid and two or more tRNA ribocapsid subunits, (v) a core nucleic acid, two or more tRNA ribocapsid subunits, and one or more predefined nuclion envelopes, (vi) a basic tRNA nuclion and one or more predefined nuclion envelopes, (vii) an enveloped nuclion and one or more predefined nuclion envelopes, or (viii) a combination of any two or more of the aforesaid members of this group.

25. The method of claim 23, wherein the method comprises one or more steps selected from the group consisting of (1) combining a core nucleic acid preparation with one or more ribocapsid subunit preparations, (2) adding one or more core nucleic acid preparations to a ribocapsid subunit preparation, (3) adding one or more ribocapsid subunit preparations to a core nucleic acid preparation, (4) combining a preparation of core nucleic acid immobilized directly or indirectly on a solid phase with one or more preparations of ribocapsid subunits that are not immobilized, (5) combining one or more preparations of ribocapsid subunits immobilized directly or indirectly on a solid phase with a preparation of core nucleic acid that is not immobilized, (6) combining a preparation of core nucleic acid immobilized directly or indirectly on a solid phase with one or more preparations of ribocapsid subunits immobilized directly or indirectly on a solid phase, (7) combining a core nucleic acid preparation with one or more ribocapsid subunit preparations using a batch process, (8) combining a core nucleic acid preparation with one or more ribocapsid subunit preparations using a continuous process, (9) combining a core nucleic acid preparation with one or more ribocapsid subunit preparations then mixing the combination, (10) combining a core nucleic acid preparation with one or more ribocapsid subunit preparations then separating the resulting nuclions from the core nucleic acid not in nuclions, (11) combining a core nucleic acid preparation with one or more ribocapsid subunit preparations then separating the resulting nuclions from the ribocapsid subunits not in nuclions, (12) combining a core nucleic acid preparation with one or more ribocapsid subunit preparations then separating the resulting nuclions from both the core nucleic acid not in nuclions and the ribocapsid subunits not in nuclions, (13) combining a basic nuclion preparation with one or more nuclion envelope preparations, (14) adding one or more basic nuclion preparations to a nuclion envelope preparation, (15) adding one or more basic nuclion envelope preparations to a nuclion preparation, (16) combining a preparation containing basic nuclions immobilized directly or indirectly on a solid phase with one or more preparations containing nuclion envelopes that are not immobilized, (17) combining one or more preparations containing nuclion envelopes immobilized directly or indirectly on a solid phase with a preparation containing basic nuclions that are not immobilized, (18) combining one or more preparations containing basic nuclions immobilized directly or indirectly on a solid phase with a one or more preparations containing nuclion envelopes immobilized directly or indirectly on a solid phase, (19) combining one or more basic nuclion preparations with one or more nuclion envelope preparations using a batch process, (20) combining one or more basic nuclion preparations with one or more nuclion envelope preparations using a continuous process, (21) combining one or more basic nuclion preparations with one or more nuclion envelope preparations then mixing the combination, (22) combining one or more basic nuclion preparations with one or more nuclion envelope preparations then separating the resulting enveloped nuclions from the nuclions not in enveloped nuclions, (23) combining one or more basic nuclion preparations with one or more nuclion envelope preparations then separating the resulting enveloped nuclions from the nuclion envelopes not in enveloped nuclions, (24) combining one or more basic nuclion preparations with one or more nuclion envelope preparations then separating the resulting enveloped nuclions from both the basic nuclions not in enveloped nuclions and the nuclion envelopes not in enveloped nuclions, (25) combining one or more core nucleic acid preparations with one or more ribocapsid unit preparations and one or more nuclion envelope preparations, (26) combining one or more core nucleic acid preparations with one or more ribocapsid unit preparations and one or more nuclion envelope preparations then mixing the combination, (27) combining one or more core nucleic acid preparations with one or more ribocapsid unit preparations and one or more nuclion envelope preparations then separating the resulting enveloped nuclions from the resulting combination, (28) combining one or more core nucleic acid preparations with one or more ribocapsid unit preparations and one or more nuclion envelope preparations in a batch process, (29) combining one or more core nucleic acid preparations with one or more ribocapsid unit preparations and one or more nuclion envelope preparations in a continuous process, and (30) a combination of any two or more of the aforesaid members of this group.

26. The method of claim 23, wherein the method further comprises one or more steps selected from the group consisting of (1) employing a molar ratio of ribocapsid subunits to core nucleic acid in excess of approximately 1, 2, 5, 10, 20, 30, 40, 50, 60, 70, 80, 90, 100, 200, 300, 400, 500, 600, 700, 800, 900 or 1000; (2) including magnesium chloride, magnesium ions, or magnesium salts at a solution concentration in excess of approximately 1, 2, 5, 10, 20, 30, 40, 50, 60, 70, 80, 90, 100, 200, 300, 400, 500, 600, 700, 800, 900 or 1000 millimoles per liter; (3) omitting polyamines from all solutions and preparations; (4) ensuring that all solutions and preparations are free of nucleases; (5) ensuring that all solutions, equipment, supports, disposables, supplies and other items which contact the reactants or product are substantially free of ribonucleases; (6) employing one or more ribonuclease inhibitors that do not interfere with nuclion assembly or product integrity; (7) allowing sufficient time for assembly wherein said time exceeds 0.1, 1, 5, 10, 20, 30, 40, 50, 60, 120, 180, 240 or 300 seconds; (8) employing a non-denaturing assembly environment, (9) conducting assembly activities at a temperature below approximately 0, 4, 8, 10, 15, 20, 25, 30, 35, 37, 40, 45, 50, 55 or 60 degrees Celsius; (10) chemically cross-linking one or more nuclion components, and (11) any combination of two or more of the aforesaid members of this group.

27. The method of claim 23, wherein the method further comprises isolating the nuclion by one or more steps selected from the group consisting of separation based on size, separation based on shape, separation based on mass, separation based on chemical affinity, separation based on immunological properties, separation using a biotin moiety bound to a nuclion component, separation using a nucleic acid probe bound to a nuclion component, separation based on electrical properties, separation based on osmotic properties, separation based on magnetic properties, separation based on solubility, separation based on electrophoresis in a non-denaturing gel, fractionation of bands following separation in a non-denaturing gel, filtration, dialysis, gel exclusion chromatography, ion exchange chromatography, and a combination of any two or more of the aforesaid members of this group.

28. The method of claim 23, wherein the method further comprises stabilizing the nuclion, during or following manufacture, by one or more steps selected from the group consisting of chemical modification, physical modification, cross-linking, cross-linking a nuclion component, cross-linking two or more nuclion components, introduction of a covalent linkage between two or more bases on separate strands of nucleic acid, exposure to a bifunctional nitrogen mustard, exposure to cis-diaminodichloroplatinum, exposure to formaldehyde, exposure to a psoralen, exposure to 4,5',8-trimethylpsoralen, exposure to 8-methoxypsoralen, exposure to 4-aminomethyl-4,5',8-trimethylpsoralen, freeze-drying, freezing, drying, cooling, addition of a scavenger, addition of an anti-oxidant, addition of a sequestrant, addition of an emulsifier, addition of an excipient, addition of a surfactant, addition of an ultraviolet stabilizer, addition of a ribonuclease inhibitor, and a combination of any two or more of the aforesaid members of this group.

29. The method of claim 23, wherein one or more of said ribocapsid subunits is covalently linked to another ribocapsid subunit.

* * * * *